United States Patent [19]

Summerton et al.

[11] Patent Number: 5,405,938

[45] Date of Patent: * Apr. 11, 1995

[54] SEQUENCE-SPECIFIC BINDING POLYMERS FOR DUPLEX NUCLEIC ACIDS

[75] Inventors: James E. Summerton; Dwight D. Weller, both of Corvallis, Oreg.

[73] Assignee: Anti-Gene Development Group, Corvallis, Oreg.

[*] Notice: The portion of the term of this patent subsequent to Nov. 24, 2009 has been disclaimed.

[21] Appl. No.: 979,158

[22] Filed: Nov. 23, 1992

Related U.S. Application Data

[63] Continuation-in-part of Ser. No. 719,732, Jun. 20, 1991, Pat. No. 5,166,315, which is a continuation-in-part of Ser. No. 454,055, Dec. 20, 1989, Pat. No. 5,034,506.

[51] Int. Cl.$^6$ .................. C08G 59/00; C08G 65/00
[52] U.S. Cl. .................. 528/406; 528/403; 528/425; 528/422; 528/423; 528/245; 528/417; 528/420; 525/383; 525/384; 525/385; 525/542; 525/543
[58] Field of Search ............... 528/406, 403, 425, 422, 528/423, 245, 417, 420; 525/383, 384, 385, 54.2, 54.3

[56] References Cited

U.S. PATENT DOCUMENTS 4,558,047 12/1985 Takaya et al. .

FOREIGN PATENT DOCUMENTS

WO9118898A 6/1990 Japan .

OTHER PUBLICATIONS

Bunemann, H., et al., "Synthesis and Properties of Acrylamide-Substituted Base Pair Specific Dyes for Deoxyribonucleic Acid Template Mediated Synthesis of Dye Polymers," *Biochemistry* 20:2864–2874 (1981).
Chamberlin, M. J., and Patterson, D. L., "Physical and Chemical Characterization of the Ordered Complexes formed between Polyinosinic Acid, Polycytidylic Acid and their Deoxyriboanalogues," *J. Mol. Biol.* 12:410–428 (1965).
Cooney, M., et al., "Site-Specific Oligonucleotide Binding Represses Transcription of the Human c-myc Gene in Vitro," *Science* 241:456–459 (1988).
Fischer-Fantuzzi, L., and Vesco, C., "Cell-Dependent Efficiency of Reiterated Nuclear Signals in a Mutant Simian Virus 40 Oncoprotein Targeted to the Nucleus," *Molecular and Cellular Biology* 8(12):5495–5503 (1988).
Gregoriadis, G., and Neerunjun, E. D., "Homing of Liposomes to Target Cells," *Biochemical and Biophysical Research Communications* 65(2):537–544 (1975).
Hoogsteen, K., "The structure of crystals containing a hydrogen-bonded complex of 1-methylthymine and 9-methyladenine," *Acta Cryst.* 12:822 (1959).
Inman, R. B., "Multistranded DNA Homopolymer Interaction," *J. Mol. Biol.* 10:137–146 (1964).
Kosturko, L. D., et al., "Selective Repression of Transcription by Base Sequence Specific Synthetic Polymers," *Biochemistry* 18(26):5751–5756 (1979).

(List continued on next page.)

Primary Examiner—John Kight, III
Assistant Examiner—Duc Truong
Attorney, Agent, or Firm—Peter J. Dehlinger; Gary R. Fabian

[57] ABSTRACT

The present invention describes a polymer composition effective to bind, in a sequence-specific manner to a target sequence of a duplex polynucleotide, at least two different-oriented Watson/Crick base-pairs at selected positions in the target sequence. The composition includes an uncharged backbone with 5- or 6-membered cyclic backbone structures and selected bases attached to the backbone structures effective to hydrogen bond specifically with different oriented base-pairs in the target sequence. Also disclosed are subunits useful for the construction of the polymer composition. The present invention further includes methods for (i) coupling a first free or polymer-terminal subunit, and (ii) isolating, from a liquid sample, a target duplex nucleic acid fragment having a selected sequence of base-pairs.

26 Claims, 24 Drawing Sheets

OTHER PUBLICATIONS

Kundu, N. G., and Heidelberger, C., "Cyclopenta[f]isoquinoline derivatives designed to bind specifically to native deoxyribonucleic acid. III. Interaction of 6-carbamylmethyl-8-methyl-7H-cyclopenta[f]isoquinolin-3(2H)-one with deoxyribonucleic acids and polydeoxyribonucleotides," *Biochemical and Biophysical Research Communications* 60(2):561–568 (1974).

Kundu, N. G., et al., "Cyclopenta[f]isoquinoline Derivatives Designed to Bind Specifically to Native Deoxyribonucleic Acid. 1. Synthesis of 3-Ethoxy-8-methyl-7(5)H-cyclopenta[f]isoquinoline," *Journal of Medicinal Chemistry* 18(4):395–399 (1975).

Kundu, N. G., et al., "Cyclopenta[f]isoquinoline Derivatives Designed to Bind Specifically to Native Deoxyribonucleic Acid. 2. Synthesis of 6-Carbamylmethyl-8-methyl-7(5)H-cyclopenta[f-isoquinolin-3(2-H)-one and Its Interaction with Deoxyribonucleic Acids and Poly(deoxyribonucleotides)," *Journal of Medicinal Chemistry* 18(4):399–403 (1975).

Kundu, N. G., "New Cyclopenta[a]naphthalene Derivatives. Synthesis of 2-(Carbamylmethyl)-8-hydroxy-3-H-cyclopenta[a]naphthalene as a Possible Deoxyribonucleic Acid Binding Agent," *J. Med. Chem.* 23:512–516 (1980).

Maher, L. J. III, et al., "Inhibition of DNA Binding Proteins by Oligonucleotide-Directed Triple Helix Formation," *Science* 245:725–730 (1989).

Morgan, A. R., and Wells, R. D., "Specificity of the Three-stranded Complex Formation between Double-stranded DNA and Single-stranded RNA containing Repeating Nucleotide Sequences," *J. Mol. Biol.* 37:63–80 (1968).

Moser, H. E., and Dervan, P. B., "Sequence-Specific Cleavage of Double Helical DNA by Triple Helix Formation," *Science* 238:645–650 (1987).

Pelaprat, D., et al., "DNA Intercalating Compounds as Potential Antitumor Agents. 1. Preparation and Properties of 7H-Pyridocarbazoles," *J. Med. Chem.* 23:1330–1335 (1980).

Pelaprat, D., et al., "DNA Intercalating Compounds as Potential Antitumor Agents. 2. Preparation and Properties of 7H-Pyridocarbazole Dimers," *J. Med. Chem.* 23:1336–1343 (1980).

Povsic, T. J., and Dervan, P. B., "Triple Helix Formation by Oligonucleotides on DNA Extended to the Physiological pH Range," *J. Am. Chem. Soc.* 111:3059–3061 (1989).

Schultz, P. G., et al., "Design and Synthesis of a Sequence-Specific DNA Cleaving Molecule. (Distamycin-EDTA)iron(II)," *J. Am. Chem. Soc.* 104(24):6861–6863 (1982).

Schultz, P. G., and Dervan, P. B., "Sequence-specific double-strand cleavage of DNA by penta-N-methylpyrrolecarboxamide-EDTA.Fe(II)," *Proc. Natl. Acad. Sci. USA* 80:6834–6837 (1983).

Sluka, J. P., et al., "Synthesis of a Sequence-Specific DNA-Cleaving Peptide," *Science* 238:1129–1132 (1987).

Youngquist, R. S., and Dervan, P. B., "Sequence-Specific Recognition of B DNA by Bis(EDTA-distamycin)fumaramide," *J. Am. Chem. Soc.* 107:5528–5529 (1985).

Zuidema, D., et al., "The isolation of duplex DNA fragments containing (dG.dC) clusters by chromatography on poly(rC)-Sephadex," *Nucleic Acids Research* 5(7):2471–2483 (1978).

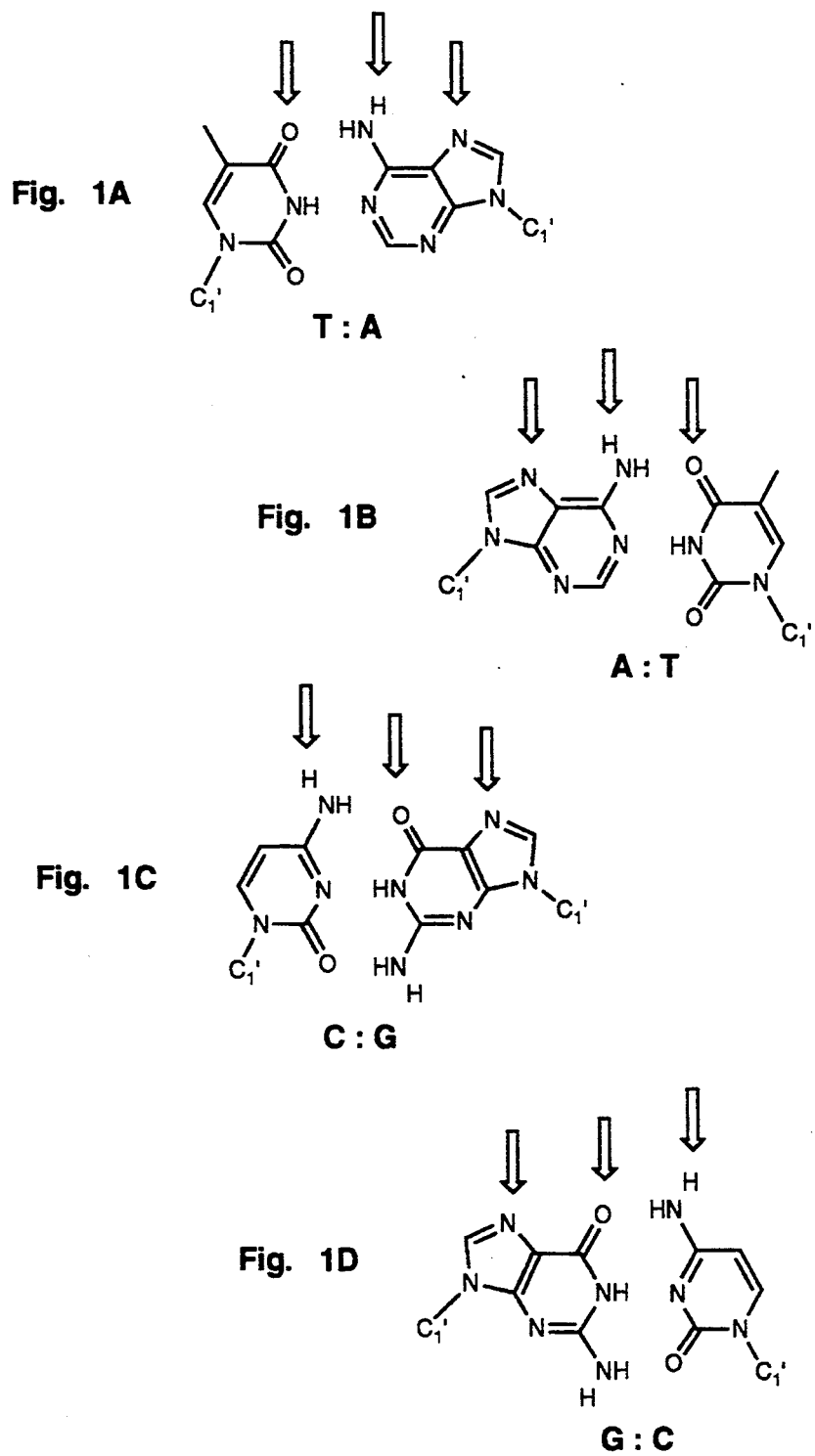
Fig. 1A  T : A
Fig. 1B  A : T
Fig. 1C  C : G
Fig. 1D  G : C

C : G

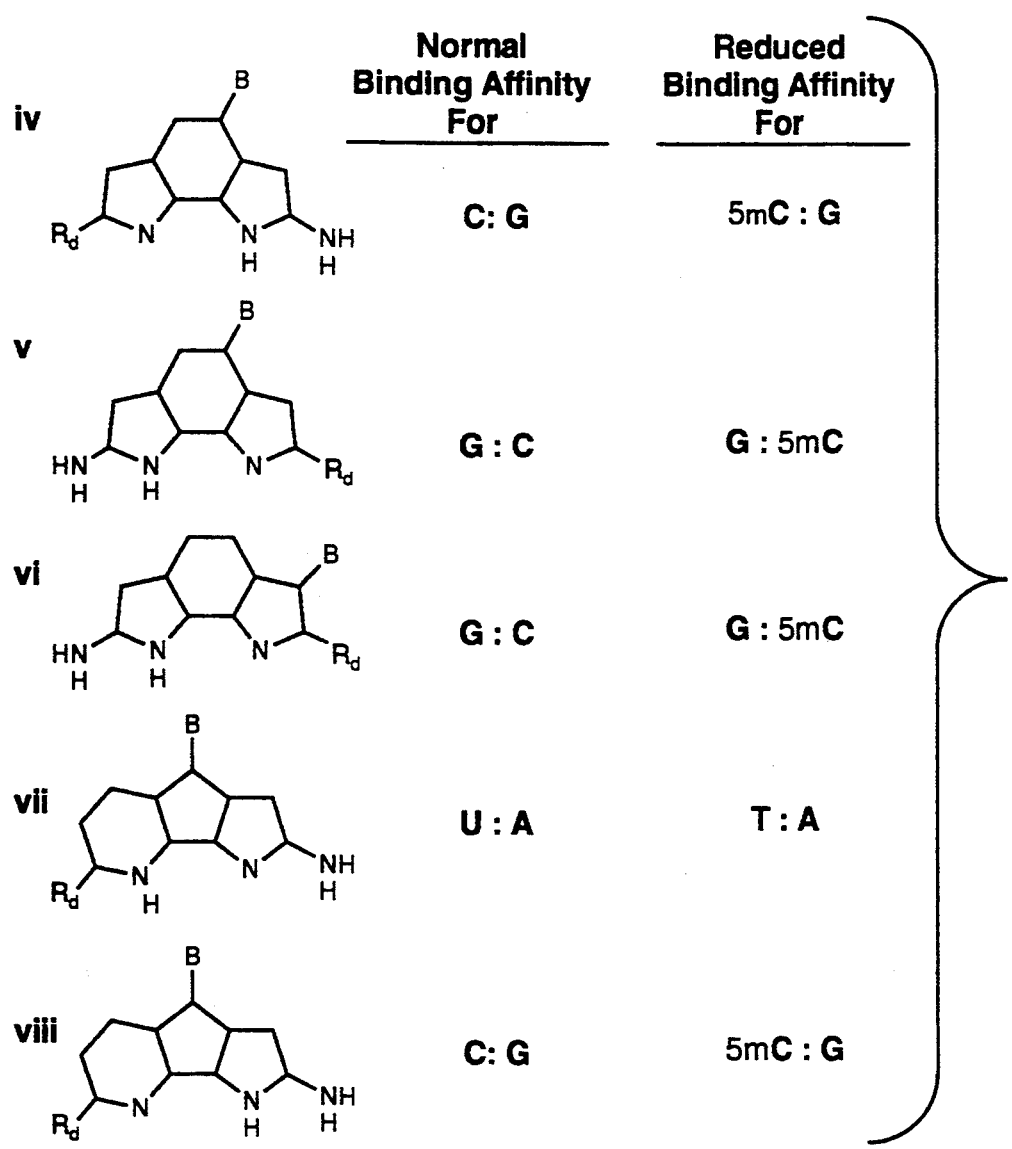
Fig. 4C (con't)
Fig. 5A   Fig. 5B   Fig. 5C
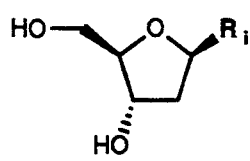 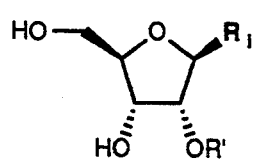 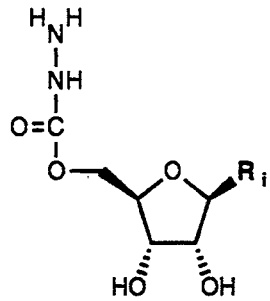

C : G

T : A

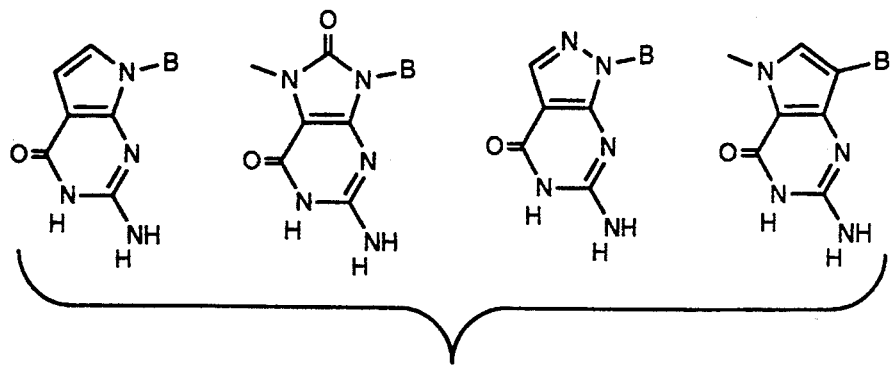
Fig. 10E
Fig. 11A
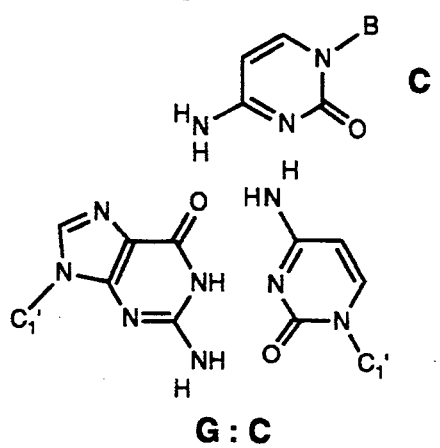
G : C
Fig. 11B
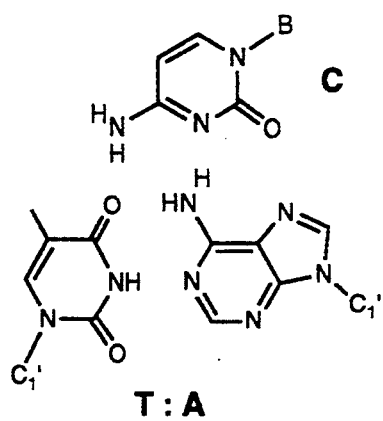
T : A
Fig. 12A
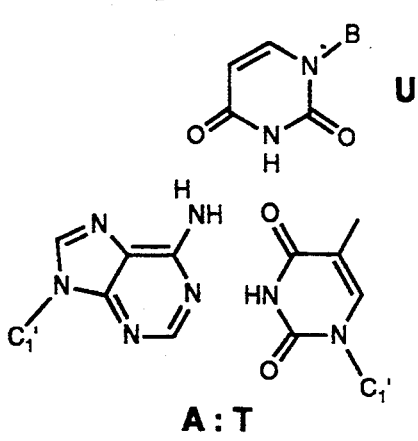
A : T
Fig. 12B
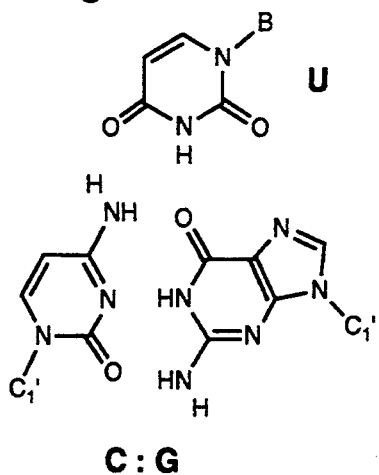
C : G

G : C

A : T

G : C

G : C

A : T

G : C

A : T

A : T

C : G

T : A

U : A

C : G

A : T

G : C

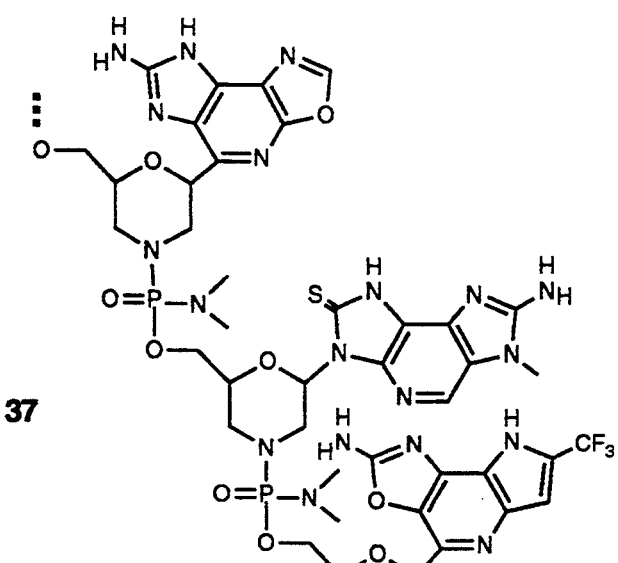
Fig. 37
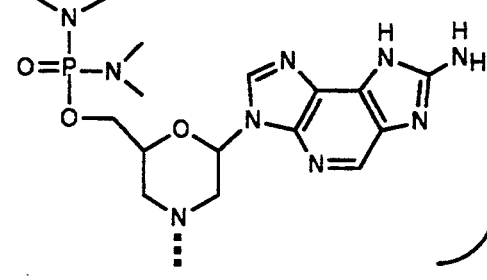
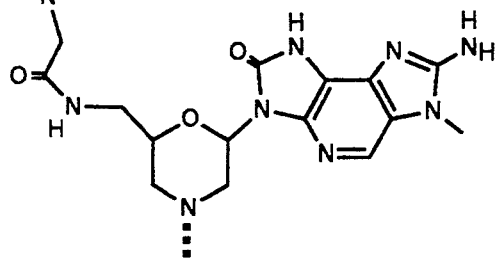
Fig. 38

SEQUENCE-SPECIFIC BINDING POLYMERS FOR DUPLEX NUCLEIC ACIDS

The present invention is a continuation-in-part application of U.S. patent application Ser. No. 719,732, filed Jun. 20, 1991, now U.S. Pat. No. 5,166,315 and herein incorporated by reference, which is a continuation-in-part of U.S. patent application Ser. No. 07/454,055, filed Dec. 20, 1989 (now issued as U.S. Pat. No. 5,034,506).

FIELD OF THE INVENTION

The present invention relates to an uncharged polymer capable of binding with sequence specificity to double stranded nucleic acids containing a selected base-pair sequence.

REFERENCES

Aboderin, Delpierre, and Fruton, J. Amer. Chem. Soc. 1965, 87, 5469.

Aoyama (1987). Bull. Chem. Soc. Jpn. 60 2073.

Arnott & Bond (1973). Science 181 68; Nature New Biol. 244 99.

Arnott & Selsing (1974). J. Molec. Biol. 88 509.

Balgobin, McBride, Kierzek, Beaucage and Caruthers Bassingdale (1986). J. Amer. Chem. Soc. 108 2040.

Barwolff and Langen, in "Nucleic Acid Chemistry," Townsend and Tipson, Ed. Wiley, New York, 1978 page 359.

Belikova, Zaratova, & Grineva (1967). Tet. Letters 37 3557. Bischofberger, Tetrahedron Letters (1987) 28 821.

Bredereck, et al, Chemische Berichte (1968) 101 41.

Bunemann et al. (1981). Biochem. 20 2864.

Caballero, Mota & Perez (1986). Carbohydrate Research 154 280.

Carnelley and Dutt, J. Chem. Soc. 125, 2483.

Chamberlin & Patterson (1965). J. Molec. Biol. 12 410.

Chelsky et al. (1989). Mol. Cell. Biol. 2487.

Cooney et al. (1988). Science 241 456.

Corey, Gilman, and Ganem (1968). J. Am. Chem. Soc. 90 5616.

Dehlinger, P., (1992). Journal of the US Patent and Tradmark Office Society, July Issue, pages 463–480.

Dervan, P. B., (1986). Science 232, 464–471.

Dreyer, G. B., et al., (1985). Proc. Natl. Acad. Sci. USA 82, 968–972.

Elguero et al. (1976). The Tautomerism of Heterocycles, Adv. in Heterocyclic Chem. Supplement I. Academic Press. N.Y.

Fernandez-Resa, et al. (1989). J. Chem. Soc. Perkin 1:67.

Fischer-Fantuzzi & Vesco (1988). Molec. & Cell. Biol. 8 5495.

Flavell & Van den Berg (1975). FEBS Letters 58 90.

Froehler (1986). Tetrahedron Lett. 27:5575.

Gregoriadis & Needunjun (1975). Biochem. Biophys. Res. Commun. 65 537.

Hamamichi & Miyasaka (1991). J. Heterocyclic Chem., 28 397.

Hanessian, Martin, & Desai (1986). J. Chem. Soc., Chem. Commun., 926.

Himmelsbach and Pfleiderer (1983). Tet. Lett. 24 3583.

Hoffer (1960). Chemische Berichte 93 2777.

Hoogsteen (1959). Acta Cryst. 12 822.

Ikehara & Kaneko (1970). Chem. Pharm. Bull., 18 2441.

Inaman (1964). J. Mol. Biol. 10 137.

Jones (1979). Int. J. Biol. Macromolec. 1194.

Jurgens (1907). Chemische Berichte 40 4409.

Kabanov (1989). FEBS Letters 258 343.

Kamimura, Tsuchiya, Urakami, Koura, Sekine, Shinozaki, Miura and Hata (1984). J. Amer. Chem. Soc. 106 4552.

Karpova et al. (1980). FEBS Letters 122 21.

Katritzky and Yates (1976). J. Chem. Soc., Perkin Trans. 1309.

King, McWhirter, and Barton (1945). J. Am. Chem. Soc. 67 2089.

Kosturko et al. (1979). Biochem. 18 5751.

Kundu & Heidelberger (1974). Biochem. Biophys. Res. Comm. 60 561.

Kundu et al. (1975). J. Med. Chem. 18 395 & 399.

Kundu (1980). J. Med. Chem. 23 512.

Kunz & Pfrengle (1989). Angew. Chem. Int. Ed. Eng., 28 1067.

Lemaitre, Bayard & Leblue (1987). PNAS 84 648.

Maeba et al (1983). J. Org. Chem. 48 2998.

Maher III, L. J., Wold, B., & Dervan, P. B. (1989). Science 245, 725–730.

Mahler, Wold, Dervan (1989). Science 245 725.

Martin (1964). J. Chem. Soc., 2944.

McBride, et al. (1986). J.A.C.S. 108:2040.

Miller et al. (1979). Biochemistry 18 5134.

Miller et al. (1980). J. Biol. Chem. 255 9659.

Miller et al. (1985). Biochimie 67 769.

Miura and Hata (1984). J. Amer. Chem. Soc. 106 4552.

Morgan & Wells (1968). J. Molec. Biol. 37 63.

Moser & Dervan (1987). Science 238 645.

Mulzer, Kuhl & Bruntrup (1978). Tetrahedron Letters, 2249 & 2253.

Myers and Lee (1984). Carb. Res. 132 61.

Outten and Daves (1987). J. Org. Chem. 52 5064.

Ozdowska (1974). Rocz. Chem. 48 1065.

Pelaprat et al. (1980) J. Med. Chem. 23 1330, 1336.

Peltier (1956). Belg. Soc. Science, Bretagne 31 26.

Phillips (1928). J. Chem. Soc. 2393.

Pickering, Srivastava, Witkowski, and Robins, Nucleic Acid Chemistry, Part 1, Ed. by Townsend and Tipson, John Wiley and Sons, N.Y., p 145.

Pitha & Pitha (1970). Biopolymers 9 965.

Poisel and Schmidt (1975). Chemische Berichte 108 2547.

Povich (1989). J. Amer. Chem. Soc. 111 3059.

Rich & Seeman (1975). Handbook of Biochemistry and Molecular Biology, 3rd Edition, Vol. 2, pages 465–466.

Robbins & Basom (1978). in Nucleic Acid Chemistry, part 2, Townsend & Topson, Eds. p601.

Robins, Naik, and Lee (1974). J. Org. Chem. 39 1891.

Robins, Hansske, Bernier (1981). Can. J. Chem. 59 3360.

Sakataume, et al. (1990). Nuc. Acids. Res. 18:3327.

Sakore et al. (1969). J. Molec. Biol. 43 385.

Satoda, Komori, Terashima & Yaginamu, Japanese Kokai, 74 85092.

Schmitz & Galas (1979). Nucleic Acids Res. 6 111.

Schnneller and Christ (1981). J. Heterocyclic Chem. 18 654.

Schultz, Taylor, & Dervan (1982). JACS 104 6861.

Schultz & Dervan (1983). PNAS 80 6834.

Seela & Hasselmann (1981). Chemische Berichte 114 3395.

Sekine, Peshakova, Hata, Yokoyama and Miyazawa (1987). J. Org. Chem. 52 5061.

Shioiri, Ninomiya, Yamada (1972). J. Amer. Chem. Soc. 94 6203.

Sluka et al. (1987). Science 238 1129.

Smith (1954). J. Chem. Soc., 3842.

Smith, Rammler, Goldberg & Khorana (1961). J. Amer. Chem. Soc. 84 430.

Stirchak, Summerton, & Weller (1987). J. Org. Chem. 52 4202.

Stirchak, Summerton, & Weller (1989). Nucleic Acids Res. 17 6129.

Summerton & Bartlett (1978b). J. Molecular Biology 122 145–162.

Summerton (1979). J. Theor. Biol. 78 61–76.

Summerton (1979). J. Theor. Biol. 78 77–99.

Tamura and Okai (1984). Carb. Res. 133 207.

Toulme et al. (1986). PNAS 83 1227.

Touster (1975) "Organic Reactions", R. E. Krieger Publishers, Inc. N.Y. vol. 7:327.

Trattner, et al (1964). J. Org. Chem. 29 2674.

Trichtinger, Charbula and Pfleiderer (1983). Tet. Lett. 24 711.

Voet & Rich (1970). Progress in Nucleic Acids Res. & Molec. Biol. 10 183–265.

Winkeler & Seela (1983). J. Org. Chem. 48 3119.

Wittenburg (1964). Z. Chem., 4 303.

Yardley & Fletcher (1976). Synthesis 244.

Youngquist & Dervan (1985). JACS 107 5528.

Zamecnik & Stephenson (1978). PNAS 75 280.

Zimmermann & Stille (1985). Macromolecules 18 321.

Zuidema, Van den Berg & Flavell (1978). Nucleic Acids Res. 5 2471.

BACKGROUND OF THE INVENTION

Oligonucleotides or oligonucleotide analogs designed to inactivate selected single-stranded genetic sequences unique to a target pathogen were first reported in the late 1960's by Belikova, 1967, and subsequently by: Pitha, 1970; Summerton, 1978a,b, 1979a,b; Zamecnik, 1978; Jones, 1979; Karpova, 1980; Miller, 1979, 1980, 1985; Toulme, 1986; and Stirchak, 1987, 1989. Polymeric agents of this type achieve their sequence specificity by exploiting Watson/Crick base pairing between the agent and its complementary single-stranded target genetic sequence. Because such polymers only bind single-stranded target genetic sequences, they are of limited value where the genetic information one wishes to inactivate exists predominantly in the double-stranded state.

For many pathogens and pathogenic states duplex genetic sequences offer a more suitable target for blocking genetic activity. One of the earliest attempts to develop a sequence-specific duplex-directed nucleic acid binding agent was reported by Kundu, Heidelberger, and coworkers during the period 1974 to 1980 (Kundu 1974; Kundu 1975; Kundu 1980). This group reported two monomeric agents, each designed to hydrogen-bond to a specific base-pair in duplex nucleic acids. However, these agents were ineffective, probably for two reasons. First, they utilized a nonrigid ambiguous hydrogen-bonding group (an amide) which can act as either a proton donor or acceptor (in the hydrogen-bonding sense). Secondly, they provided an insufficient number of hydrogen bonds (two) for complex stability in aqueous solution. Experimental results from a variety of systems suggest that hydrogen-bonded complexes are stable in aqueous solution only if there are a substantial number (probably at least 12) of cooperative intermolecular hydrogen bonds, or if there are additional stabilizing interactions (electrostatic, hydrophobic, etc.).

Another early attempt was reported by Dattagupta and Crothers at Yale and coworkers in Germany (Kosturko 1979; Bunemann 1981). These workers employed a polymer prepared from a dye known to intercalate into duplex DNA rich in G:C base-pairs and another dye which preferentially binds to duplex DNA rich in A:T base-pairs, probably via minor-groove sites. Preparation of the polymer involved modification of the two dyes by adding acrylic moieties and then polymerization of a mixture of the modified dyes in the presence of duplex DNA of defined sequence (the template). The expectation was that the resultant polymer would show a specific affinity for duplex DNA having the same sequence as the template DNA. However, such material proved to exhibit only nominal sequence specificity. A variety of bis-intercalating agents designed to bind to specific sequences in duplex DNA have also been reported (Pelaprat, 1980), but such agents inherently give only minimal sequence specificity.

More recently, Dervan has taken a natural B-form-specific minor-groove-binding antibiotic (Distamycin) and systematically extended its structure to achieve a significant level of sequence specificity (Schultz 1982; Schultz 1983; Youngquist 1985). He has also appended to this oligomer an EDTA/Fe complex which under certain conditions acts to cleave the duplex target sequence near the agent's binding site. However, this particular approach will not lead to the high level of specificity which is needed for therapeutic applications because the inherent symmetry of the H-bonding sites in the minor groove provides too little sequence information.

Still more recently, Dervan and coworkers reported a binding agent which utilizes the informationally-richer polar major-groove sites of a target genetic duplex for sequence-specific recognition (Sluka 1987). This entailed adapting a synthetic polypeptide, comprising the DNA-sequence-recognition portion of a DNA-binding protein, for cleaving DNA at the protein's binding site on duplex DNA. The cleaving activity was achieved by linking an EDTA/Fe complex to the amino terminus of the synthetic peptide and demonstrating that this complex selectively cleaved duplex DNA at or near the parent protein's natural target sequence.

Another approach to duplex targeting has grown out of studies first reported in the late 1950's that demonstrated, via X-ray diffraction, that under high salt conditions an all-thymine or all-uracil polynucleotide can bind to specific polar major-groove sites on a Watson/Crick genetic duplex having all adenines in one strand and all thymines or uracils in the other strand (Hoogsteen binding; Hoogsteen 1959). Subsequently, it was reported that in high salt and at pH values lower than 7, an all-cytosine polynucleotide, having the cytosine moieties protonated, can bind in a similar manner to a Watson/Crick duplex having all guanines in one strand and all cytosines in the other strand.

Thereafter, is was demonstrated that under high salt and at a pH below 7, a polynucleotide containing both cytosines and thymines (or uracils) can bind to a Watson/Crick duplex having the appropriate sequence of purines in one strand and pyrimidines in the other strand (Morgan, 1968).

In the 1970's this Hoogsteen binding mechanism was exploited for affinity chromatography purification of duplex genetic fragments containing runs of purines in one strand and pyrimidines in the other strand (Flavell, 1975; Zuidema, 1978). In 1987 Dervan and coworkers exploited this Hoogsteen binding mechanism to position an all-pyrimidine polynucleotide, carrying an EDTA/Fe cleaving moiety, onto a target genetic duplex having a specific sequence of purines in one strand and pyrimidines in the other strand (Moser, 1987).

A major-groove binding mode different from the Hoogsteen mode was reported in the mid-1960's and involves binding of an all-purine polynucleotide, poly(dI), to a poly(dI)/poly(rC) duplex (Inamn 1964) and to a poly(dI)/poly(dC) duplex (Chamberlin 1965). Similarly, a mostly-purine polynucleotide has been recently used by Hogan and coworkers (Cooney, 1988) for blocking the activity of a selected natural duplex genetic sequence. These workers reported that in the presence of 6 mM Mg++ a mostly-purine polynucleotide (24 purines, 3 pyrimidines) of a specific sequence inhibits transcription of the human C-myc gene in a cell-free system.

To date, reported polynucleotides used for binding to genetic duplexes fail to satisfy one or more important criteria for effective use within living organisms. Some of these criteria are as follows:

First, the Hoogsteen-binding polynucleotides (polypyrimidines) containing cytosines require a lower-than-physiological pH in order to achieve effective binding (due to the necessity of protonating the cytosine moieties), although it has recently been demonstrated by Dervan and coworkers that the use of 5-methylcytosines in place of cytosines allows Hoogsteen binding at a pH somewhat closer to physiological (Mahler, 1989), and use of both 5-methylcytosines in place of cytosines and 5-bromouracils in place of thymines (or uracils) improves binding still further (Povsic, 1989).

Second, in the case of polypurine polynucleotides, both inosine (hypoxanthine) and adeninc moieties lack adequate sequence specificity and adequate binding affinity for effective major-groove binding in intracellular applications. The inadequate sequence specificity for inosine (Inman, 1964) and adenine (Cooney, 1988) moieties derives from the fact that inosine can bind with similar affinity to the central polar major-groove sites of both a C:I (or C:G) base-pair (i.e., NH4 of C and 06 of G or I) and an A:T or A:U base-pair (i.e., NH6 of A and 04 of T or U), and because adenine can bind with similar affinity to the central polar major-groove sites of both a T:A or U:A base-pair (i.e., 04 of T or U and NH6 of A) and a G:C base-pair (i.e., 06 of G and NH4 of C), as discussed further below.

The low binding affinity of inosine for its target base-pairs and of adenine for its target base-pairs is due to the fact that these purines can form only two less-than-optimal hydrogen-bonds to the major-groove sites of their respective target base-pairs.

Third, both polypyrimidine and polypurine polynucleotides fail to achieve effective binding to their target genetic duplexes under physiological conditions, due to the substantial electrostatic repulsion between the three closely-packed polyanionic backbones of the three-stranded complexes. Although this repulsion can be attenuated by high salt (Morgan, 1968), divalent cations (Cooney, 1988), or polyamines (Moser, 1987), nonetheless, for applications in living cells, and particularly cells within intact organisms, control of intracellular cation concentrations is generally not feasible.

Fourth, for therapeutic applications polynucleotides are less than optimal because: (i) they are rapidly sequestered by the reticuloendothelial lining of the capillaries, (ii) they do not readily cross biological membranes, and (iii) they are sensitive to degradation by nucleases in the blood and within cells.

For many in vivo applications of sequence-specific duplex-directed nucleic acid-binding agents, the principal target is DNA, which appears to exist within cells predominantly in a B or B-like conformation. In this context, polynucleotides which have been used for major-groove binding to genetic duplexes (Moser, 1987; Cooney, 1988) have a unit backbone length that is shorter than optimal for binding to duplex genetic sequences existing in a B-type conformation.

SUMMARY OF THE INVENTION

The present invention includes a polymer composition effective to bind in a sequence-specific manner to a target sequence of a duplex polynucleotide containing at least two different oriented Watson-Crick base-pairs at selected positions in the target sequence. The polymer is formed of a specific sequence of subunits selected from the following forms:

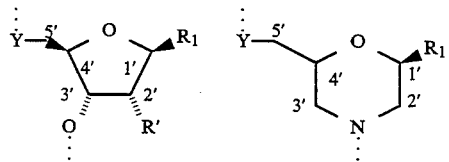

where Y is a 2- or 3-atom length, uncharged intersubunit linkage group; R' is H, OH, or O-alkyl; the 5'-methylene has a $\beta$ stereochemical orientation in the 5-membered ring and a uniform stereochemical orientation in the 6-membered ring; $R_i$ has a stereochemical orientation; and at least about 70% of groups in the polymer are selected from two or more of the following base-pair-specificity groups:

A. for a T:A or U:A oriented base-pair, $R_i$ is selected from the group consisting of planar bases having the following skeletal ring structures and hydrogen bonding arrays, where B indicates the polymer backbone:

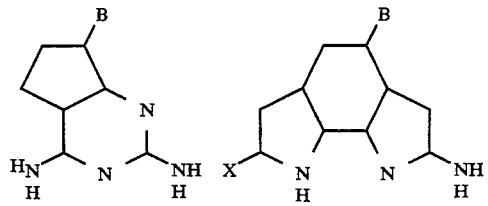

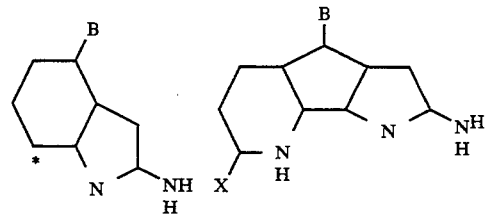

where the * ring position may carry a hydrogen-bond donor group, such as an amine; and X may be a moiety effective to afford discriminative binding on the basis of the moiety at the 5 position of the pyrimidine of the target base-pair;

B. for a C:G oriented base-pair, $R_i$ is selected from the group consisting of planar bases having the following skeletal ring structures and hydrogen bonding arrays, where B indicates the polymer backbone:

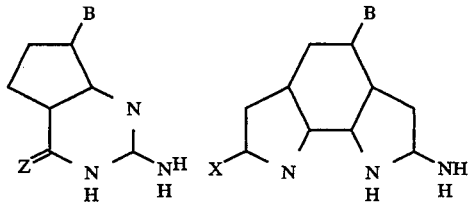

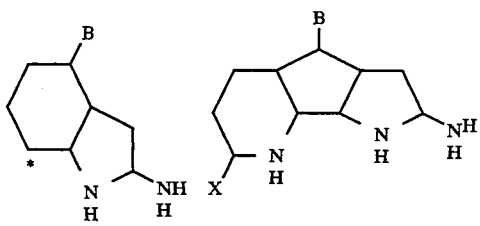

where the * ring position may carry a hydrogen-bond acceptor group, such as a carbonyl oxygen; X may be a moiety effective to afford discriminative binding on the basis of the moiety at the 5 position of the pyrimidine of the target base-pair; and Z is oxygen or sulfur;

C. for a G:C oriented base-pair, $R_i$ is selected from the group consisting of planar bases having the following skeletal ring structures and hydrogen bonding arrays, where B indicates the polymer backbone:

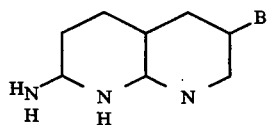

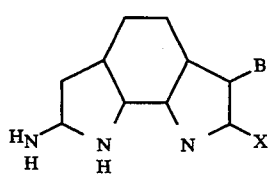

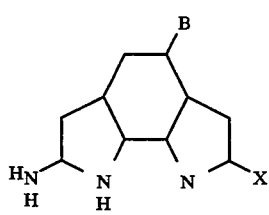

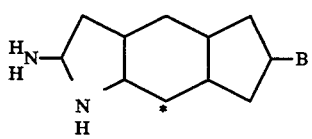

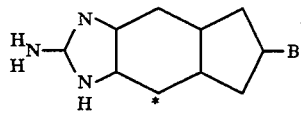

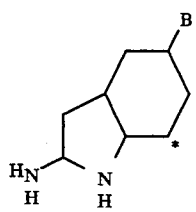

where the * ring position may carry a hydrogen-bond acceptor group, such as a carbonyl oxygen; and X may be a moiety effective to afford discriminative binding on the basis of the moiety at the 5 position of the pyrimidine of the target base-pair; and, D. for an A:T or A:U oriented base-pair, $R_i$ is selected from the group consisting of planar bases having the following skeletal ring structures and hydrogen bonding arrays, where B indicates the polymer backbone:

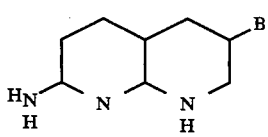

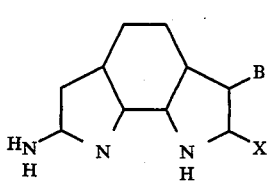

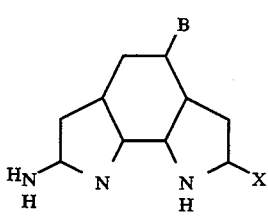

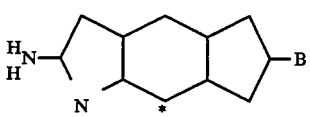

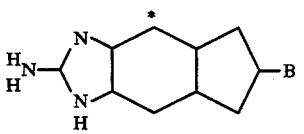

-continued

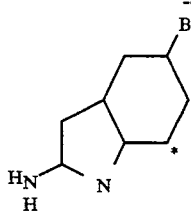

where the * ring position may carry a hydrogen-bond donating group, such as NH₂; and X may be a moiety effective to afford discriminative binding on the basis of the moiety at the 5 position of the pyrimidine of the target base-pair.

In one embodiment, for use in sequence-specific binding to a duplex nucleic acid sequence in an A conformation, the Y linkage group is two atoms in length. In another embodiment, for use in sequence-specific binding to a B-form DNA-DNA duplex nucleic acid sequence, the Y linkage group is three atoms in length.

In another embodiment, the invention includes a polymer containing several methyl-discriminating bases which afford good target binding affinity to a duplex target sequence when said target sequence contains a hydrogen at the 5 position of the pyrimidine of selected base-pairs, but which substantially reduce target binding to a corresponding target sequence when said target sequence contains a methyl at the 5 position of the pyrimidine of the selected base-pairs.

In another aspect, the invention includes a method for coupling a first free or polymer-terminal subunit having one of the following subunit forms:

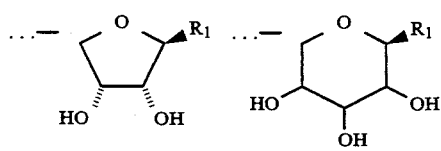

where $R_i$ is a planar ring structure having two or more hydrogen-bonding sites, with a second free or polymer-terminal subunit having one of the following subunit forms:

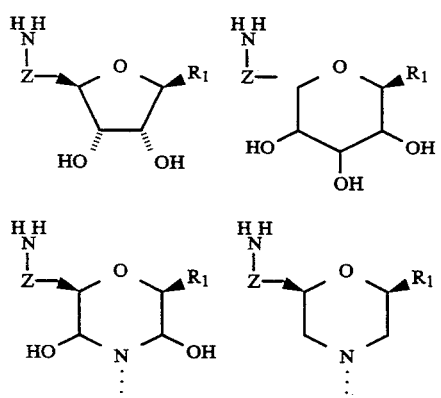

where Z is a 2-atom or 3-atom long moiety. The method includes i) oxidizing the first subunit to generate a dialdehyde intermediate; ii) contacting the dialdehyde intermediate with the second subunit under conditions effective to couple a primary amine to a dialdehyde; and (iii) adding a reducing agent effective to give a coupled structure selected from the following forms:

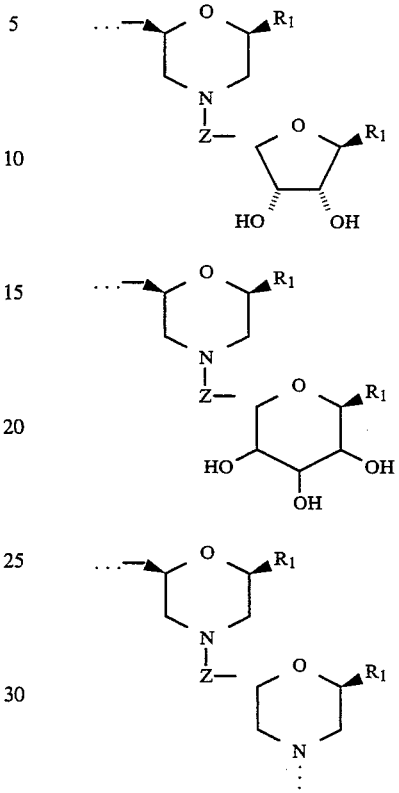

In still another aspect, the invention provides a method for isolating, from a liquid sample, a target duplex nucleic acid fragment having a selected sequence of base-pairs. The method includes first contacting the sample with a polymer reagent-containing structure which allows isolation of the reagent from solution, and attached to this structure, a polymer composition of the type described above, where the polymer composition has a subunit sequence effective to bind in a sequence-specific manner with the selected sequence of base-pairs. The contacting is carried out under conditions effective for sequence-specific binding of the polymer composition to the selected sequence of base-pairs.

Further, the polymers of the present invention can be used to detect the presence of a target nucleic acid sequence. For example, a support-bound polymer composition can be contacted with a test solution containing the selected duplex genetic sequence under conditions effective for sequence-specific binding of the polymer composition to its target sequence of base-pairs. The support-bound polymer with bound selected duplex genetic sequence is then separated from the test solution. The presence of the polymer/target duplex sequence is then detected. Detecting the selected genetic sequence may, for example, utilize one of the following: fluorescent compounds, such as, ethidium bromide and propidium iodide, effective to intercalate into duplex genetic sequences; or reporter moieties linked to oligocationic moieties effective to bind to the polyanionic backbone of nucleic acids.

Also forming part of the invention is a subunit composition for use in forming a polymer composition effective to bind in a sequence specific manner to a target sequence in a duplex polynucleotide. The composition includes one of the following subunit structures:

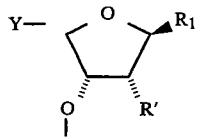
(a)

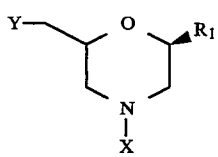
(b)

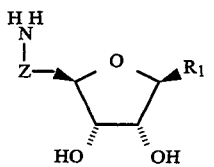
(c)

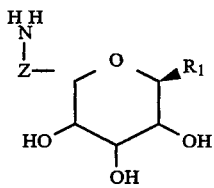
(d)

where R' is H, OH, or O-alkyl; the 5'-methylene has a β stereochemical orientation in subunit forms (a), (c), and (d) and a uniform stereochemical orientation in subunit form (b); X is hydrogen or a protective group or a linking group suitable for joining the subunits in any selected order into a linear polymer; Y is a nucleophilic or electrophilic linking group suitable for joining the subunits in any selected order into a linear polymer; and X and Y together are such that when two subunits of the subunit set are linked the resulting intersubunit linkage is 2 or 3 atoms in length and uncharged; Z is a 2-atom or 3-atom long moiety; and, $R_i$, which may be in the protected state and has a β stereochemical orientation, is selected from the group consisting of planar bases having the following skeletal ring structures and hydrogen bonding arrays, where B indicates the aliphatic backbone moiety:

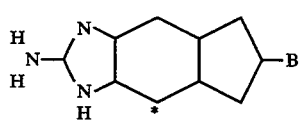

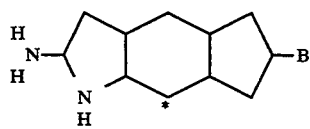

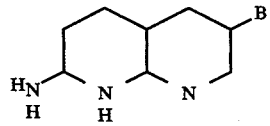

-continued

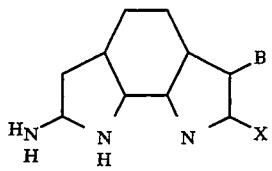

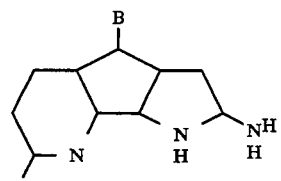

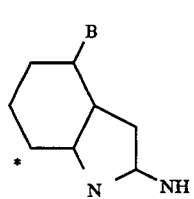

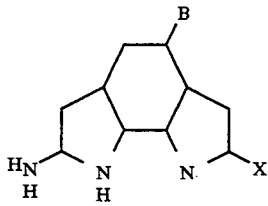

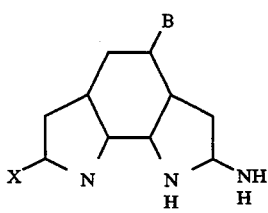

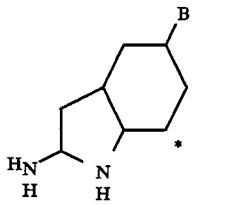

where the * ring position may carry a hydrogen-bond acceptor group; and X may be a moiety effective to afford discriminative binding on the basis of the moiety at the 5 position of the pyrimidine of the target base-pair; or, where $R_i$ is selected from the group consisting of planar bases having the following skeletal ring structures and hydrogen bonding arrays, where B indicates the aliphatic backbone moiety:

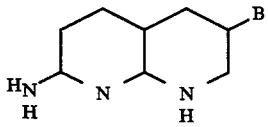

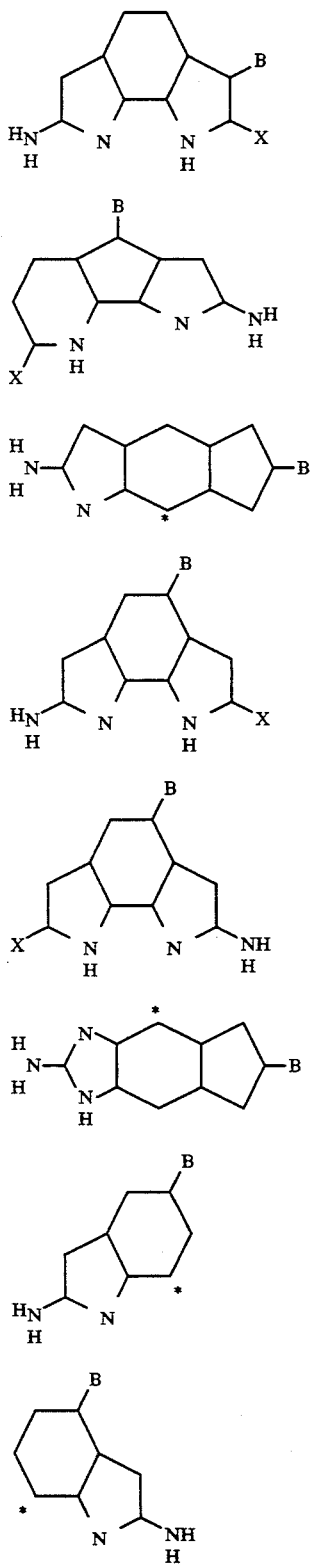

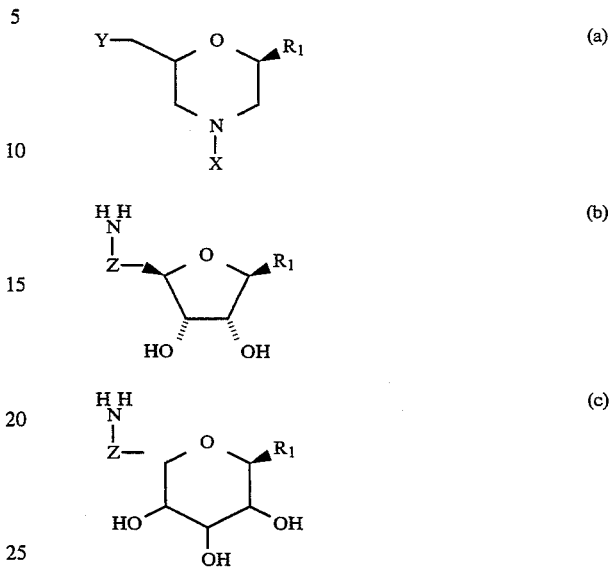

where the * ring position may carry a hydrogen-bond donating group; and X may be a moiety effective to afford discriminative binding on the basis of the moiety at the 5 position of the pyrimidine of the target base-pair.

An additional part of the invention is a subunit composition for use in forming a polymer composition effective to bind in a sequence specific manner to a target sequence in a duplex polynucleotide. The composition includes one of the following subunit structures:

where the 5'-methylene has a β stereochemical orientation in subunit forms (b), and (c) and a uniform stereochemical orientation in subunit form (a); X is hydrogen or a protective group or a linking group suitable for joining the subunits in any selected order into a linear polymer; Y is a nucleophilic or electrophilic linking group suitable for joining the subunits in any selected order into a linear polymer; and X and Y together are such that when two subunits of the subunit set are linked the resulting intersubunit linkage is 2 or 3 atoms in length and uncharged; Z is a 2-atom or 3-atom long moiety; and, $R_i$, which may be in the protected state and has a β stereochemical orientation, is selected from the group consisting of planar bases having the following skeletal ring structures and hydrogen bonding arrays, where B indicates the aliphatic backbone moiety, the starred atom is not a hydrogen bond acceptor, and W is oxygen or sulfur:

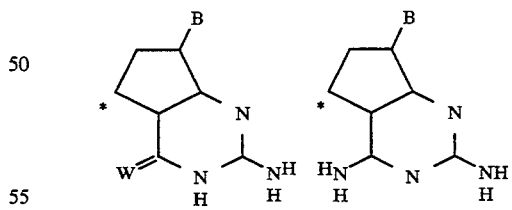

The present invention also includes, a polymer composition capable of discriminating, on the basis of binding affinity, between (a) a selected target sequence in a duplex polynucleotide containing at least one pyrimidine-purine base-pair at a selected position in the target sequence, where the pyrimidine base has a hydrogen on the 5 ring position, and (b) the same sequence but in which the pyrimidine of the base pair at the selected position contains a methyl group on the 5 ring position of the pyrimidine. The polymer composition includes a polymer having the repeating unit

where B is a backbone moiety. In the composition, at least one $R_i$ is selected from the following group:

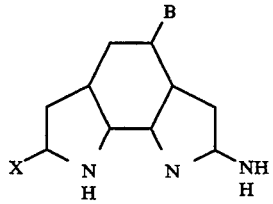
(a)

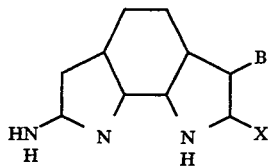
(b)

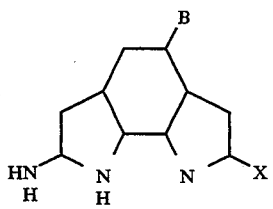
(c)

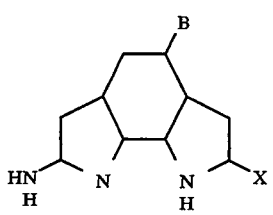
(d)

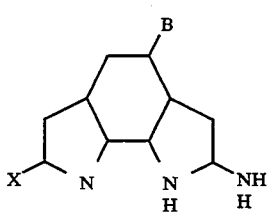
(e)

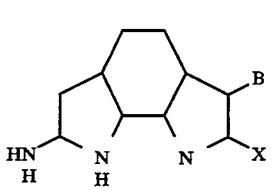
(f)

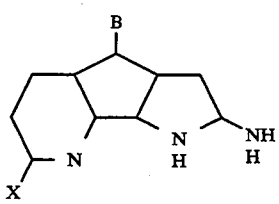
(g)

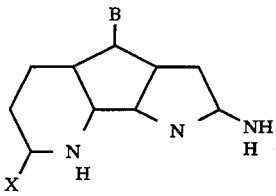
(h)

where X has a size and shape effective to selectivity reduce binding of $R_i$ to a base-pair having a methyl on the 5 ring position of the pyrimidine.

Another embodiment of the present invention includes a method for inhibiting the biological activity of a selected duplex genetic sequence. In this method, a suitable target sequence of base-pairs is selected within the selected duplex genetic sequence whose activity is to be inhibited. A polymer composition, as described above, is provided which is effective to bind in a sequence-specific manner to the target sequence. The polymer composition is contacted with the selected duplex genetic sequence under substantially physiological conditions.

This method may further include contacting the polymer composition with the selected genetic sequence where contacting the polymer composition with the selected genetic sequence entails targeting the polymer composition to a tissue or site containing the selected genetic sequence to be inactivated. Some methods of delivery include delivering the polymer composition in the form of an aerosol to the respiratory tract of a patient and/or injecting an aqueous solution of the polymer composition into a patient.

These and other objects and features of the present invention will become more fully apparent when the following detailed description of the invention is read in conjunction with the accompanying drawings.

BRIEF DESCRIPTION OF THE DRAWINGS

FIGS. 1A–1D illustrate T:A (1A), A:T (1B), C:G (1C) and G:C (1D) oriented Watson-Crick base-pairs, showing the major-groove hydrogen-binding sites of the base-pairs (arrows).

FIG. 5A–5C show representative 2'-deoxyribose (FIG. 5A), ribose (FIG. 5B), and ribose-derived backbone structures (FIG. 5C) suitable for use in forming the polymer of the invention.

FIG. 10E shows several guanine analogs that lack a hydrogen bond acceptor at the 7 position.

FIG. 11A and 11B show hydrogen bonding of a cytosine base to a G:C (FIG. 11A) and T:A (FIG. 11B) oriented base-pair.

FIGS. 12A and 12B show hydrogen bonding of a uracil base to an A:T (FIG. 12A) and C:G (FIG. 12B) oriented base-pair.

FIG. 37 illustrates a segment of a polymer constructed according to the invention, and designed to bind to a region of an A-form RNA/RNA duplex having the sequence of base-pairs: C:G, A:U, U:A, and G:C.

FIG. 38 illustrates a segment of a polymer constructed according to the invention, and designed to bind to a segment of duplex DNA in the B conformation in the transcriptional control region of a transcriptionally-active gene, with that duplex target sequence having the sequence of base-pairs: T:A, G:5mC, 5mC:G, and A:T.

DETAILED DESCRIPTION OF THE INVENTION

I. Polymer Subunit Construction

Figure 2A:
FIGS. 2A and 2B illustrate tautomeric forms of 2-amino pyrimidine (2A), and 2-pyrimidinone (2B)

The polymer of the invention is designed for binding with base-pair specificity to a selected sequence (the target sequence) in a strand of duplex nucleic acid. As used herein, duplex sequence refers to a sequence of contiguous oriented Watson/Crick base-pairs, where the four oriented base-pairs are: A:T (or A:U), T:A (or U:A), G:C, and C:G, where A, T, U, G, and C, refer to adenine, thymine, uracil, guanine, and cytosine nucleic acid bases, respectively.

The polymer is formed of subunits, each of which comprises a backbone structure and linkage group, which collectively form an uncharged backbone, and a base attached to the backbone structure, which provides base-pair-specific hydrogen-bonding to the target. The requirements of the backbone structure, linkage group, and attached base in the polymer subunits are described in detail below.

In the context of the duplex binding polymers of the present invention, the term "base" refers to planar base-pair-specific hydrogen-bonding moieties.

A. Subunit Base Requirements

Because of the symmetry of the polar minor-groove sites and the asymmetry of polar major-groove sites in Watson/Crick base-pairs, to achieve a given level of sequence specificity a minor-groove-binding agent would have to recognize twice as many base-pairs as would a corresponding major-groove-binding agent. Accordingly, hydrogen-bonding of the subunit base is to the polar sites in the major groove of the target duplex.

FIGS. 1A–1D shows T:A, A:T, C:G, and G:C oriented Watson/Crick base-pairs, with the major-groove hydrogen-bonding sites indicated by arrows in the figure. For the T:A and A:T oriented base-pairs, the polar major-groove sites include the N7 and a hydrogen on the N6 of adenine and the 04 of thymine (or uracil). For the C:G and G:C oriented base-pairs, the polar major-groove sites include the 06 and N7 of guanine and a hydrogen on the N4 of cytosine.

In order to make a significant contribution to the free energy of binding and to provide adequate base-pair specificity, the subunit base should form at least two hydrogen bonds to its target base-pair. That is, each subunit base in the polymer should contain at physiological pH a hydrogen-bonding array suitable for binding to two or three of the polar major-groove sites on its respective oriented target base-pair. Table 1 shows the hydrogen-bonding arrays comprising the polar major-groove sites for each of the four oriented Watson/Crick base-pairs, and the corresponding hydrogen-bonding array of the subunit base suitable for hydrogen-bonding to said polar major-groove sites.

In the table, X is generally an N, O, or S atom, but can also be F, Cl, or Br, having a non-bonded pair of electrons suitable for hydrogen bonding, and ** represents the nonbonded pair of electrons suitable for hydrogen-bonding.

TABLE 1

| Oriented base-pair | hydrogen-bonding array of base-pair | | | Required hydrogen-bonding array of subunit base | | | | | |
|---|---|---|---|---|---|---|---|---|---|
| A:T | ** | H | ** | N | X | or | N | X | N |
|  |  |  |  | H | ** |  | H | ** | H |
| T:A | ** | H | ** | X | N | or | N | X | N |
|  |  |  |  | ** | H |  | H | ** | H |
| C:G | H | ** | ** | N | N | or | X | N | N |
|  |  |  |  | H | H |  | ** | H | H |
| G:C | ** | ** | H | N | N | or | N | N | X |
|  |  |  |  | H | H |  | H | H | ** |

As indicated above, the polymer subunit base typically contains the specified hydrogen-bonding array at physiological pH (in contrast to cytosine moieties used for Hoogsteen-type major-groove binding). This assures that at physiological pH, binding of the subunit base makes a substantial contribution to the free energy of binding between the polymer and its target duplex.

At physiological pH the subunit base should be predominantly non-ionized. More specifically, basic moieties should have pKb values of at least 7.5 or greater, and acidic moieties should have pKa values of at least 7.7 or greater. This lack of substantial ionic charge provides two advantages. First, for applications in living cells, the lack of ionic groups on the binding polymers facilitates passage of the polymer across biological membranes. Second, lack of negative charges avoids the problem of charge repulsion between the binding polymer and the negatively charged phosphates of its target duplex.

Major-groove hydrogen-bonding arrays of the four oriented Watson/Crick base-pairs are illustrated in Table 2.

In Table 2, H is a hydrogen bound to a nitrogen, and ** is an electron pair of nitrogen or oxygen available for hydrogen bonding.

TABLE 2

|       | NH4 | O6 | N7 |        | N7 | O6 | NH4 |
|-------|-----|----|----|--------|----|----|-----|
| C:G   | H   | ** | ** | G:C    | ** | ** | H   |
| A:T(U)| **  | H  | ** | T(U):A | ** | H  | **  |
|       | N7  | NH6| O4 |        | O4 | NH6| N7  |

The respective positioning of the base-pair H-bonding arrays shown in Table 2, which approximates their relative positions in the major-groove of a duplex genetic sequence, illustrates the fact that two of the H-bonding sites of a C:G base-pair (NH4 and O6) are positioned nearly the same as two of the H-bonding sites of an A:T(U) base-pair (NH6 and O4). Likewise, two of the hydrogen-bonding sites of a G:C base-pair (O6 and NH4) are positioned nearly the same as two of the H-bonding sites of a T(U):A base-pair (O4 and NH6). Because of these similarities in positioning between central hydrogen-bonding sites of the oriented base-pairs, subunit bases which hydrogen-bond only to the polar sites near the center of the major-groove (underlined in the above table) lack adequate specificity for a given base-pair. Accordingly, in order for a subunit base to achieve high specificity for a single oriented base-pair, the base should hydrogen bond to the N7 of its respective target base-pair.

Figure 2B:
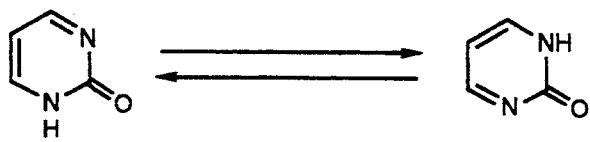

If a subunit base is targeted to bind only one of the four oriented Watson/Crick base-pairs, the tautomeric state of that subunit base should be sufficiently fixed under conditions of use so that at least two of the hydrogen-bonding groups positioned for base-pair binding will not tautomerize to give a structure capable of H-bonding with comparable affinity to a base-pair other than the targeted base-pair To illustrate, FIG. 2A shows an acceptably fixed structure (2-amino pyrimidine, which exists almost exclusively in the 2-amino tautomeric form). FIG. 2B shows a second structure which lacks specificity for a single base-pair due to its facile tautomerization under physiological conditions (2-pyrimidinone). Dominant tautomeric forms of a wide assortment of representative heterocyclic structures have been tabulated in a book edited by Elguero, Marzin, Katritzky & Linda (1976).

Figure 2C:
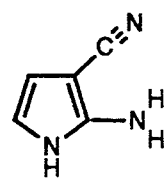
FIGS. 2C and 2D illustrate rigid (2C) and non-rigid (2D) hydrogen-bonding arrays.
Figure 2D:
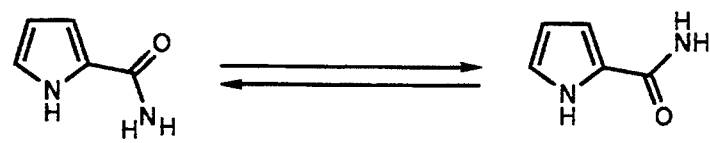

The subunit bases typically have structures which provide a relatively rigid arrangement of at least two of the base-pair H-bonding groups positioned for base-pair binding. Such rigidity is best afforded by a ring structure wherein at least two of the polar hetero atoms to be involved in H-bonding to the target base-pair are either part of the ring or directly attached to the ring. To illustrate, FIG. 2C shows a structure (2-amino-3-cyano pyrrole) which satisfies this rigidity requirement. FIG. 2D shows a structure (2-carboxamide pyrrole) which fails to satisfy the requirement.

The simplest sequence-specific binding polymers are those which bind to a target which is composed of contiguous base-pairs in the polynucleotide duplex. This, in turn, requires that the subunit bases of the binding polymer be no thicker than the target base-pairs to which they are to bind. Accordingly, each subunit structure should be planar. This is best achieved by using subunit bases having aromatic character and/or having plane trigonal bonding for most or all ring atoms.

B. Constraints on the Position and Angle of Attachment of the Base to the Backbone Considering now the geometric requirements of the polymer subunits, most duplex nucleic acids adopt either of two general conformations. RNA/RNA and RNA/DNA duplexes adopt an A-type conformation. DNA/DNA duplexes adopt a B-type conformation, but can readily convert to an A conformation under certain conditions, such as high salt or low polarity solvent.

In duplex nucleic acids the polar major-groove sites on each of the Watson/Crick base-pairs are fairly regularly positioned with respect to corresponding arrays of major-groove sites on neighboring base-pairs, with the relative positions being defined by the helical conformation parameters of axial position, axial rise, and axial rotation.

In principle, the backbone attachment positions of the different subunit bases, when the bases are hydrogen-bonded to their respective target base-pairs, need not be positioned in any regular way relative to their target base-pairs. However, when there is significant variability in the relative backbone attachment positions of the different subunit bases relative to their target base-pairs, each of the backbone structures of the component subunits in the polymer are custom tailored with respect to backbone length and position of subunit base attachment, leading to extremely high development and production costs.

However, if all of the subunit bases of a given subunit set have similar backbone attachment positions and angles relative to their respective target base-pairs, then all subunits of the set can have identical backbone structures, greatly simplifying the synthetic effort required for polymer construction. To this end, the polymer subunits used in the present invention are selected, according to criteria described below, to have similar backbone attachment positions and angles.

Figure 3A:
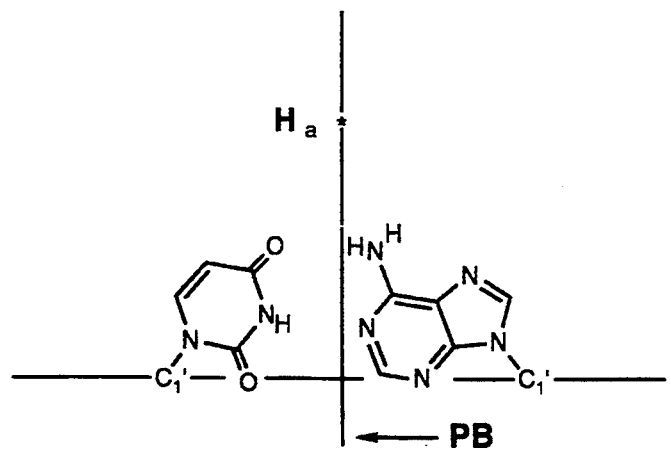
FIG. 3A–3D illustrate standard positioning for a U:A base-pair in an A conformation and the approximate position of helical axis for an A-form duplex (FIG. 3A), the use of this positioning scheme for assessing $R_a$, $\Theta_a$, and A values for a subunit base hydrogen bonded to the polar major-groove sites of a U:A base-pair in an A conformation (FIG. 3B), the standard positioning for a T:A base-pair in a B conformation and the approximate position of helical axis for a B-form duplex (FIG. 3C), and the use of this positioning scheme for assessing $R_b$, $\Theta_b$, and A values for a subunit base hydrogen bonded to the polar major-groove sites of a T:A base-pair in a B conformation (FIG. 3D).

To understand what is meant by similar backbone attachment positions and angles, reference is made to FIG. 3A, which shows a Watson/Crick base-pair (W/C bp) positioned relative to the helical axis (denoted $H_a$) of an A-form genetic duplex, i.e., (A, 12, 0.326) RNA. The lower horizontal line in the figure connects the two ribose C1' atoms of the Watson-Crick base-pair, and the vertical line (denoted PB) is the perpendicular bisector of the first-mentioned line.

Figure 3B:
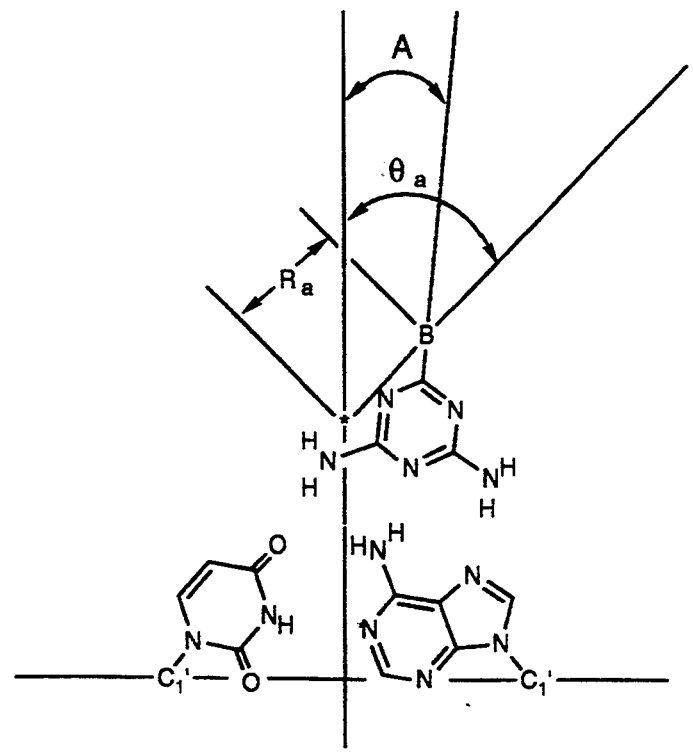

The backbone attachment position and angles of a subunit base are then determined by positioning the subunit base on its corresponding target base-pair in this standardized position, with the subunit base being hydrogen bonded to the appropriate polar major-groove sites on the Watson-Crick base-pair, as shown for a 2,6-diaminotriazine subunit base in FIG. 3B.

The backbone attachment position of the subunit base, relative to its A-form target duplex, can then be described by an $R_a$ and $\Theta_a$ value, where $R_a$ is the radial distance, in angstroms, from the helical axis of the A-form target duplex to the center of the backbone atom (denoted B; FIG. 3B) to which the subunit base is attached, and $\Theta_a$ is the angle, in degrees, about this helical axis, measured clockwise from the perpendicular bisector to the center of the aforementioned backbone atom. The attachment angle, A, is defined as the angle, in degrees, measured clockwise from the perpendicular bisector, between the perpendicular bisector and a line parallel to the bond between the subunit base and the backbone moiety.

Figure 3C:
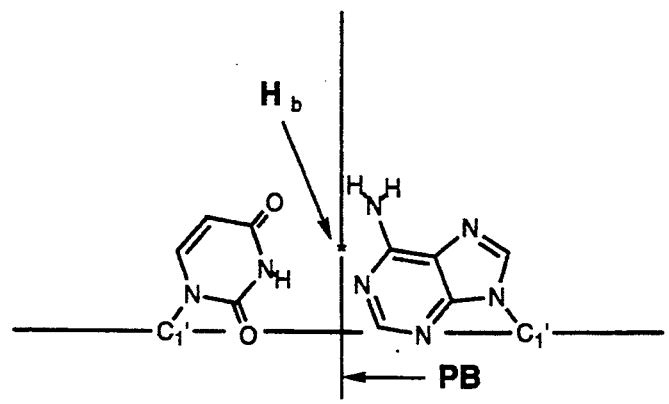
Figure 3D:
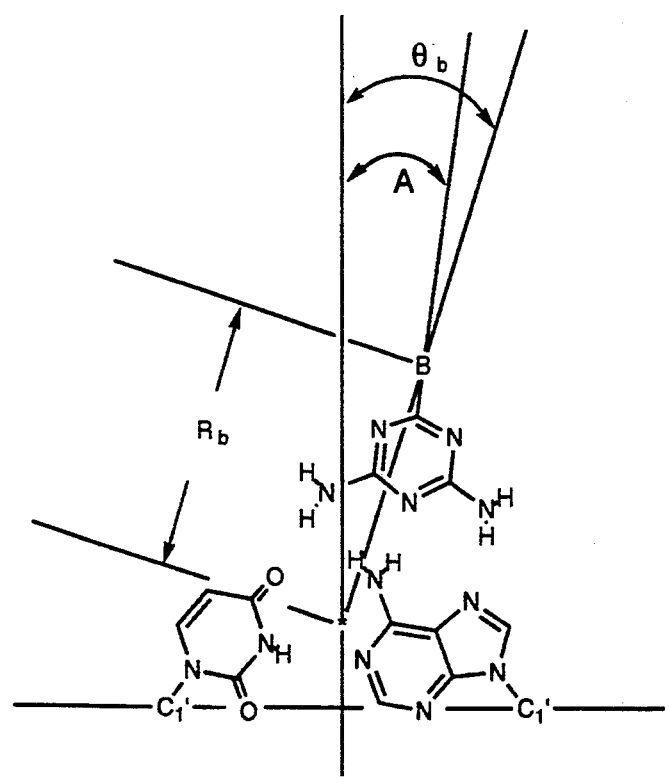

FIG. 3B illustrates $R_a$, $\Theta_a$, and A parameters for a 2,6-diaminotriazine subunit base hydrogen-bonded to a U:A base-pair in an A conformation. FIG. 3C illustrates a correspondingly positioned base-pair of a B-form duplex, and FIG. 3D illustrates $R_b$, $\Theta_b$, and A parameters for this 2,6-diaminotriazine subunit base hydrogen-bonded to a T:A base-pair in a B conformation.

In order to unambiguously define the target base-pair for a selected subunit base with a given backbone attachment site, two orientations for each Watson/Crick base-pair in the target duplex must be considered. The resultant 4 oriented base-pairs are designated as A:T, T:A, C:G, and G:C (and corresponding base-pairs where U replaces T). The orientations of these base-pairs are defined in Table 3.

TABLE 3

| Oriented Base-pair Designation | $\Theta$ value for N7 of Purine of Target Base-pair |
|---|---|
| A:T (A:U) | >180° |
| T:A (U:A) | <180° |
| C:G | <180° |
| G:C | >180° |

In principle, the backbone attachment position for any given subunit base, in position on its target base-pair, can have a $\Theta$ value, , X°, in the range of 0° to 180°. By flipping the target base-pair, the $\Theta$ value of that same target-bound subunit base is changed to 360°−X°. The convention used in the following discussion is that the $\Theta$ value for each subunit base of the binding polymer is less than 180°.

Thus, in the context of selecting a subunit set suitable for assembling the binding polymers disclosed herein, to explicitly define which orientation of a given base-pair constitutes the target for a specified subunit base, it is important to designate the orientation of that target base-pair such that the backbone attachment position of the base-pair-bound subunit base has a $\Theta$ value less than 180°. To illustrate, a 2,6-diaminotriazine subunit base having a backbone moiety attached through the C4 of the triazine (FIG. 3B) can bind to a U:A base-pair in an A conformation to give a $\Theta$ value of 28°. When this same subunit base is hydrogen-bonded to that same base-pair in the base-pair's opposite orientation (ie., A:U), the $\Theta$ value for the subunit base is 332° (ie., 360°−28°). The convention used herein dictates that the target base-pair for this subunit base is U:A (where $\Theta$ is <180°), and not A:U (where $\Theta$ is >180°).

Acceptable values of R, $\Theta$, and A for prospective recognition moieties can be readily obtained with CPK molecular models (The Ealing Corp., South Natick, Mass., USA). More accurate values can be estimated by optimization of the hydrogen-bonding in the subunit base/base-pair triplex via a computer molecular mechanics program, such as are available commercially. The subunit bases should be so selected that a given subunit set (the set of subunits used in assembly of a given polymer) all have R values within about 2 angstroms of each other, $\Theta$ values within about 20° of each other, and A values within about 30° of each other.

In order for a subunit base to have a high specificity for only one of the oriented base-pairs, it is important that the subunit base not be able to bind to a given base-pair in both orientations (e.g., G:C and C:G) simply by rotation of the subunit base about its linkage to its backbone structure. Therefore, the earlier-described backbone attachment position or angle should be asymmetrical with respect to the C1' positions of the target base-pair. Specifically, $\Theta_a$ for the subunit base should have a value greater than about 10°, or the attachment angle, A, for the subunit base should have a value greater than about 25°.

C. Bases Suitable for Binding Discrimination on the Basis of the Moiety at the 5 Position of the Pyrimidine of the Target Base-Pair Subunits have been devised which can be used to prepare a polymer which is capable of binding its duplex target genetic sequence when said sequence contains a hydrogen at the 5 position of the pyrimidine of several specified base-pairs, but which is not capable of binding a corresponding duplex target genetic sequence when said sequence contains a methyl at the 5 position of the pyrimidine of said specified base-pairs.

One application of polymers having this methyl-discriminating property is the selective inactivation of duplex RNA sequences (e.g., the replicative intermediate of an RNA virus) without concomitant inactivation of a corresponding duplex DNA sequence (e.g., an identical sequence in a patient's inherent cellular DNA). Another application of such a methyl-discriminating polymer is for selective attack on a transcriptionally-active oncogene (containing clusters of CpG sequences in the transcriptional control region) in cancer cells, without concomitant attack on the corresponding transcriptionally-inactive proto-oncogene (containing clusters of 5mC:G sequences in the transcriptional control region) in normal cells.

The essential characteristic of these methyl-discriminating bases is that they contain a special discriminating moiety which is of the proper size and shape and is so positioned that when the base is hydrogen bonded to its target base-pair the discriminating moiety occupies a portion of that space which would be occupied by a methyl at the 5 position of the pyrimidine of the target base-pair, but does not occupy that space which is occupied by a hydrogen at the 5 position of the pyrimidine of the target base-pair. As a consequence, such a methyl-discriminating base exhibits normal binding affinity for its non-methylated target base-pair, but because of steric exclusion it exhibits substantially reduced binding affinity for its corresponding target base-pair containing a methyl at the 5 position of the pyrimidine.

Figure 4A:
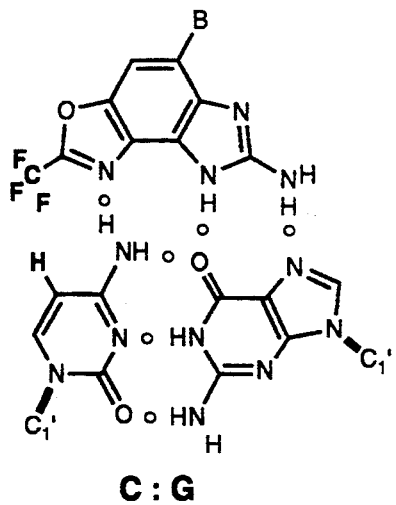
FIGS. 4A and 4B illustrates the normal binding (FIG. 4A) and substantially reduced binding (FIG. 4B) afforded by a representative methyl-discriminating base.
Figure 4B:
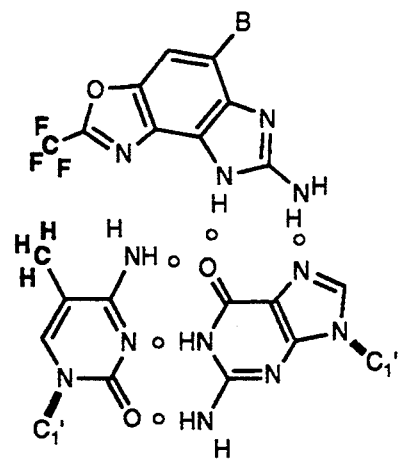
Figure 4C:
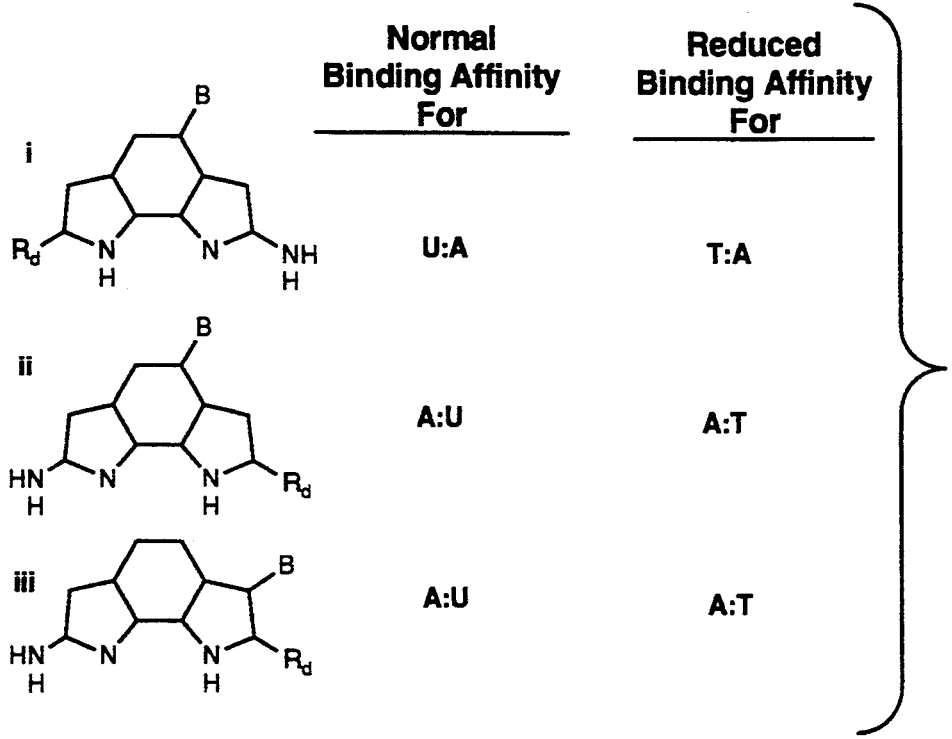
FIG. 4C illustrates the general skeletal ring structure, hydrogen bonding array, and position of the methyl-discriminating moiety of preferred bases designed to bind their respective target base-pairs having a hydrogen at the 5 position of the pyrimidine, but not bind their respective target base-pairs when said base-pairs have a methyl at the 5 position of the pyrimidine.

FIG. 4 illustrates such methyl-discriminatory binding. FIG. 4A shows the normal binding of such a base to its non-methylated target base-pair (C:G), and FIG. 4B shows the substantial disruption of binding of the same base to its corresponding methylated target base-pair (5mC:G). FIG. 4C illustrates the general skeletal ring structure, hydrogen bonding array, backbone attachment position, and position of the methyl-discriminating moiety, $R_d$, of preferred bases designed to bind their respective target base-pairs having a hydrogen at the 5 position of the pyrimidine, and designed not to bind their respective target base-pairs when said base-pairs have a methyl at the 5 position of the pyrimidine.

In regard to the 5-6-5 fused-ring bases (Structures i through vi of FIG. 4C), in order to effectively restrict binding to their respective methylated target base-pairs, the $R_d$ moiety should be larger than a hydrogen, oxygen, or fluorine. When $R_d$ in these bases is a methyl it affords only a modest reduction in binding affinity of the bases for their methylated target base-pairs. Larger moieties, such as sulfur, chlorine, bromine, cyano, azido, and similar sized moieties, provide a greater disruption of binding to a methylated target base-pair, while still affording effective binding to the corresponding non-methylated base-pair. Even better binding discrimination is afforded by difluoromethyl and trifluoromethyl moieties, which still afford effective binding to the corresponding non-methylated base-pairs. In this regard, the difluoromethyl moiety is preferred when the backbone linkage is on the ring containing the $R_d$ moiety, as in structures iii and vi of FIG. 4C, and the trifluoromethyl moiety is preferred when the backbone linkage is not on the ring containing the $R_d$ moiety, as in structures i, ii, iv, and v of FIG. 4C.

While still larger $R_d$ moieties, such as isopropyl, t-butyl, dichloromethyl, and trichloromethyl, can also afford methyl-discriminatory binding, nevertheless, they are undesirable because they also interfer with effective stacking of contiguous bases of the polymer when said polymer is in position on its duplex target sequence.

In regard to the 6-5-5 fused-ring bases (Structures vii and viii of FIG. 4C), in order to effectively restrict binding to their respective methylated base-pairs, the $R_d$ moiety should be larger than a hydrogen. When the methyl-discriminating moiety is oxygen, fluorine, or a methyl it affords substantial reduction of binding to the methylated target base-pair, while still affording good binding affinity to the non-methylated target base-pair. Larger $R_d$ moieties on the 6-5-5 type bases are undesirable because they tend to compromise binding to the non-methylated target base-pairs.

Other $R_d$ moieties can be selected to afford methyl-discriminatory binding for the above described bases. Selection of these moieties can be based on the guidance presented above and other structure-function relationship analyses (e.g., Dehlinger, 1992).

D. Backbone Structure Constraints

This section considers the backbone structure constraints for a selected subunit set. Principally, the subunit should be joinable in any selected order to other subunit structures via uncharged linkages having the general properties discussed in Section E below ("Intersubunit Linkages"). Further, the subunit backbone structures and linkages must provide proper spacing and allow correct orientation and positioning of their respective subunit bases for effective binding of the subunit bases to their respective oriented base-pairs in the target duplex sequence.

A principal requirement for the subunit backbone structure and linkage is that it provide a means for joining the subunits in essentially any specified order. This requirement can be satisfied by structures containing either heterologous or homologous linking groups. Heterologous type backbone moieties contain a nucleophilic group (N) on one end and an electrophilic group (E) on the other end, as illustrated below:

N—E

The preferred functional groups for the N component include primary and secondary amine, hydrazine, hydroxyl, sulfhydryl, and hydroxylamine. The preferred functional groups for the E component include the following acids and derivatives thereof: carboxylic, thiocarboxylic, phosphoric, thiophosphoric, esters, thioesters, and amides of phosphoric and thiophosphoric, phosphonic and thiophosphonic, and sulfonic acid. Other suitable E groups include aldehyde, dialdehyde (or vicinal hydroxyls suitable for conversion to a dialdehyde), alkyl halide, and alkyl tosylate.

Homologous type backbone moieties can be of two types, one type having nucleophilic end groups and the other type having electrophilic end groups; or, a single homologous backbone moiety can be alternated with an appropriate linker. These alternatives are illustrated below:

N—N alternated with E—E

N—N alternated with E linker

N linker alternated with E—E

Preferred functional groups for N and E are as in the heterologous backbone moieties. Preferred E linkers include carbonyl; thiocarbonyl; alkyl, ester, thioester, and amide of phosphoryl and thiophosphoryl; phosphonyl and thiophosphonyl; sulfonyl; and, oxalic acid. A preferred N linker is 1,2-Dimethylhydrazine.

The present invention contemplates a variety of both cyclic and acyclic backbone structures, as will be illustrated in FIGS. 5-9 below. One limitation of acyclic backbone structures is that activation of the electrophilic linking groups preparatory to polymer assembly, can lead to varying amounts of undesired intramolecular attack on sites of the subunit base. By contrast, with properly structured cyclic backbone moieties, the activated electrophile can be effectively isolated from reactive sites on the subunit base, thereby reducing unwanted intramolecular reactions.

However, use of aliphatic cyclic backbone moieties does entail the presence of multiple chiral centers in each backbone structure. With proper selection of cyclic backbone structures, synthetic challenges associated with such multiple chiral centers can be largely circumvented, by utilizing readily available natural products for the backbone moiety or, preferably, for the entire subunit, or as a proximal precursor thereto.

This preference for backbone structures, or entire subunits, from natural sources reflects the difficulty, and corresponding greater expense, of de novo preparation of aliphatic ring structures having multiple chiral centers. Accordingly, preferred categories of cyclic backbone moieties are those comprising, or readily derived from, deoxyribose or ribose. In addition, certain other natural cyclic structures wherein a single enantiomer is available, or can be readily prepared or isolated, are also preferred. FIGS. 5A-5C illustrate exemplary cyclic backbone structures comprising or derived from deoxyribosides or ribosides. R' in FIG. 5 indicates H or alkyl, and $R_i$ indicates the subunit base, which, as seen, has the same $\beta$-orientation as natural nucleosides. FIGS. 6A-6F illustrate exemplary cyclic morpholino backbone structures derivable from ribosides, having either a $\beta$-orientation (FIGS. 6A-6C) or an $\alpha$-orientation (FIGS. 6D-6F) for the 5'-methylene (numbered as in the parent ribose), again with a $\beta$ orientation of the $R_i$ base. The synthesis of such subunits will be described below and in Examples 1-5. FIGS. 7A-7F show representative types of acyclic backbone structures.

E. Intersubunit Linkages

This section considers several types and properties of intersubunit linkages used in linking subunits to form the polymer of the invention. First, the backbone is stable in neutral aqueous conditions. Since the binding polymers are designed for use under physiological conditions it is necessary that the intersubunit linkages be stable under said conditions. The linkages are also stable under those conditions required for polymer assembly, deprotection, and purification. To illustrate this stability requirement, an alkyl sulfonate (R—(SO$_2$)—O—CH$_2$—R') is precluded because the resultant structure is unduly sensitive to nucleophilic attack on the CH$_2$. Further, while carbonates (R—O—(C=O)—O—R') and esters (R—(C=O)—O—R') can be successfully prepared, their instability under physiological conditions renders them of little practical value.

Secondly, the backbone is adaptable to a conformation suitable for target binding. If the intersubunit linkage is such that it exhibits specific rotational conformations (as is the case for amides, thioamides, ureas, thioureas, carbamates, thiocarbamates, carbazates, hydrazides, thiohydrazides, sulfonamides, sulfamides, and sulfonylhydrazides) then it is important either that the rotomer compatible with target binding be the lowest energy conformation, or that the barrier to rotation between the conformations be relatively low (ie., that the conformations be rapidly interchangeable at physiological temperatures). Thus, a secondary amide (N-alkyl amide, which prefers to adopt a trans conformation) would be acceptable if the trans conformation is suitable for pairing to the target duplex. By contrast, tertiary amides and related N,N-dialkyl structures generally have two approximately equal low energy conformations, and so to be useful in a binding polymer, the linkages should have a relatively low energy barrier to interconversion between the two conformations.

The barrier to rotation between two conformers can be assessed by NMR essentially as follows: At a temperature where the two conformers are interconverting slowly relative to the NMR time scale (on the order of 10$^{-8}$ sec) two distinct signals are often seen, each representing a single conformer. As the NMR spectra are taken at progressively higher temperatures, the two conformer signals coalesce—indicating rapid interconversion. Thus, the coalescence temperature (Tc) provides a useful measure of the rotational freedom of various linkage types. For example, N,N-dimethylformamide exhibits a Tc of about 114° C. (Bassindale, 1984) and conformers of analogous tertiary amides have been found to interconvert slowly in biological macromolecules. By contrast, experiments performed in support of the present invention demonstrate that an N,N-dialkyl carbamate-containing structure exhibits a Tc just under 44° C. indicating reasonable conformational freedom at physiological temperature.

An N,N-dialkylsulfinamide (which should have a rotational energy barrier similar to that of sulfonamide and related substances) has been reported to have a Tc lower than minus 60° C. (Tet. Let. 10 509 (1964)). Based on these considerations, backbone linkages containing N,N-dialkyl-type carbamate, thiocarbamate, carbazate, and various amidates of phosphorous and sulfur are preferred, while N,N-dialkyl-type amide, thioamide, urea, thiourea, hydrazide, and thiohydrazide linkages are generally unacceptable.

Third, the backbone should be uncharged. For therapeutic applications it is desirable to design these binding polymers so that they i) are not sequestered by the reticuloendothelial lining of the capillaries; ii) readily cross cell membranes; iii) are resistant to degradation by nucleases; and, iv) are not repelled by the high density of negative charge on the backbones of the target duplex. These design objectives are best achieved by using both intersubunit linkages and backbone moieties which are largely uncharged (non-ionic) at physiological pH.

When the subunit bases are positioned on contiguous base-pairs of their target sequence via hydrogen-bonding, and if all recognition moieties of the subunit set have well matched R, $\Theta$, and A values, then the distance from the subunit base attachment position of one backbone moiety to the attachment position of the next backbone moiety is the square root of the following formula:

$$(R\ sine(rot))^2 + (R\ cosine(rot) - R)^2 + (rise)^2$$

where R is the distance from the helical axis to the center of the atom of the backbone moiety to which the subunit base is attached, rot is the axial rotation value for the target duplex (typically about 30° to 33° for an A-form duplex and 36° for a B-form duplex), and rise is the axial rise value for the target duplex (typically about 2.8 to 3.3 A for an A-form duplex and 3.4 A for a B-form duplex). It is this distance which must be spanned by the unit backbone length of the binding polymer, i.e., the length of one backbone structure plus the intersubunit linkage between backbone structures. However, A-form (RNA/RNA and RNA/DNA duplexes) and B-form (DNA/DNA) target duplexes are both somewhat flexible. Accordingly, these duplexes can generally accommodate binding polymers which have unit backbone lengths that are a fraction of an angstrom shorter or longer than the calculated length requirement. Further, DNA/DNA in a B conformation can be converted to an A conformation under certain conditions.

In selecting a particular backbone structure, the following factors bear on the required length and so should be taken into consideration: first, any conformational restrictions imposed by hindered rotations about bonds such as amides and carbamates; second, when the subunit bases are in position on their target base-pairs, any steric interactions between these bases and the target duplex, and between the bases and the polymer backbone; third, steric interactions between different components of the backbone structure; and fourth, for cyclic backbone moieties, favored conformations of the component ring structure of the subunit backbone structures.

One way to determine whether or not a prospective polymer backbone is likely to be acceptable for use against a particular target conformation (e.g., A-form or B-form) is to assemble, with CPK molecular models, a representative target genetic duplex in the desired conformation, with subunit bases H-bonded thereto. The prospective polymer backbone is then added to the model. Criteria for the evaluation of backbone operability as a duplex binding polymer include the following: (i) the prospective polymer backbone can be easily attached without having to adopt an energetically unfavorable conformation, and (ii) the attachment of the polymer backbone does not cause significant perturbation of the target structure, and if there are no unacceptable steric interactions. Additional support for the suitability of a prospective backbone structure can be obtained by modeling the polymer/target triplex on a computer using a molecular mechanics program to obtain an optimized bonding structure via an energy minimization procedure. Such modeling can help to identify significant unfavorable interactions (e.g., dipole-dipole repulsions) that might be overlooked in the initial CPK modeling.

Figure 8A:
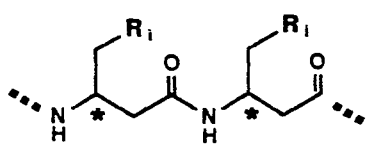
FIG. 8A shows a representative coupled acyclic backbone structure with a 4-atom unit backbone length.
Figure 8B:
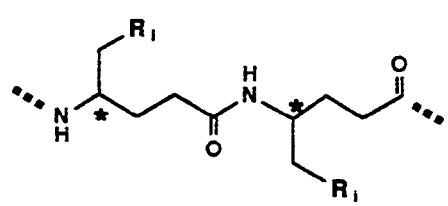
FIGS. 8B–8C show coupled acyclic backbone structures with a 5-atom unit backbone length.
Figure 8C:
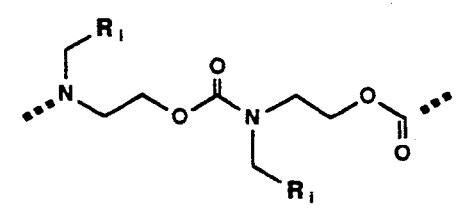

As noted above, such factors as R, Θ, and A values for the subunit bases of a given subunit set, and steric and rotational constraints of particular subunit structures and intersubunit linkages, bear on how long a unit backbone must be in order to provide the correct spacing of subunit bases for binding to a target duplex in a given conformation. However, as a rule, subunit sets wherein the subunit bases of the set have $R_a$ values less than about 7 angstroms and Θ values clustered within about 15° of each other, and A values clustered within about 30° of each other, generally require a 4-atom or 5-atom unit-length acyclic-type backbone, such as shown in FIGS. 8A–8C, or a 6-atom unit-length cyclic-type backbone, such as shown in FIG. 9A–9D, for binding to target duplexes in an A-type conformation.

Figure 8D:
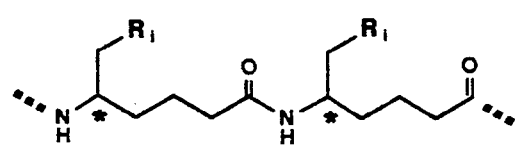
FIGS. 8D–8F show coupled acyclic backbone structures with a 6-atom unit backbone length.
Figure 8E:
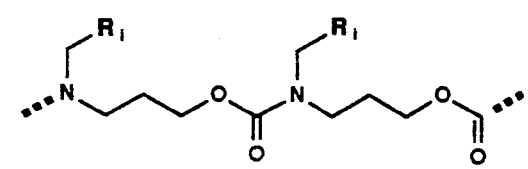
Figure 8F:
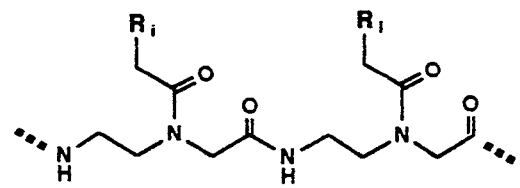
Figure 9A:
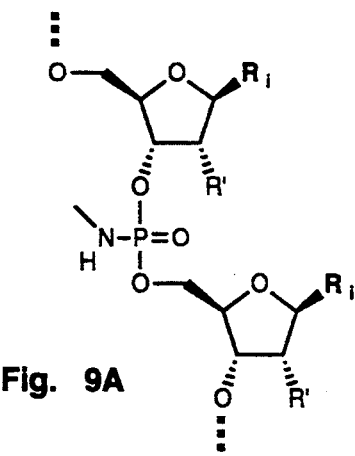
FIGS. 9A–9D show representative coupled cyclic backbone structures with a 6-atom unit backbone length.
Figure 9B:
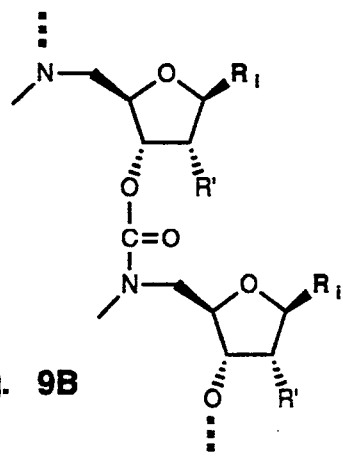
Figure 9C:
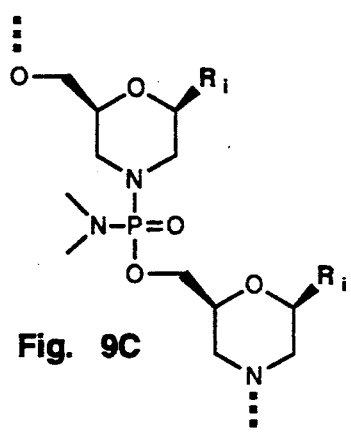
Figure 9D:
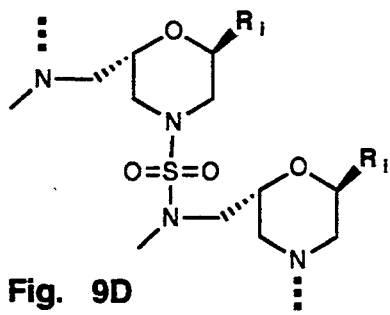
Figure 9E:
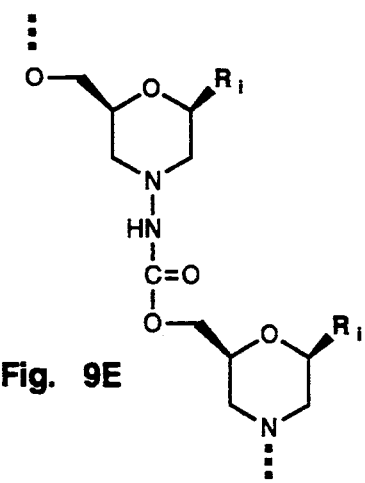
FIGS. 9E–9F show representative coupled cyclic backbone structures with a 7-atom unit backbone length.
Figure 9F:
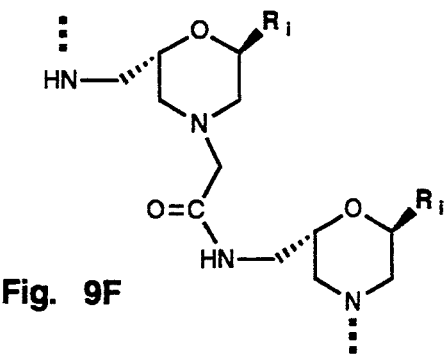

Subunit base sets having Rb values less than about 11 Angstroms, $Θ_b$ values within about 15° of each other, and A values clustered within about 30° of each other generally require a 6-atom unit-length acyclic-type backbone, such as shown in FIGS. 8D–8F, or a 7-atom unit-length cyclic-type backbone, such as shown in FIGS. 9E–9F, for binding to target duplexes in a B-type conformation.

However, it should be noted that DNA/DNA duplexes, which generally exist in a B conformation, can readily convert to an A conformation. Two such conditions which cause this B to A transition are high salt and low polarity solvent. It also appears that a B to A conformational transition of the target duplex can be induced by duplex-directed binding polymers having backbone unit-lengths shorter than optimal for binding to a B-form duplex. However, such conformation transitions incur a cost in free energy of binding, and so, to compensate, the binding polymer's affinity for its target is increased accordingly. Because of the feasibility of this B to A conformational transition of target duplexes, for some applications the shorter unit-length backbones suitable for A-form target duplexes can also be used for targeting genetic sequences which exist normally in a B conformation.

F. Subunit Sets

Subunits of a set can be assembled in any desired order for targeting a selected duplex sequence when (i) the subunit bases of a set have acceptably matched R, Θ, and A values, (ii) subunit backbone structures are identical or similar in length and (iii) identical or similar subunit base attachment positions and orientations are used for all subunits of the set.

Each subunit of such a matched set consists of a subunit base linked at a standard position to a standard-length backbone structure. The subunit base of each subunit of the set has an R, Θ, and A value closely matched to the R, Θ, and A values of the subunit bases of the other subunits of that set.

According to one feature of the present invention, the polymer subunits in a set contain at least two different subunit types, each specific for a different oriented base-pair. Specifically, the base of each of at least two different subunits of the set is effective to form at least two hydrogen bonds with the major-groove sites of its respective target base-pair, where one of those hydrogen bonds is to the purine N7 nitrogen of the target base-pair, as discussed above.

Other subunit or other subunits in the set may bind, but are not required to bind, with high specificity to oriented base-pairs in the target sequence. Thus, another subunit of the set may bind satisfactorily to two different oriented base-pairs, as will be seen below. Such low-specificity or non-specific subunits serve to provide (a) required spacing between high-specificity subunits in the polymer and (b) contribute to stacking interactions between the planar bases in the polymer/duplex complex.

In addition, the subunits in the polymer provide high-specificity base binding to at least about 70% of the oriented base-pairs in the target sequence. Thus, where a subunit set includes only two high-specificity bases, the target duplex sequence contain at least 70% oriented base-pairs which are specifically bound by those two high-specificity bases.

1. Basic Subunit Set for C:G and T:A or U:A Oriented Base-pairs. The most basic subunit set is suitable for targeting duplex genetic sequences containing only C:G and T:A or U:A oriented base-pairs.

Figure 10A:
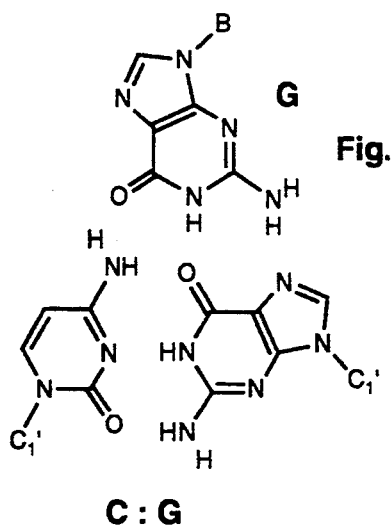
FIGS. 10A and 10B illustrate a guanine base and its binding to a C:G oriented Watson-Crick base-pair (FIG. 10A) and a diaminopurine base and its binding to a T:A oriented Watson-Crick base-pair (FIG. 10B).

The first member of this basic subunit set is a high-specificity subunit containing a guanine, 6-thioguanine, or analog thereof, subunit base effective to hydrogen bond specifically to a C:G oriented base-pair. As illustrated in FIG. 10A, guanine (or 6-thioguanine) forms three hydrogen bonds to the polar major-groove sites of a C:G oriented base-pair, including the guanine N7 of that target base-pair. The subunit may be formed with any of a variety of deoxyribose, ribose or morpholino backbone structures, with the base attached to the backbone structure in the β-stereochemical orientation, as illustrated in Example 2.

Figure 10B:
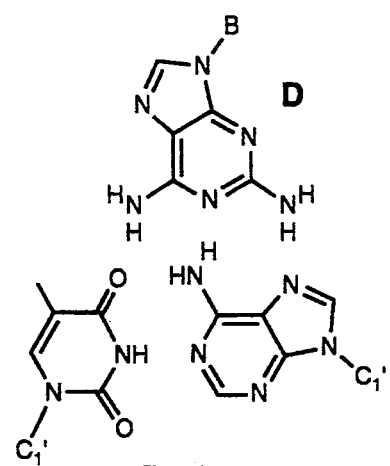

The second member of the basic set is a high-specificity subunit containing a 2,6-diaminopurine, or analog thereof, subunit base effective to hydrogen bond specifically to a T:A or U:A oriented base-pair. As illustrated in FIG. 10B, the 2,6-diaminopurine base forms three hydrogen bonds to the polar major-groove sites of a T:A or U:A oriented base-pair, including the adenine N7 of that target base-pair. As with the guanine subunits, a variety of diaminopurine subunits, and analogs thereof, with deoxyribose, ribose and morpholino backbone structures, and having the desired β-stereochemical attachment of the base to the backbone structure, can be prepared by modifications of available nucleosides, also as illustrated in Example 2.

CPK molecular modeling showed that the guanine and diaminopurine moieties should effectively and specifically bind their target base-pairs. Additional support for this major-groove hydrogen-bonding mode was obtained from a best fit analysis carried out for these two trimolecular complexes, C:G:G and U:A:D. Voet and Rich (1970) tabulate the lengths and angles of hydrogen-bonds from x-ray diffraction studies of crystalline complexes of purines and pyrimidines. In those tabulations NH:N bonds range in length from 2.75 A to 3.15 A and their angles range from 115° to 145°. NH:O bonds range in length from 2.60 A to 3.20 A and their angles range from 110° to 145°.

In the best fit calculations, structural parameters used for the purines and pyrimidines in the Watson-Crick base-pairs are those given by Rich and Seeman (1975). Those parameters were obtained from x-ray diffraction of ApU and GpC crystals (right handed anti-parallel Watson-Crick) which were solved at atomic resolution. The guanine structural parameters referenced above were also used for the subunit base in FIG. 10A. The 2,6-diaminopurine subunit base of FIG. 10B was assumed to have structural parameters essentially identical to those of 9-ethyl-2,6-diaminopurine obtained from x-ray diffraction studies of crystalline trimolecular complexes of 9-ethyl-2,6-diaminopurine hydrogen-bonded to two 1-methylthymines (one thymine bonded in the Watson-Crick mode and the other thymine bonded in the reverse-Hoogsteen mode) as reported by Sakore et al. (1969).

To simplify the analysis, the approximation was made that all atoms are in the same plane. Table 4 gives the results of this analysis. In this table the standard purine and pyrimidine numbering system is used throughout, subunit base-G stands for the subunit base of FIG. 10A (guanine) and subunit base-D for the subunit base of FIG. 10B (2,6-diaminopurine). Angles are measured as in Voet and Rich (1970).

TABLE 4

| | angle | length |
|---|---|---|
| Guanine subunit base H-bonded to a C:G base-pair | | |
| W/C hydrogen-bonds | | |
| O2(C):NH2(G) | 125° | 3.17 A |
| N3(C):NH1(G) | 119° | 2.95 A |
| NH4(C):O6(G) | 129° | 2.63 A |
| Major-Groove hydrogen-bonds | | |
| NH2(subunit base-G):N7(G) | 140° | 3.12 A |
| NH1(subunit base-G):O6(G) | 115° | 2.74 A |
| O6(subunit base-G):NH4(C) | 143° | 2.63 A |
| Diaminopurine subunit base H-bonded to a U:A base-pair | | |
| W/C hydrogen-bonds | | |
| NH3(U):N1(A) | 119° | 2.98 A |
| O4(U):NH6(A) | 126° | 2.71 A |
| Major-Groove hydrogen-bonds | | |
| NH2(subunit base-D):N7(A) | 137° | 2.85 A |
| N1(subunit base-D):NH6(A) | 139° | 2.95 A |
| NH6(subunit base-D):O4(U) | 132° | 3.00 A |

As can be seen from this table, all hydrogen-bond angles and lengths in the subunit base/base-pair complexes fall within established angle and length limits for hydrogen-bonds.

Figure 10C:
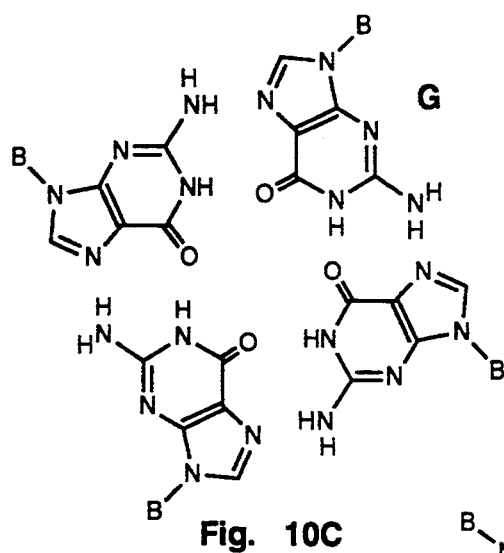
FIG. 10C shows tetramer formation with guanine bases.
Figure 10D:
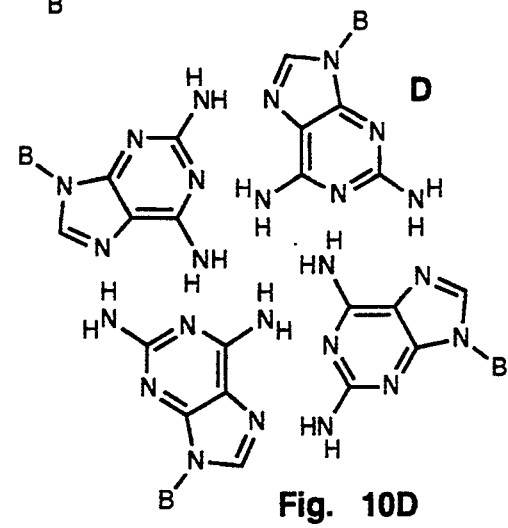
FIG. 10D shows hydrogen bonding at diaminopurine bases.

A practical difficulty one encounters with polymers consisting of all or nearly all guanine and diaminopurine bases is that in neutral aqueous solution they undergo self aggregation, which renders them less available for binding their selected duplex target sequences. This self aggregation probably involves tetramer formation wherein the guanine bases are hydrogen bonded by the mode illustrated in FIG. 10C, and the diaminopurine bases may be hydrogen bonded by the mode illustrated in FIG. 10D.

This self aggregation problem can be alleviated by replacing some of the guanine and/or diaminopurine bases (preferably at least 20%) with guanine and/or diaminopurine analogs which do not have a hydrogen bond acceptor site at the 7 position. This can be achieved in a variety of ways, including the use of a carbon (as in 7-deazaguanine-containing subunits; Seela 1981; Winkeler 1983) or a methylated nitrogen at the 7 position of the guanine and/or diaminopurine base. Several preferred guanine analogs which lack a hydrogen bond acceptor site at the 7 position are shown in FIG. 10E. Related diaminopurine analogs also serve to prevent self aggregation.

2. Spacer Subunits for A:T and G:C Oriented Basepairs. The basic "guanine plus diaminopurine" subunit set can be easily prepared from guanosine, or deoxyguanosine, and from analogs thereof lacking a hydrogen bond acceptor site at the 7 position, such as 7-deazaguanosine. However, binding polymers assembled from only these two subunits, and targeted against sequences of at least 16 contiguous base-pairs, are expected to have targets in only large viruses having genome sizes on the order of 65,000 base-pairs or greater.

However, it is desirable to have binding polymers which can be targeted against a much broader range of viruses, including even small viruses, such as Hepatitis B which has a genome size of only 3,200 base-pairs. One effective approach to extending the targeting range of these binding polymers is to target sequences composed predominantly (at least about 70%) of target base-pairs for the guanine and diaminopurine (and analogs thereof) high-specificity subunit bases (ie., oriented base-pairs C:G and T:A or U:A). The remaining base-pairs in the target sequence (i.e., no more than about 30% G:C and/or A:T or A:U) can then be accommodated by low-specificity "spacer" bases in the binding polymer, which serve primarily to provide continuity of stacking interactions between the contiguous subunit bases of the binding polymer when that polymer is in position on its target duplex.

Thus, in one embodiment, a polymer assembled from the basic subunit set, described in Section F1, additionally includes one or more low-specificity spacer subunit bases.

When the binding polymer is in position on its target duplex, with the subunit bases stacked, the spacer subunit bases (which are not necessarily hydrogen-bonded to their respective base-pairs) should have R, Θ, and A values which can closely match the R, Θ, and A values of the high-specificity subunit bases. Specifically, for the full subunit set, the R values should all be within about 2 Å, Θ values should all be within about 20°, and A values should all be within about 30°. Preferably, the spacer subunit bases should also provide modest hydrogen-bonding to their respective target base-pairs so as to make some contribution to target binding specificity and affinity.

Where the target sequence contains a G:C oriented base-pair, one preferred spacer subunit in the subunit set contains a cytosine base, which can hydrogen-bond weakly to G:C and to T:A oriented base-pairs. FIG. 11A shows cytosine hydrogen bonded to the major-groove sites of a G:C base-pair, and FIG. 11B shows cytosine hydrogen bonded to a T:A base-pair. In neither case does this include a hydrogen bond to the N7 of the purine of a target base-pair.

Where the target sequence contains an A:T or A:U oriented base-pair, one preferred spacer subunit in the subunit set contains a uracil (or thymine) base, which can hydrogen-bond weakly to A:T and to C:G oriented base-pairs. FIG. 12A shows uracil hydrogen bonded to the major-groove sites of an A:T base-pair, and FIG. 12B shows uracil hydrogen bonded to a C:G base-pair. As with the cytosine spacer, neither of these hydrogen bonding interactions involve the N7 of the purine of a target base-pair.

Although these two subunit spacer bases provide only low-specificity and low affinity binding to their target base-pairs, nonetheless: i) they effectively provide for continuity of subunit base stacking in the target-bound binding polymer; ii) they have R, Θ, and A values which are acceptably matched with the R, Θ, and A values of the high-specificity guanine and diaminopurine subunit bases of the subunit set; and iii) the spacer subunits, or close precursors thereto, are commercially available and relatively inexpensive.

Syntheses of subunit sets containing the four subunit bases guanine, diaminopurine, cytosine, and uracil (or thymine), and having various deoxyribose, ribose and morpholino backbone structures, are described in Example 2. The sets described in the example have the following backbone structures:
A. 2'-deoxyribose, seen in FIG. 5A, Example 2A;
B. 2'-O-methylribose, seen in FIG. 5B (R=methyl), Example 2B;
C. morpholino, seen in FIG. 6A, Example 2C;
D. N-carboxymethylmorpholino-5'-amino, seen in FIG. 6C, Example 2D;
E. N-carboxymethylmorpholino-(alpha)5'-amino, seen generally in FIG. 6F, Example 2E;
F. ribose with 5'carbazate, seen in FIG. 5C, Example 2F;
G. ribose with 5'sulfonylhydrazide, seen in FIG. 5C, but where the carbonyl group is replaced by a sulfonyl group, Example 2G;
H. ribose with 5'glycinamide, seen in FIG. 5C, but where the OCONHNH$_2$ group is replaced by NHCOCH$_2$NH$_2$, Example 2H; and,
I. ribose with 5'(aminomethyl)(ethyl)phosphate, seen in FIG. 5C, but where the OCONHNH$_2$ group is replaced by OPO$_2$EtCH$_2$NH$_2$, Example 2I.

Table 5 shows the base-pair specificities and approximate R, Θ, and A values for the subunit bases of this guanine, diaminopurine, cytosine, and uracil (or thymine) subunit set.

TABLE 5

| Subunit Base | Base-pair Specificity | $R_a$ | $\Theta_a$ | A |
|---|---|---|---|---|
| G | C:G | 5.8 A | 33° | 60° |
| D | T:A | 5.6 A | 32° | 60° |
| C | G:C & T:A | 4.8 A | 38° | 50° |
| U | A:T & C:G | 4.8 A | 38° | 50° |

Binding polymers prepared with the above G, D, C and U or T subunit set also have the potential to bind to single-stranded genetic sequences. Specifically, the polymer will be able to bind in a Watson/Crick pairing mode to a single-stranded polynucleotide of the appropriate base sequence.

Since the spacer subunits, C and U or T, in the polymer are degenerate in binding specificity, at least two of these low-specificity spacer subunits are required to provide a level of target specificity equivalent to that provided by one high-specificity subunit. Thus, a binding polymer containing 16 high-specificity subunit bases provides about the same level of target specificity as a binding polymer containing 12 high-specificity subunit bases and 8 low-specificity spacer subunit bases.

Figure 13A:
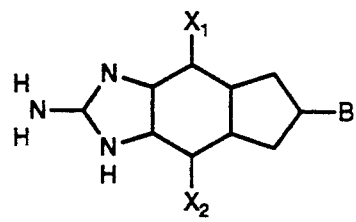
FIGS. 13A–13D illustrate the general skeletal ring structure, hydrogen bonding array, and backbone attachment position of a tautomeric base designed for binding to a G:C or A:T Watson-Crick base-pair (FIG. 13A), and three specific embodiments of the 13A structure (FIGS. 13B–13D).
Figure 13B:
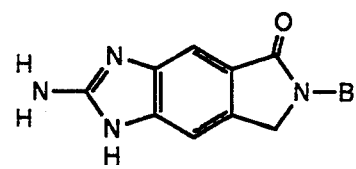
Figure 13C:
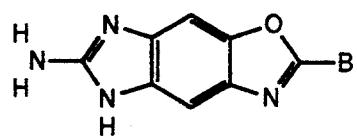
Figure 13D:
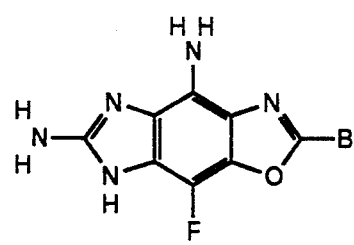

3. Subunit Set with a Tautomeric Subunit Specific for A:T and G:C Oriented Base-pairs. In another embodiment, the "guanine plus diaminopurine" subunit set described in Section F1 includes an additional subunit having a tautomeric subunit base capable of hydrogen bonding to either G:C or A:T oriented base-pairs. A generalized skeletal ring structure and hydrogen bonding array of one preferred base type is shown in FIG. 13A, where X$_1$ is H or NH$_2$; X$_2$ is H, F, or C; and B indicates the polymer backbone. FIGS. 13B–13D show three preferred embodiments of this tautomeric base, as discussed further below.

Figure 14A:
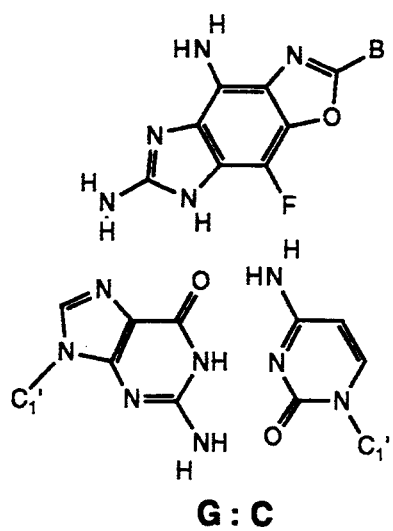
FIGS. 14A and 14B show the hydrogen bonding of the FIG. 13B structure to a G:C (FIG. 14A) and A:T (FIG. 14B) oriented base-pair.
Figure 14B:
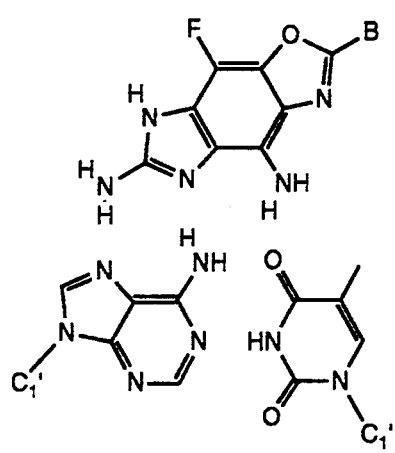

The hydrogen bonding to target base-pairs by different tautomeric forms of the base from FIG. 13D is shown in FIGS. 14A and 14B for G:C and A:T oriented base-pairs, respectively. As seen from FIG. 14, X$_2$ can be hydrogen-bond acceptor when the tautomer is hydrogen bonded to a G:C base-pair, to provide three hydrogen bonds to the base-pair. Similarly, X$_1$ can be a hydrogen-bond donor when the tautomer is hydrogen bonded to an A:T base-pair, to provide three hydrogen bonds to the base-pair.

Table 6 shows the base-pair specificities and approximate R, Θ, and A values for the subunit bases of the guanine, diaminopurine, and the subunit base of FIG. 14:

TABLE 6

| Subunit Base | Base-pair Specificity | $R_a$ | $\Theta_a$ | A |
|---|---|---|---|---|
| G | C:G | 5.8 A | 33° | 60° |
| D | T:A | 5.6 A | 32° | 60° |
| Tautomeric Base of FIG. 13B | G:C & A:T | 6.3 A | 36° | 55° |

The syntheses of a number of specific embodiments of a tautomeric subunit are described in Example 3. The synthesis of the structures seen in FIG. 13B and 13C are described in Example 3A for the 2'doexyribose backbone structure; in Example 3B for the 2'O-methylribose backbone; and in Example 3C for the morpholino backbone.

4. Subunit Set with High-Specificity Subunits for A:T and G:C Oriented Base-pairs. In another embodiment, the "guanine plus diaminopurine" subunit set described in Section F-1 includes an additional subunit whose base is specific for hydrogen bonding to a G:C oriented base-pair, or an additional subunit whose base is specific for hydrogen bonding to an A:T (or A:U) oriented base-pair, or the set includes two additional subunits whose bases are specific for hydrogen bonding to a G:C oriented base-pair and to an A:T or A:U oriented base-pair, respectively.

Figure 15A:
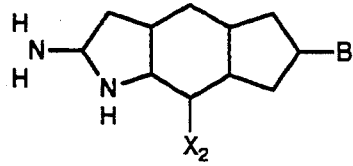
FIGS. 15A–15D illustrate the general skeletal ring-structure, hydrogen bonding array, and backbone attachment position of a base designed for binding to a G:C Watson-Crick base-pair (FIG. 15A), and three specific embodiments of the FIG. 15A structure (FIGS. 15B–15D).

FIG. 15A shows the skeletal ring structure and hydrogen bonding array of a general type of base effective to bind a G:C oriented base-pair. Three preferred embodiments of this structure type are shown FIGS. 15B–15D. FIG. 16 shows the structure in FIG. 15D hydrogen-bonded to its G:C target base-pair. As seen from FIG. 15A and FIG. 16, the X$_2$ position in the FIG. 15A structure may be a hydrogen bond acceptor, e.g., O, for forming three hydrogen bonds between the base and its target G:C base-pair.

Figure 15B:
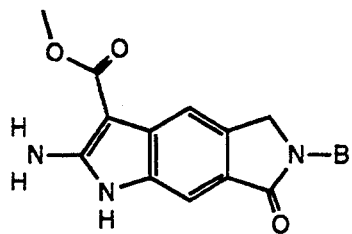
Figure 15C:
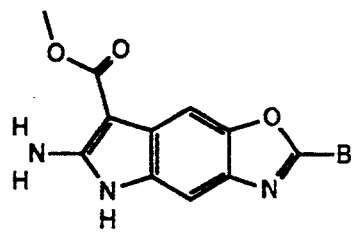
Figure 15D:
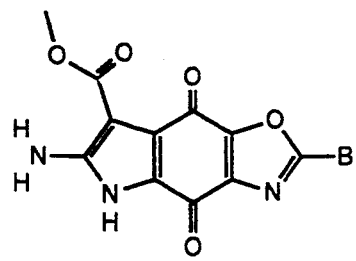
Figure 16:
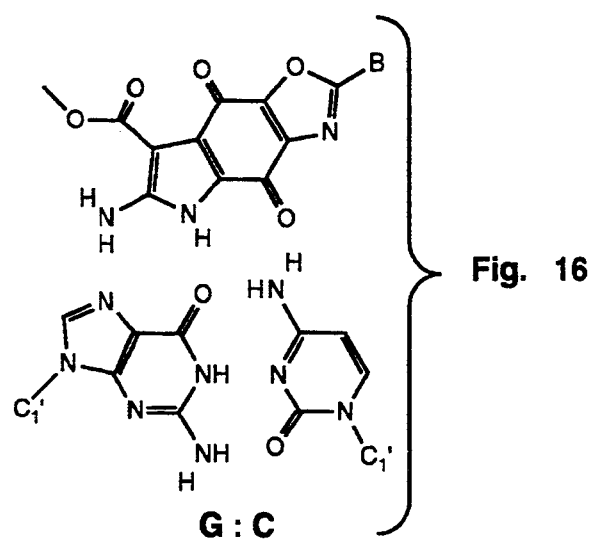
FIG. 16 shows the hydrogen bonding of the FIG. 15D structure to a G:C oriented base-pair.

Syntheses for subunits having a morpholino backbone structure and the G:C-specific bases of FIGS. 15B and 15C are described in Example 4D.

Figure 17A:
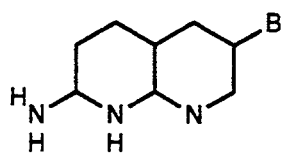
FIG. 17A illustrates the general skeletal ring-structure, hydrogen bonding array, and backbone attachment position of a base designed for binding to a G:C Watson-Crick base-pair.

FIG. 17A shows the skeletal ring structure and hydrogen bonding array of another general type of base effective to bind a G:C oriented base-pair. A preferred embodiment of this structure type hydrogen-bonded to its G:C target base-pair is shown in FIG. 17C.

Figure 17B:
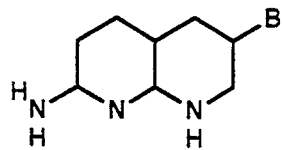
FIG. 17B illustrates the general skeletal ring-structure, hydrogen bonding array, and backbone attachment position of a related base designed for binding to an A:T or A:U Watson-Crick base-pair.
Figure 17C:
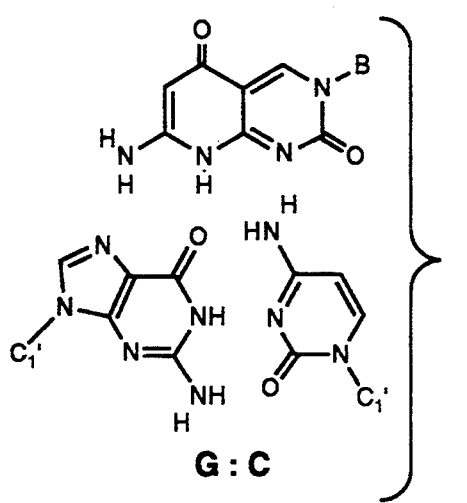
FIG. 17C shows a specific embodiment of the FIG. 17A structure hydrogen bonded to a G:C oriented base-pair.
Figure 17D:
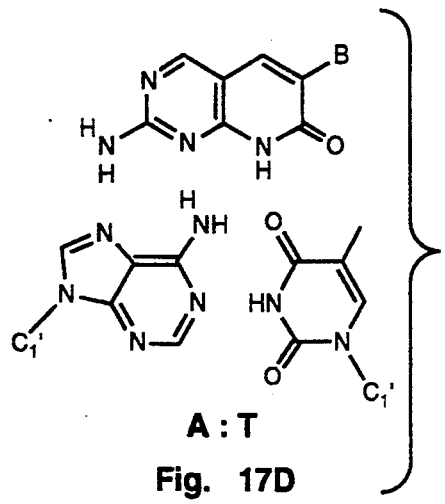
FIG. 17D shows a specific embodiment of the 17B structure hydrogen bonded to a A:T oriented base-pair.

Synthesis of a subunit having a morpholino backbone structure and the G:C-specific base of FIG. 17B is described in Example 4D.

Figure 18A:
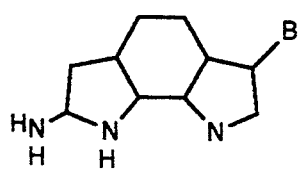
FIGS. 18A–18D illustrate the general skeletal ring-structure, hydrogen bonding array, and backbone attachment position of a base designed for binding to a G:C Watson-Crick base-pair (FIG. 18A), and three specific embodiments of the 18A structure (FIGS. 18B–18D).
Figure 18B:
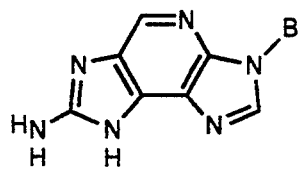
Figure 18C:
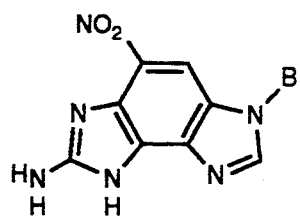
Figure 18D:
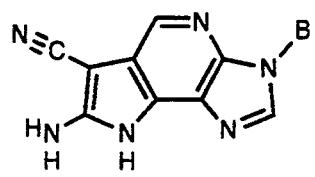
Figure 19:
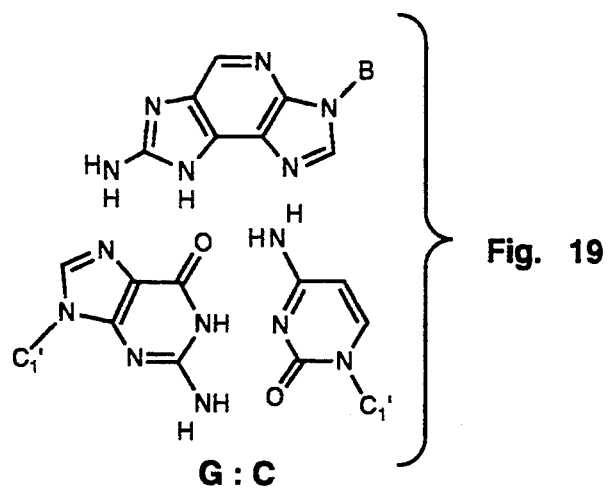
FIG. 19 shows the hydrogen bonding of the FIG. 18B structure to a G:C oriented base-pair.

FIG. 18A shows the skeletal ring structure, hydrogen bonding array, and backbone attachment position of still another general type of base effective to bind a G:C oriented base-pair. Several preferred embodiments of this structure are shown in FIGS. 18B–18D. FIG. 19 shows one embodiment of the 18A structure (18B) hydrogen bonded to its G:C target base-pair.

Synthesis of a subunit having a morpholino backbone structure and the G:C-specific base of FIG. 18B is described in Example 4D.

Figure 20A:
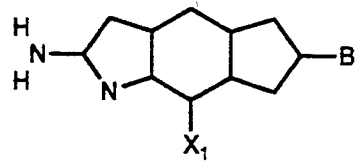
FIG. 20A–20D illustrate the general skeletal ring-structure, hydrogen bonding array, and backbone attachment position of a base designed for binding to an A:T or A:U Watson-Crick base-pair (FIG. 20A), and three specific embodiments of the 20A structure (FIGS. 20B–20D).
Figure 20B:
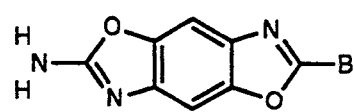
Figure 20C:
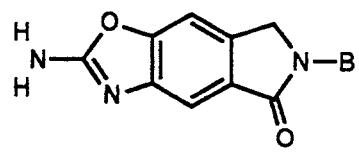
Figure 20D:
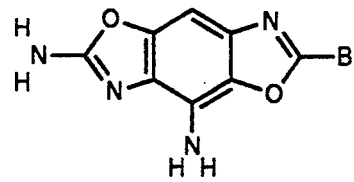
Figure 21:
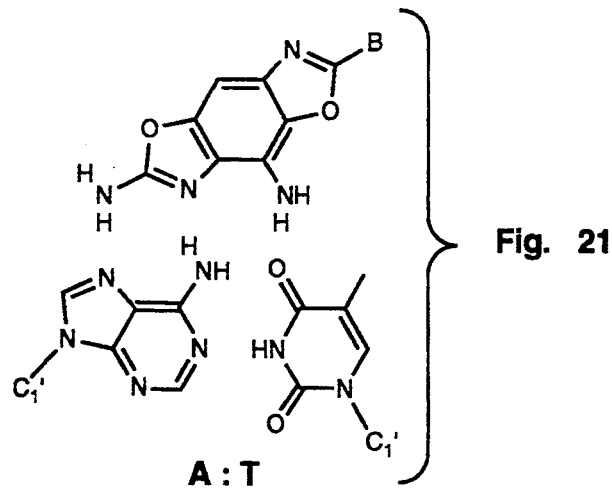
FIG. 21 shows the hydrogen bonding of the FIG. 20D structure to an A:T oriented base-pair.

FIG. 20A shows the skeletal ring structure, hydrogen bonding array, and backbone attachment position of a general type of base effective to bind an A:T or A:U oriented base-pair. Three preferred embodiments of this structure type are shown in FIGS. 20B-20D. FIG. 21 shows the structure in FIG. 20D hydrogen-bonded to its A:T target base-pair.

Syntheses for subunits having a morpholino backbone structure and the A:T or A:U-specific bases of FIGS. 20B and 20C are described in Example 4C.

Figure 22A:
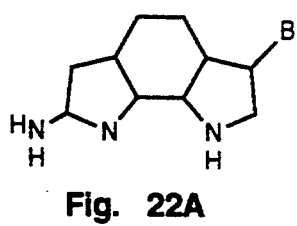
FIGS. 22A–22D illustrate the general skeletal ring-structure, hydrogen bonding array, and backbone attachment position of a base designed for binding to an A:T or A:U Watson-Crick base-pair (FIG. 22A), and three specific embodiments of the 22A structure (FIGS. 22B–22D).
Figure 22B:
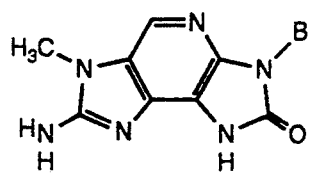
Figure 22C:
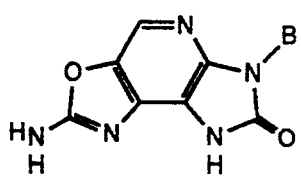
Figure 22D:
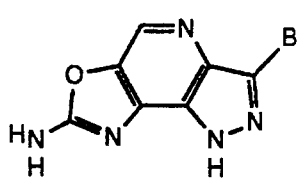
Figure 23:
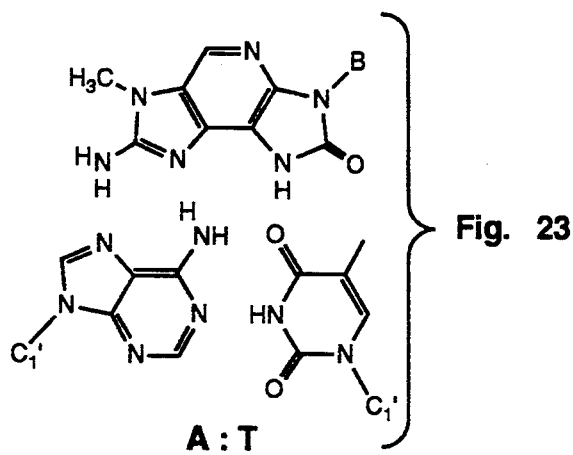
FIG. 23 shows the hydrogen bonding of the FIG. 22B structure to an A:T oriented base-pair.

FIG. 22A shows the skeletal ring structure, hydrogen bonding array, and backbone attachment position of still another general type of base effective to bind an A:T or A:U oriented base-pair. Several preferred embodiments of this structure are shown in FIGS. 22B-22D. FIG. 23 shows one embodiment of the 22A structure (22B) hydrogen bonded to its A:T target base-pair.

Synthesis of a subunit having a morpholino backbone structure and the A:T-specific base of FIG. 22B is described in Example 4C.

The subunits described in this section whose bases are specific for G:C, A:T and A:U oriented base-pairs, with the guanine and diaminopurine subunits described in Section F1, provide a complete set of subunits providing high-specificity hydrogen bonding for each of the four possible oriented base-pairs in duplex nucleic acids. A subunit set formed in accordance with one aspect of the invention may include any three of these high-specificity subunits effective to bind to three different oriented base-pairs in a duplex target sequence. For example, in a target sequence containing T:A, C:G, and G:C base-pairs, the selected subunit set would include three different subunits containing a common or similar backbone structure and diaminopurine, guanine (or thioguanine), and one of the above G:C-specific bases. A subunit set suitable for a target sequence containing all four oriented base-pairs would additionally include a subunit whose base is one of the above high-specificity bases for an A:T or A:U oriented base-pair.

Table 7 shows the base-pair specificities and approximate $R_b$, $\Theta_b$, and A values for the subunit bases comprising guanine, diaminopurine, and the high-specificity bases of FIGS. 15, 17A, 17B, 18, 20, and 22.

TABLE 7

| Subunit Base | Base-pair Specificity | $R_b$ | $\Theta_b$ | A |
|---|---|---|---|---|
| G | C:G | 10.0 A | 19° | 60° |
| D | T:A | 9.9 A | 19° | 60° |
| Base of FIG. 15 | G:C | 10.2 A | 22° | 55° |
| Base of FIG. 17A | G:C | 8.8 A | 19° | 50° |
| Base of FIG. 17B | A:T | 8.8 A | 19° | 50° |
| Base of FIG. 18 | G:C | 9.3 A | 21° | 40° |
| Base of FIG. 20 | A:T | 10.3 A | 20° | 55° |
| Base of FIG. 22 | A:T | 9.3 A | 21° | 40° |

This table illustrates the general suitability of this set of bases in regard to R, $\Theta$, and A values.

5. High-Specificity Subunit Set with Replacements for Guanine and Diaminopurine. When guanine and diaminopurine bases are hydrogen bonded to the polar major-groove sites of their respective target base-pairs in a duplex DNA sequence existing in a B conformation, those two bases afford less than optimal stacking interactions between contiguous bases of the binding polymer. Since stacking interactions generally contribute significantly to the binding affinity of these polymers for their duplex genetic targets, use of bases affording improved stacking interactions can yield polymers with greater target binding affinities.

Accordingly, in another embodiment, the binding polymer includes one or more subunits having bases which are specific for C:G and/or T:A or U:A which provide better stacking interactions than afforded by guanine and/or diaminopurine, particularly when the polymer is bound to its target genetic duplex in a B or B-like conformation.

One preferred subunit set which can be used to prepare polymers with improved stacking interactions when targeted against B-form genetic duplexes includes two or more subunits selected from the following: a G:C-specific base illustrated in FIG. 18; an A:T or A:U-specific base illustrated in FIG. 22; plus an additional acceptably matched (with respect to R, $\Theta$, and A values) subunit whose base is specific for hydrogen bonding to a C:G oriented base-pair and which affords better stacking interactions than guanine; and, an additional acceptably matched subunit whose base is specific for hydrogen bonding to an A:T or A:U oriented base-pair and which affords better stacking interactions than diaminopurine.

Figure 24A:
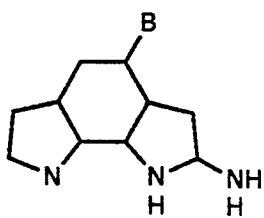
FIG. 24A illustrates the general skeletal ring-structure, hydrogen bonding array, and backbone attachment position of a base designed for binding to an C:G Watson-Crick base-pair.
Figure 24B:
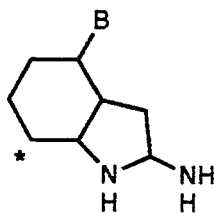
FIG. 24B illustrates the general skeletal ring-structure, hydrogen bonding array, and backbone attachment position of a related base also designed for binding to an C:G Watson-Crick base-pair.
Figure 24C:
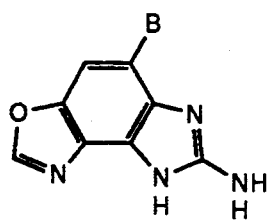
FIG. 24C illustrates a specific embodiment of the FIG. 24A structure.

FIG. 24A illustrates the general skeletal ring structure, hydrogen bonding array, and backbone attachment position of such an acceptably matched base designed for binding to a C:G oriented base-pair, and FIG. 24C illustrates a specific embodiment of the 24A structure. FIG. 24B illustrates the general skeletal ring structure, hydrogen bonding array, and backbone attachment position of a related base also designed for binding to a C:G oriented base-pair, and FIG. 24D illustrates a specific embodiment of the 24B structure.

Figure 24D:
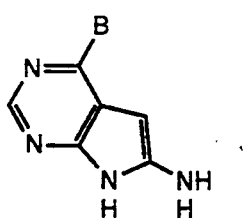
FIG. 24D illustrates a specific embodiment of the FIG. 24B structure.

Synthesis of subunits having a morpholino backbone structure and the C:G-specific bases of FIG. 24C and 24D are described in Example 4A.

Figure 25:
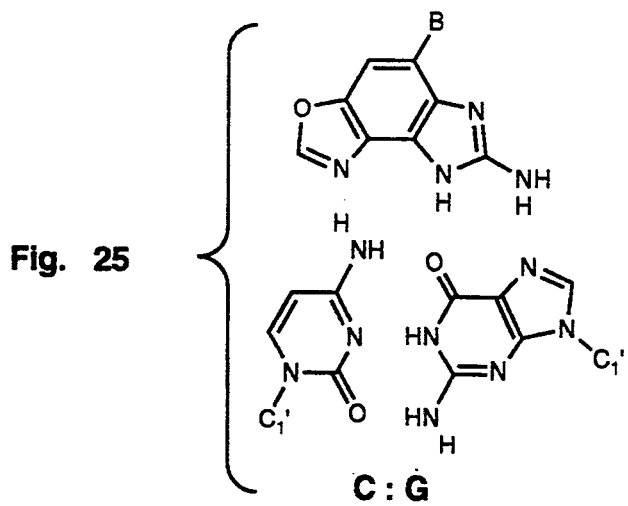
FIG. 25 shows the hydrogen bonding of the FIG. 22C structure to a C:G oriented base-pair.

FIG. 25 shows the hydrogen bonding of the 24C structure to a C:G oriented base-pair.

Figure 26A:
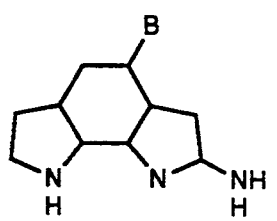
FIG. 26A illustrates the general skeletal ring-structure, hydrogen bonding array, and backbone attachment position of a base designed for binding to a T:A or U:A Watson-Crick base-pair.
Figure 26B:
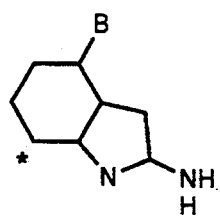
FIG. 26B illustrates the general skeletal ring-structure, hydrogen bonding array, and backbone attachment position of a related base also designed for binding to a T:A or U:A Watson-Crick base-pair.
Figure 26C:
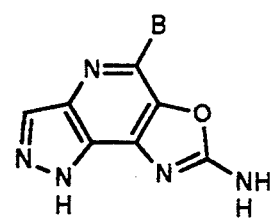
FIGS. 26C–26D illustrate two specific embodiments of the FIG. 26A structure.
Figure 26D:
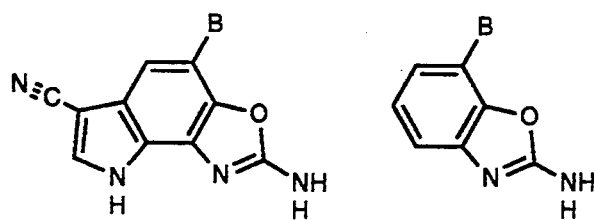

FIG. 26A illustrates the general skeletal ring structure, hydrogen bonding array, and backbone attachment position of such an acceptably matched base designed for binding to a T:A or U:A oriented base-pair, and FIG. 26C and 26D illustrate two specific embodiments of the 26A structure. FIG. 26B illustrates the general skeletal ring structure, hydrogen bonding array, and backbone attachment position of a related base also designed for binding to a T:A or U:A oriented base-pair, and FIG. 26E illustrates a specific embodiment of the 26B structure.

Figure 26E:
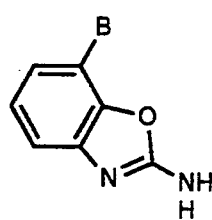
FIG. 26E illustrates a specific embodiment of the FIG. 26B structure.

Synthesis of subunits having a morpholino backbone structure and the T:A or U:A-specific bases of FIG. 26D and 26E are described in Example 4B.

Figure 27:
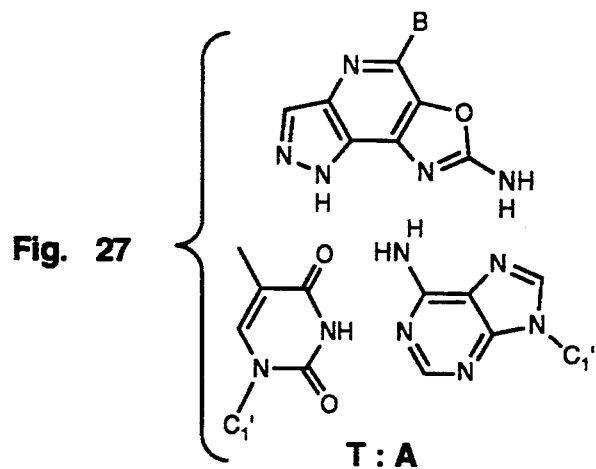
FIG. 27 shows the hydrogen bonding of the FIG. 26C structure to a T:A oriented base-pair.

FIG. 27 shows the hydrogen bonding of the 26C structure to a T:A oriented base-pair.

The subunits described in this section provide a complete set of subunits affording high-specificity hydrogen bonding for each of the four possible oriented base-pairs in duplex nucleic acids, as well as improved stacking interactions between contiguous bases when the binding polymer is in position on its target genetic duplex, especially when that target duplex is in a B or B-like conformation.

Binding polymers containing subunits of this set may also include one or more guanine and/or diaminopurine bases, or analogs thereof.

Table 8 shows the base-pair specificities and approximate $R_b$, $\Theta_b$, and A values for the subunit bases comprising guanine, diaminopurine, and the bases of FIGS. 18, 22, 24 and 26.

TABLE 8

| Subunit Base | Base-pair Specificity | $R_b$ | $\Theta_b$ | A |
|---|---|---|---|---|
| G | C:G | 10.0 A | 19° | 60° |

TABLE 8-continued

| Subunit Base | Base-pair Specificity | $R_b$ | $\Theta_b$ | A |
|---|---|---|---|---|
| Base of FIG. 24 | C:G | 9.6 A | 16° | 50° |
| D | T:A | 9.9 A | 19° | 60° |
| Base of FIG. 26 | T:A | 9.6 A | 15° | 50° |
| Base of FIG. 18 | G:C | 9.3 A | 21° | 40° |
| Base of FIG. 22 | A:T | 9.3 A | 21° | 40° |

6. Additional High-Specificity Subunit Set with Replacements for Guanine and Diaminopurine. Another preferred subunit set which can be used to prepare polymers with improved stacking interactions when targeted against B-form genetic duplexes includes the following.

Figure 28A:
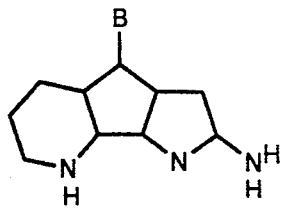
FIG. 28A illustrates the general skeletal ring-structure, hydrogen bonding array, and backbone attachment position of a base designed for binding to a T:A or U:A Watson-Crick base-pair.
Figure 28B:
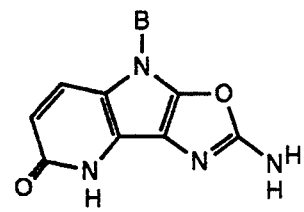
FIG. 28B illustrates a specific embodiment of the FIG. 28A structure.

FIG. 28A illustrates the general skeletal ring structure, hydrogen bonding array, and backbone attachment position of a base designed for binding to a T:A or U:A oriented base-pair, and FIG. 28B illustrates a specific embodiment of the 28A structure.

Synthesis of a subunit having a morpholino backbone structure and the T:A or U:A-specific base of FIG. 28B is described in Example 4B.

Figure 29A:
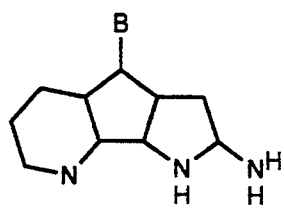
FIG. 29A illustrates the general skeletal ring-structure, hydrogen bonding array, and backbone attachment position of a base designed for binding to a C:G Watson-Crick base-pair.
Figure 29B:
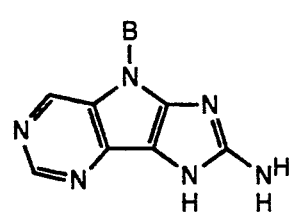
FIG. 29B illustrates a specific embodiment of the 29A structure.

FIG. 29A illustrates the general skeletal ring structure, hydrogen bonding array, and backbone attachment position of a base designed for binding to a C:G oriented base-pair, and FIG. 29B illustrates a specific embodiment of the 29A structure.

Synthesis of a subunit having a morpholino backbone structure and the C:G-specific base of FIG. 29B is described in Example 4A.

Figure 30A:
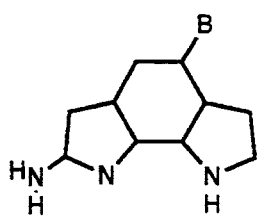
FIG. 30A illustrates the general skeletal ring-structure, hydrogen bonding array, and backbone attachment position of a base designed for binding to an A:T or A:U Watson-Crick base-pair.
Figure 30B:
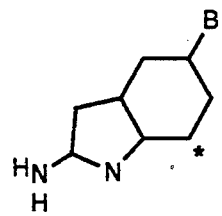
FIG. 30B illustrates the general skeletal ring-structure, hydrogen bonding array, and backbone attachment position of a related base also designed for binding to an A:T or A:U Watson-Crick base-pair.
Figure 30C:
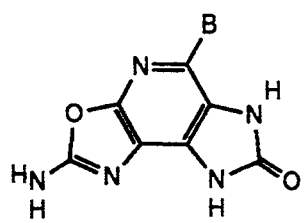
FIGS. 30C–30E illustrate three specific embodiments of the FIG. 30A structure.
Figure 30D:
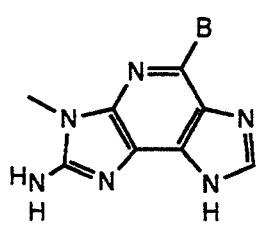
Figure 30E:
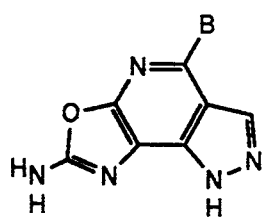

FIG. 30A illustrates the general skeletal ring structure, hydrogen bonding array, and backbone attachment position of such an acceptably matched base designed for binding to a A:T or A:U oriented base-pair, and FIGS. 30C–30E illustrate three specific embodiments of the 30A structure. FIG. 30B illustrates the general skeletal ring structure, hydrogen bonding array, and backbone attachment position of a related base also designed for binding to a A:T or A:U oriented base-pair, and FIG. 30F illustrates a specific embodiment of the 30B structure.

Figure 30F:
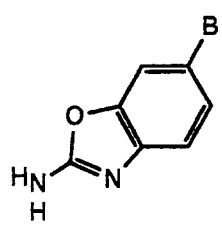
FIG. 30F illustrates a specific embodiment of the FIG. 30B structure.

Synthesis of subunits having a morpholino backbone structure and the A:T or A:U-specific bases of FIGS. 30C and 30F are described in Example 4C.

Figure 31A:
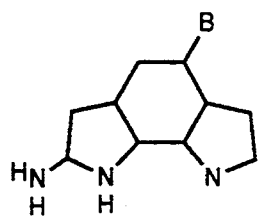
FIG. 31A illustrates the general skeletal ring-structure, hydrogen bonding array, and backbone attachment position of a base designed for binding to a G:C Watson-Crick base-pair.
Figure 31B:
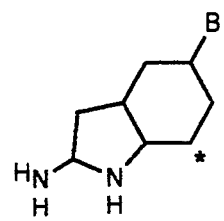
FIG. 31B illustrates the general skeletal ring-structure, hydrogen bonding array, and backbone attachment position of a related base also designed for binding to a G:C Watson-Crick base-pair.
Figure 31C:
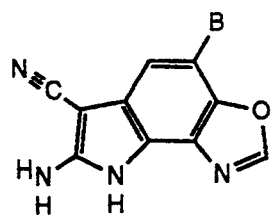
FIG. 31C illustrates a specific embodiment of the FIG. 31A structure.

FIG. 31A illustrates the general skeletal ring structure, hydrogen bonding array, and backbone attachment position of such an acceptably matched base designed for binding to a G:C oriented base-pair, and FIGS. 31C illustrates a specific embodiment of the 31A structure. FIG. 31B illustrates the general skeletal ring structure, hydrogen bonding array, and backbone attachment position of a related base also designed for binding to a G:C oriented base-pair, and FIG. 31D illustrates a specific embodiment of the 31B structure.

Figure 31D:
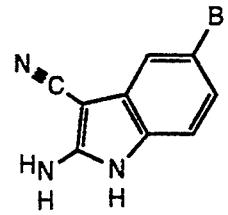
FIG. 31D illustrates a specific embodiment of the FIG. 31B structure.
Figure 32A:
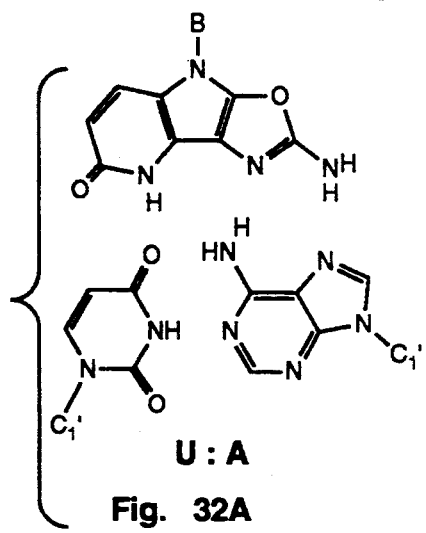
FIG. 32A shows the hydrogen bonding of the FIG. 28B structure to a U:A oriented base-pair.
Figure 32B:
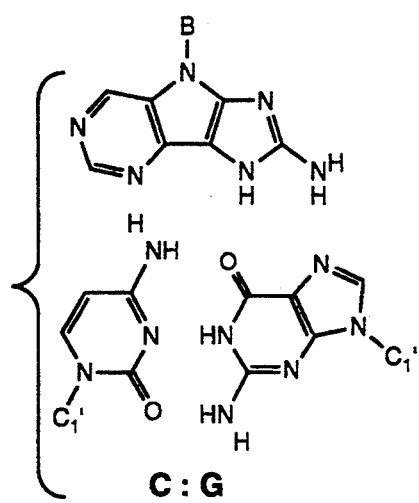
FIG. 32B shows the hydrogen bonding of the FIG. 29B structure to a C:G oriented base-pair.
Figure 32C:
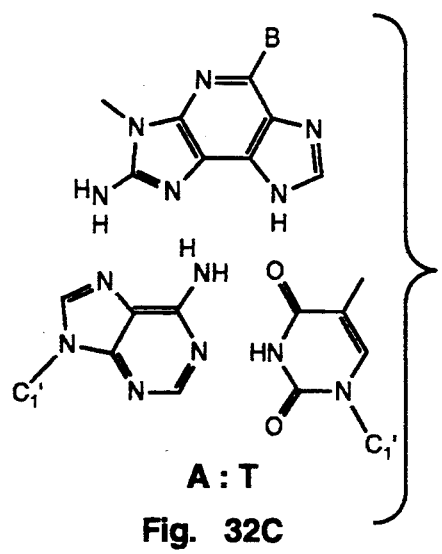
FIG. 32C shows the hydrogen bonding of the FIG. 30D structure to an A:T oriented base-pair.
Figure 32D:
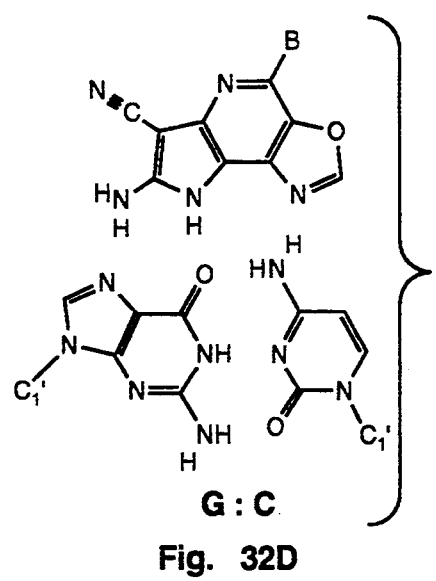
FIG. 32D shows the hydrogen bonding of the FIG. 31C structure to a G:C oriented base-pair.

Synthesis of subunits having a morpholino backbone structure and the G:C-specific bases of FIGS. 31C and 31D are described in Example 4D.

FIG. 32 illustrates binding of representative bases from this subunit set to their respective target base-pairs, including: the FIG. 28B structure hydrogen bonded to a U:A oriented base-pair; the FIG. 29B structure hydrogen bonded to a C:G oriented base-pair; the FIG. 30D structure hydrogen bonded to an A:T oriented base-pair; and, the FIG. 31C structure hydrogen bonded to a G:C oriented base-pair.

The subunits described in this section provide a complete set of subunits affording high-specificity hydrogen bonding for each of the four possible oriented base-pairs in duplex nucleic acids, as well as improved stacking interactions between contiguous bases when the binding polymer is in position on its target genetic duplex, especially when that target duplex is in a B or B-like conformation.

Table 9 shows the base-pair specificities and approximate $R_b$, $\Theta_b$, and A values for the subunit bases comprising the bases of FIGS. 28, 29, 30, and 31.

TABLE 9

| Subunit Base | Base-pair Specificity | $R_b$ | $\Theta_b$ | A |
|---|---|---|---|---|
| Base of FIG. 28 | U:A | 9.0 A | 6° | 20° |
| Base of FIG. 29 | C:G | 9.0 A | 7° | 20° |
| Base of FIG. 30 | A:T | 9.8 A | 4° | 20° |
| Base of FIG. 31 | G:C | 9.8 A | 5° | 20° |

II. Polymer Preparation

This section describes assembly of the subunits, described above, into a sequence-specific duplex-binding polymer.

A. Polymer Sequence and Length

One use of the polymers of the present invention is to bind to and inactivate a target duplex sequence, such as a sequence essential for pathogenicity of a disease-causing agent, without inactivating normal host genetic sequences. Thus, the sequence information recognized by the polymer should distinguish the pathogen sequence from normal host sequences.

An estimate of the amount of sequence information which a duplex nucleic acid-binding polymer should recognize in a disease-specific sequence in order to avoid concomitant attack on normal cellular sequences can be calculated as follows. The human genome contains roughly 3 billion base-pairs of unique-sequence DNA. For a gene-inactivating agent to have an expectation of having no fortuitous target sequences in a cellular pool of 3 billion base-pairs of unique sequence genetic material, it should recognize at least n base-pairs in its target, where n is calculated as $4^n = 3 \times 10^9$. This calculation gives an expected minimal target recognition sequence of approximately 16 base-pairs. Accordingly, a gene-inactivating polymer recognizing in excess of 16 base-pairs in its target sequence has a low likelyhood of having no fortuitous targets in the cellular pool of inherent DNA. Obviously as the number of base-pairs recognized in the target sequence increases over this value the probability that the polymer will attack inherent cellular sequences continues to decrease: as the number of base-pairs recognized by the gene-inactivating polymer increases linearly, this "safety factor" increases exponentially.

To illustrate, Table 8 tabulates the number of base-pairs recognized in a target sequence and the corresponding expected number of fortuitous targets in a pool of 3 billion base-pairs of unique-sequence genetic material.

TABLE 10

| Number of base-pairs recognized in target duplex | Expected number of fortuitous targets in human genome |
|---|---|
| 8 | 45,776 |
| 10 | 2,861 |
| 12 | 179 |
| 14 | 11.2 |
| 16 | 0.7 |
| 18 | 0.044 |
| 20 | 0.0027 |

The numbers in Table 10 indicate that in order to achieve specificity for a pathogen or pathogenic state, a binding agent targeted to duplex nucleic acids should recognize at least 16, and preferably 18 or more base-pairs of the target sequence, to avoid fortuitous sequence binding.

In addition to target sequence length, it is important to consider how many of the four possible oriented base-pairs in duplex nucleic acids (ie., A:T, C:G, G:C, and T:A) must be specifically recognized by the polymer bases in order to allow practical targeting of various viral pathogens. Table 9 shows the approximate number of targets expected in a relatively small viral genome (about the size of the HIV provirus) as a function of the number of different base-pair-binding specificities in a 16-subunit polymer. The values in the table were calculated on the assumption that the purine to pyrimidine ratio in a given strand of the pathogen's genome is approximately 1.0 and that the bases are effectively in a random order.

TABLE 11

| Number of base-pair-binding specificities in subunit set | Expected number of contiguous 16-base-pair targets in a 10,000 base-pair viral genome |
| --- | --- |
| 1 | 0.000002 |
| 2 | 0.15 |
| 3 | 100 |
| 4 | 10,000 |

The tabulated values demonstrate that, typically, homopolymers (i.e., polymers assembled from subunits having specificity for just one oriented base-pair) are unlikely to have targets in natural duplex genetic sequences. Copolymers of two subunit types, with specificities for only two of the four oriented base-pairs, are expected to have contiguous 16-base-pair targets in large viruses, such as Herpes Simplex Virus I. In contrast, binding polymers assembled from subunit sets having specificities for three or four of the oriented base-pairs have an adequate number of targets in even the smallest DNA viruses (e.g., Hepatitis B with a genome size of only 3200 base-pairs).

As described in Section I, the basic two-subunit set formed in accordance with the present invention includes two subunits which are specific for two different oriented base-pairs, C:G and T:A or U:A. To increase targeting versatility, polymers can be assembled from an expanded subunit set which includes one or two spacer subunits in addition to the specific subunits.

Polymers can be assembled from the basic two-subunit set plus an additional semi-specific subunit whose base is capable of hydrogen bonding to either of two different oriented base-pairs (for example, the base of FIG. 13 with A:T or A:U and G:C). As noted above, this semi-specific subunit base recognizes only half the sequence information recognized by a high-specificity subunit base, and thus its use requires a correspondingly longer polymer in order to achieve adequate specificity for its target.

Further, polymers can be assembled from three or four different subunits whose high-specificity bases are each capable of hydrogen bonding to just one of the four oriented base-pairs. Such a subunit set containing subunit bases specific for each of the four possible oriented base-pairs allows construction of a polymer targetable against essentially any desired duplex genetic sequence.

Still another embodiment comprises polymers containing special methyl-discriminating subunits. The moiety at the 5 position of the pyrimidine of base-pairs in duplex nucleic acids provides an exploitable structural difference that yeilds an additional level of targeting specificity. For example, (i) duplex DNA contains a methyl at the 5 position of thymine in A:T and T:A base-pairs, while duplex RNA lacks a methyl at the corresponding position of uracil in A:U and U:A base-pairs, and (ii) clusters of 5'-CpG sequences in the control regions of transcriptionally-inactive genes contain methyls at the 5 position of the cytosines, whereas corresponding transcriptionally-active genes generally lack methyls at the 5 position of these cytosines. The moiety at the 5 position of pyrimidines in duplex nucleic acids has been exploited for target discrimination in nature, for example, the control of cleavage by restriction nucleases in bacteria. The polymers of the present invention (see Section I-C) provides a means to exploit these structural differences to provide a new level of duplex target discrimination. Such polymers provide an additional level of target discrimination by affording effective binding only to duplex target sequences containing a hydrogen at the 5 position of the pyrimidine of specified base-pairs in the target sequence.

B. Subunit Activation and Polymer Assembly

Figures 33, 34:
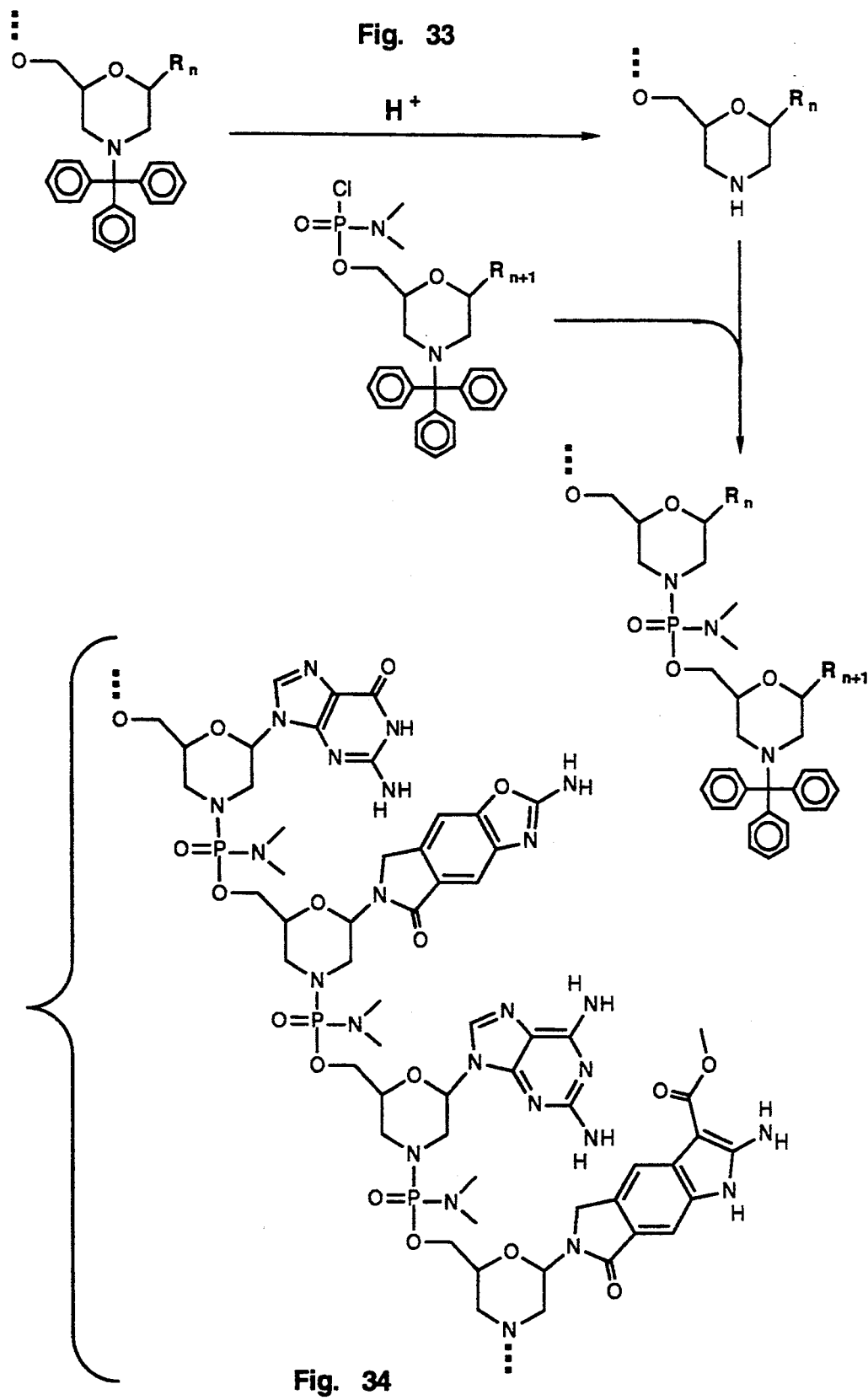
FIG. 33 illustrates the coupling cycle used in an exemplary solid-phase synthesis of one embodiment of the binding polymer of the present invention.
FIG. 34, 35 and 36 illustrate segments of three polymers constructed according to the invention, with each designed to bind to a region of an A-form genetic duplex nucleic acid having the sequence of base-pairs: C:G, A:T, T:A, and G:C.

The subunits, prepared as in Examples 1–5, can be activated and then coupled in a controlled sequential manner to give the desired binding polymer. Representative polymer assembly procedures for deoxyribose-containing and 2'-0-methylribose-containing subunits are described in Example 6. Representative activation procedures for morpholino-containing subunits are described in Example 7; Example 8 describes an exemplary procedure for assembling these activated subunits via solid-phase stepwise addition to give the desired binding polymers; and, Example 9 describes their purification. FIG. 33 illustrates one subunit addition cycle of this stepwise assembly procedure using a representative morpholino subunit prepared as in Example 2C and activated as in Example 7A.

Figure 35:
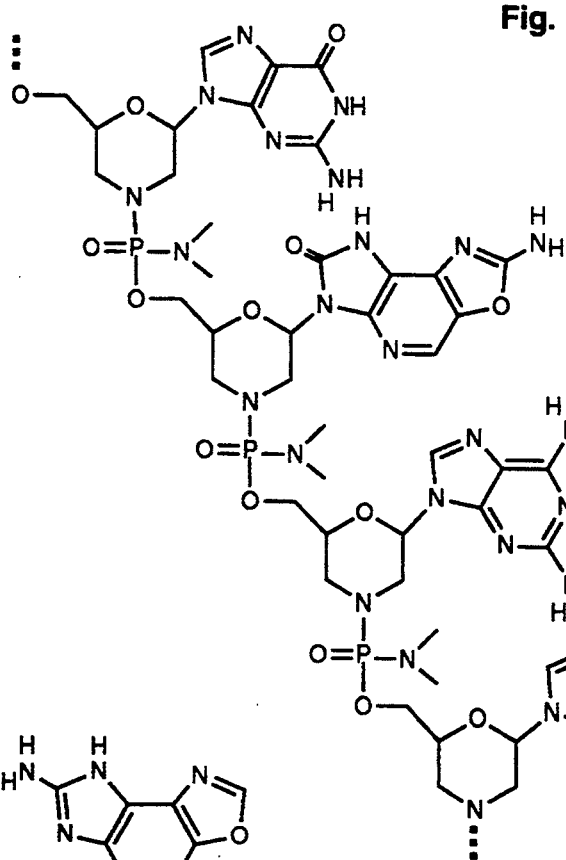

FIGS. 34 and 35 illustrate four-subunit-long segments of representative polymers assembled from the subunit set described in Section 5. I. F4, prepared as in Example 4, and activated as in Example 7A.

Figure 36:
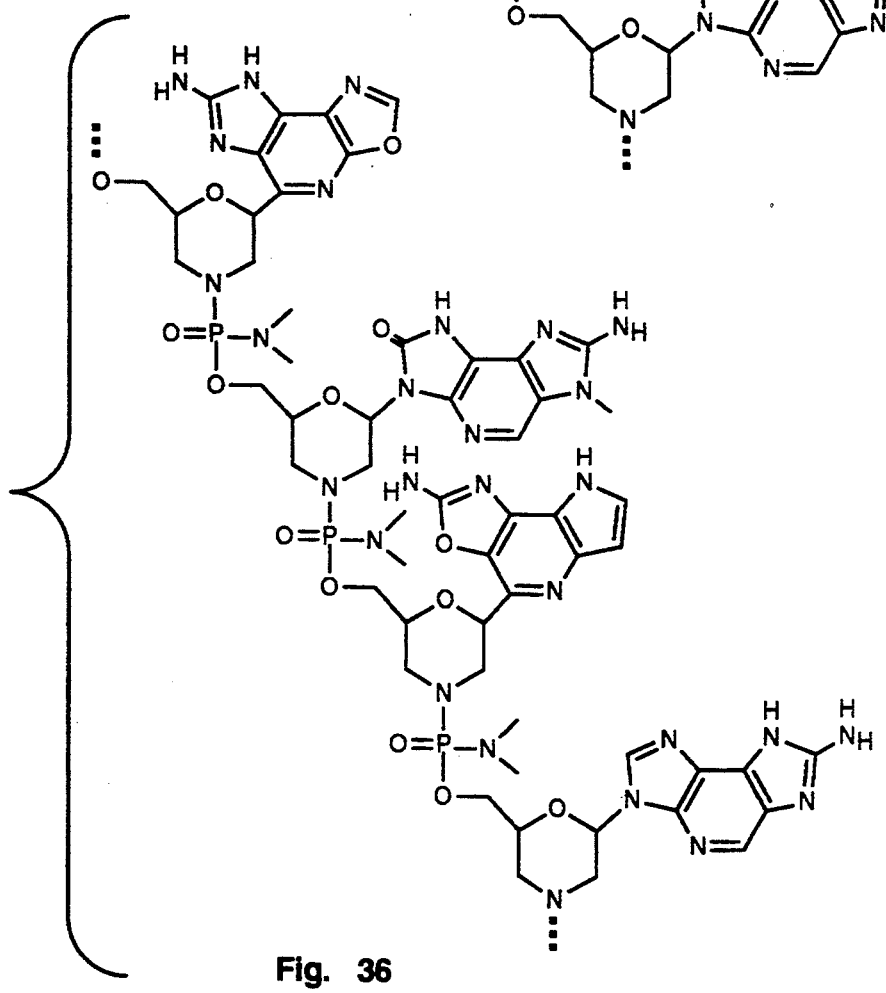

FIG. 36 illustrates a 4-subunit-long segment of a representative polymer assembled from the subunit set described in Section F-5, prepared as in Example 4, and activated as in Example 7A.

FIG. 37 illustrates a 4-subunit-long segment of a corresponding polymer containing two methyl-discriminating subunits which afford binding to an RNA/RNA target sequence, but preclude binding to a corresponding DNA/DNA target sequence.

FIG. 38 illustrates a 4-subunit-long segment of a representative polymer assembled from the subunit set described in Section F-5, containing a 7-atom unit-length backbone suitable for binding a target duplex in the B conformation, and further containing two methyl-discriminating subunits which afford binding to a target sequence containing a CpG/GpC subsequence, but which preclude binding to a corresponding (5mC)pG/Gp(5mC) subsequence.

C. Novel Polymer Assembly Comprising: Oxidation/Ring Closure/Reduction

Figure 39:
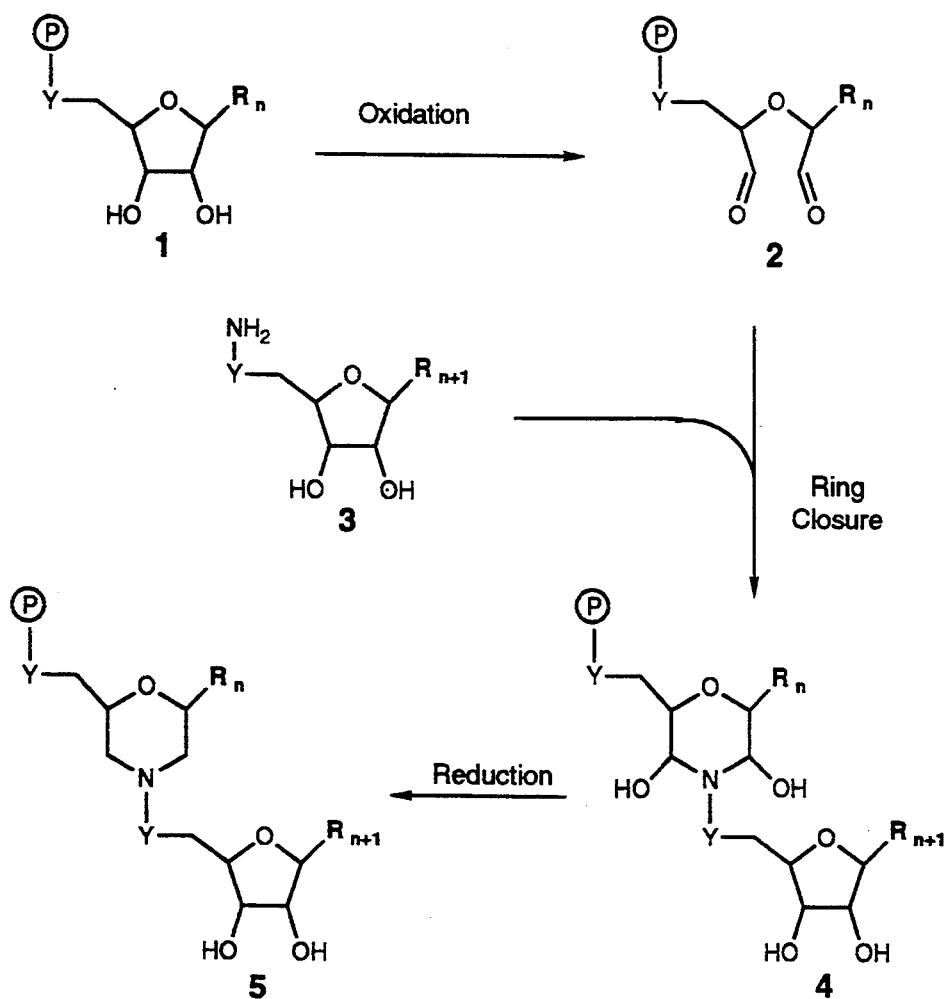
FIG. 39 illustrates the coupling cycle in a novel method for assembling nucleic acid-binding polymers.

In addition to the above, the following exemplary coupling procedure can also be used for assembling the desired nucleic acids binding polymers (FIG. 39). This assembly procedure involves: (i) providing a subunit, or block of linked subunits, which contains vicinyl aliphatic hydroxyls, but no free primary amine (e.g., structure 1 of FIG. 39), (ii) oxidizing those vicinyl hydroxyls to give a dialdehyde component (e.g., structure 2 of FIG. 39), (iii) providing a subunit, or block of subunits, which contains a free primary aliphatic amine (e.g., structure 3 of FIG. 39, and subunits prepared as in Examples 2F–2I), (iv) contacting the dialdehyde component with the primary amine component to effect coupling of the two components via formation of a cyclic morpholino structure having hydroxyls on the carbons adjacent to the morpholino nitrogen (e.g., structure 4 of FIG. 39), and, (v) during or after the coupling reaction, or after completion of polymer assembly, adding a reducing agent to remove the hydroxyls on the carbons adjacent to the morpholino nitrogen, to give the desired morpholino ring structure (e.g., structure 5 of FIG. 39).

The vicinyl-hydroxyl-containing moiety can be other than ribose, such as galactose or glucose. Further, this coupling method can be used in either a solution-phase or a solid-phase mode for polymer assembly. Also, the oxidation step and the subsequent coupling step are preferably carried out in alcohol or water or a mixture thereof, and at a pH near neutrality. Although the reduction can be carried out during or after the coupling, best results are obtained when reducing agent, e.g., $NaCNBH_4$, is present during the coupling step. Complete reduction and disruption of borate complexes (generated when $NaCNBH_4$ is used for the reduction) is best achieved by a final acidic wash having a pH in the range of 3 to 5—which can be carried out after each coupling, or after all couplings are completed.

Example 10 describes a representative application of this "oxidation/ring closure/reduction" coupling method for stepwise solid-phase assembly of a binding polymer.

D. Polymer Modifications

If it is necessary or desireable, the solubility of the polymer can be enhanced by addition of a hydrophilic moiety, such as a polyethylene glycol (PEG) chain. This can be accomplished, according to one approach, by deprotecting the polymer terminus, and reacting the polymer with excess of activated hydrophilic compound, e.g., PEG activated by bis(p-nitrophenyl)carbonate. Thereafter the binding polymer is cleaved from the synthesis support and treated with ammonium hydroxide to remove the base-protecting groups, and then purified, preferably by ion exchange chromatography at pH 10.5. One preferred hydrophilic molecule is PEG having an average molecular weight of about 1000 daltons (commercially available from Polysciences, Inc. and Aldrich Chem. Co.).

For some applications it may be desirable to modify the polymer to favor its cellular uptake via endocytosis. This may be done, for example, by derivatizing the polymer with a polycationic molecule, such as polylysine. Coupling of such a polycationic molecule containing one or more primary amine moieties, may be accomplished by reacting the base-protected polymer with a bifunctional coupling agent, such as disuccinimidyl suberate, or other commercially available agent (e.g., Pierce Chemical Company) and then adding the amine-containing polycationic molecule.

Where the polymer molecules are to be attached to a solid support, e.g., in a diagnostic system, the terminal N-protective group can be cleaved (leaving the bases still in the protected state) and reacted with a suitable crosslinking agent, such as disuccinimidyl suberate. This preparation is then added to the support material, such as latex microparticles containing suitable linker arms terminating in primary amine moieties.

Alternatively, if it is desired to purify the binding polymer prior to attachment to a support, a methoxytrityl- protected 6-aminocaproic acid can be linked to the unprotected N-terminus of the binding polymer using dicyclohexylcarbodiimide (DCC). The binding polymer is then treated with ammonium hydroxide to deprotect the bases, purified by standard methods, and the terminal methoxytrityl is cleaved from the aminocaproic acid moiety. Finally, the purified polymer is mixed with support material having suitable linker arms terminating in p-nitrophenylester moieties, to give covalent coupling of the polymer molecules to the support.

Binding polymers constructed from subunits having cyclic backbone moieties have a strand polarity analogous to the 5' to 3' strand polarity exhibited by standard phosphodiester-linked polynucleotides. The binding polymers of the present invention have the potential to bind their target duplex in either or both of the two oridentations. Accordingly, for a given heteromeric target sequence of base pairs, two binding polymers can be constructed, one having the proper sequence of bases ordered from 5' to 3', and the other having the same sequence of bases, but ordered 3' to 5'. These two polymers can then be tested for their respective binding affinities for the selected duplex target sequence. Similar approaches for determining proper binding orientations for standard polynucleotides are well-known in the art.

E. Polymer Structural Characterization

NMR, two-dimensional NMR, and elemental analysis appears to provide little useful structural information for heteropolymers of the present invention when the polymers are of any significant length (for example, polymers greater than 12 subunits in length).

Polymers prepared as in Example 8 and cleaved from the solid support, but not yet treated with ammonium hydroxide, typically show relatively clean parent ions for polymers up to about 16 to 18 subunits in length, when assessed by positive fast atom bombardment mass spectrometry. For longer polymers, and for polymers lacking protective groups on the bases (such as prepared in Example 10), effective mass analysis requires procedures such as laser desorption or electro-spray.

III. Utility

A. Diagnostics: Detection of Sequences in Duplex Form

In one application, the polymer of the invention is used in a diagnostic method for detecting a duplex target nucleic acid sequence in an analyte. The target sequence is typically a pathogen-specific sequence, such as a virus or bacterial genome sequence, which is to be detected in a biological sample, such as a blood sample.

The target sequence is preferably 15 to 25 subunits in length, to provide the requisite sequence specificity, as discussed above. In one assay format, the diagnostic reagent is a solid support, such as a micro-bead, coated by covalently-bound polymers effective to specifically bind to the duplex target sequence. After sample treatment to release the analyte duplex from bacterium or virus in free form, if necessary, the sample is contacted with the solid support under conditions sufficient to effect base-pair-specific binding of the analyte duplex to the support-bound polymer. Typically, the binding reaction is performed at 20°-37° C. for 10 minutes to 2 hours. After washing the solid support to remove unbound material, the support is contacted with a reporter reagent effective to bind to the captured target duplex, to allow detection of said duplex. The reporter may be a soluble duplex-binding polymer, formed in accordance with the present invention, which is base-pair-specific for a second analyte-specific target sequence in the analyte duplex, and which is labeled with a suitable signal group, such as a fluorescent moiety, for signal detection. The signal group is coupled to the polymer by standard coupling methods, such as described in Section II.

After washing the support, it is examined for bound reporter, which will be proportional to the amount of analyte bound to the support via the sequence-specific binding polymer.

Alternatively, the washed support containing bound analyte duplex may be reacted with a fluorescent intercalating agent specific for nucleic acids, such as ethidium bromide, and then the polymer-bound analyte is assessed by its fluorescence. Another alternative is to react the washed support containing bound analyte duplex with a reporter-labeled polycationic molecule, such as a fluorescent-labeled oligo-cation, as described in co-owned published PCT Application No. PCT/US86/00545 (WO 86/05519). The reporter molecule binds by electrostatic interactions with the negatively charged analyte duplex backbone, but does not bind the substantially uncharged polymer molecules on the solid support. After washing the support to remove unbound material, the reporter bound to the solid support, via the sequence-specific analyte/polymer complex, is measured.

B. In situ Hybridization

In many applications, the in situ hybridization is directed toward a target sequence in a double-stranded duplex nucleic acid, typically a DNA duplex associated with a pathogen or with a selected sequence in chromosomal DNA. To date, in situ hybridization typically includes addition of a labeled nucleic acid probe to a permeabilized cell structure, the structure is heated to a temperature sufficient to denature the target duplex nucleic acid, and the probe and denatured nucleic acid are allowed to react under suitable hybridization conditions. After removing unbound (non-hybridized) probe, the structure is examined for the presence of reporter label, allowing the site(s) of probe binding to target nucleic acid to be localized in the biological structure.

This method has been widely applied to chromosomal DNA, for mapping the location of specific gene sequences and determining distances between known gene sequences, for studying chromosomal distribution of satellite or repeated DNA, for examining nuclear organization, for analyzing chromosomal aberrations, and for localizing DNA damage in single cells or tissue. Several studies have reported on the localization of viral sequences integrated into host-cell chromosomes. The method has also been used to study the position of chromosomes, by three-dimensional reconstruction of sectioned nuclei, and by double in situ hybridization with mercurated and biotinylated probes, using digital image analysis to study interphase chromosome topography (Emmerich). Another general application of the in situ hybridization method is for detecting the presence of virus in host cells, as a diagnostic tool.

In the present application, the polymer of the invention is designed for targeting a specific duplex genetic sequence associated with a cellular or subcellular structure of interest, such as a chromosomal preparation. The polymer is derivatized with a suitable label such as a fluorescent tag. The polymer is preferably added directly to cells or tissue containing the structure being studied, without first permeabilizing the material. Because the polymer is uncharged it can more readily penetrate into living cells without the need for a permeabilization treatment. It further offers the advantage of being resistant to nuclease degradation.

Once in contact with the duplex target material of interest, base-pair-specific binding can occur at normal physiological temperatures, again allowing detection of duplex targets under conditions of normal cell activity, and without heat disruption of the material being studied. After a time sufficient for binding to the target duplex, and washout of unbound polymer, the structure being studied may be examined directly, e.g., by fluorescence microscopy, to observe site-specific localization of the duplex target sequence and possible movement thereof. Alternatively, to reduce fluorescence background, the material may be fixed, e.g., by ethanol treatment, washed to remove unbound reporter, and viewed in fixed form by microscopy.

C. Isolation of Duplexes Containing Target Sequence

Another general application of the polymer invention is for isolating duplex nucleic acid structures from a nucleic acid mixture, such as a mixture of genomic fragments, a blood sample containing a selected viral duplex, or a mixture of plasmids with different duplex inserts in different orientations.

The binding polymer used in the method is (a) designed for base-pair-specific binding to a selected target duplex sequence and (b) capable of being isolated from a liquid sample after capture of the target duplex. To this end, the polymer may be bound to a solid support, as described above, or may be derivatized with a ligand moiety, such as biotin, which permits capture on a solid support, or immunoprecipitation, after binding to the target duplex.

The polymer is added to the sample material and incubated under conditions which allow binding of the polymer to its target sequence, typically for 10 minutes to 2 hours at 20°-37° C. After binding has occurred, the polymer and bound material is isolated from the sample. The isolated material may be released from the polymer by heating, or by chaotropic agents, and further amplified, if necessary by polymerase chain reaction methods, and/or clonal propagation in a suitable cloning vector.

D. Site-Specific DNA Modification

The polymer of the invention is also useful for producing selected site-specific modifications of duplex DNA in vitro. These may include cutting a duplex species at a selected site, or protecting a selected region against restriction or methylating enzymes. The latter application is useful particularly in recombinant DNA technology, where it is often advantageous to be able to protect a vector or heterologous DNA sequence against cutting by a selected restriction endonuclease, or where it is desired to selectively prevent methylation at a given restriction site.

To produce site-specific cleavage in a selected base sequence, the polymer is derivatized with a cleaving moiety, such as a chelated iron group (Dreyer et al., 1985; Dervan, 1986; Moser et al., 1987; Maher et al., 1989) capable of cleaving duplex DNA in a polymer bound state. The polymer sequence is selected to place the cleaving group, which is typically coupled at one polymer end, adjacent to the site to be cleaved. To protect a selected region of duplex target sequence against restriction or methylase enzymes, the polymer includes a sequence for binding to the 4–8 base-pair sequence which specifies a selected restriction enzyme sequence—plus any additional proximal bases effective to give increased specificity for a unique target sequence. After addition of the polymer to the duplex material, the material is treated with the selected restriction or methylating enzyme. After enzyme treatment, the treated duplex is "deprotected" by heating.

E. Therapeutic Application

The polymers of the invention, by their ability to bind to duplex target sequences, have the potential to inactivate or inhibit pathogens or selected genomic sequences, such as oncogenes, associated with disease. Origins of replication and enhancer and promoter sequences are particularly sensitive to inactivation by duplex-directed binding agents, because the agent can occupy a target site required for initiation of replication or transcription of the targeted gene. Such gene-control sequences are known for many pathogenic genes, and also for a variety of oncogenes which have been characterized in humans.

For some therapeutic applications, it may be desirable to modify the binding polymer to favor its delivery to certain cells or tissues, or to favor its delivery to certain subcellular organelles, such as the nucleus (Chelsky). This can be accomplished, for example, by linking the binding polymer to a suitable signal structure, such as desialylated galactosyl-containing proteins (Gregoriadis, 1975) or a cluster of galactose moieties, which favors uptake by liver cells; or such as D-mannose or L-fucose, which favor uptake by Kupffer cells and macrophages; or such as insulin or related peptides, which may then be actively transported across the blood/brain barrier. Additionally, the binding polymers can be incorporated into surfactant micelles, with or without brain-specific antibodies, to enhance delivery across the blood/brain barrier (Kabanov).

For the reasons discussed above, the polymer should generally contain at least 16 base-pair-specific subunits, to minimize the possibility of undesired binding to sequences other than the intended target sequence. Candidate target structures can be determined from analysis of genomic sequences, such as are available in a variety of sequence databases. Preferred target structures are those which are (a) well conserved across strains, and (b) have a base-pair sequence which is compatible with the set of subunits available for forming the polymer. For example, if the subunit set includes a guanine, diaminopurine, and one or two spacer subunits, as detailed in Section I, the target sequence preferably contains at least about 70% C:G and T:A oriented base-pairs, and the remainder G:C and/or T:A.

One therapeutic target for the polymers of the present invention is the HIV-I genome. A sequence search of the HIV-I genome in the duplex proviral stage was performed for sequences (i) well conserved across strains and (ii) suitable targets for binding polymers assembled predominantly from guanine and 2,6-diaminopurine-containing subunits. Table 12 shows several such selected target sequences, and positioned thereon, binding polymers assembled from the "two subunits plus spacers" set of the type described in Section I, E-2.

TABLE 12

| Position in Genome | Gene | Polymer/Target Complex | |
|---|---|---|---|
| | | DDDDDUGDUDGGGGGDD ———————*———*——————— | Polymer |
| 2431 | Pol | 5'-AAAAATGATAGGGGGAA TTTTTACTATCCCCCTT-5' | Target Duplex |
| | | DUDDDGDDDDDDGDCDG —*————————————————*—— | Polymer |
| 2735 | Pol | 5'-ATAAAGAAAAAAGACAG TATTTCTTTTTTCTGTC-5' | Target Duplex |
| | | GGDDDGGUGDDGGGGCDGUDGUDD ———————*—————————*——*——*—— | Polymer |
| 4956 | Pol | 5'-GGAAAGGTGAAGGGGCAGTAGTAA CCTTTCCACTTCCCCGTCATCATT-5' | Target Duplex |

In the table, "-" represents a high-specificity base-pair binding, and "*" represents a low-specificity base-pair binding.

The following examples detail synthetic methods for preparing a variety of subunits, subunit sets, and polymers, in accordance with the invention. The examples are intended to illustrate but not limit the present invention.

EXAMPLE 1

Subunit Protection Methods

A. General Procedure for the Protection of Primary Amino Groups on Bases of Subunits Unless otherwise indicated, chemicals are purchased from Aldrich Chemical Co., Milwaukee, Wis.

The subunit, generally a nucleoside or nucleoside analog, (10 mmol, which has been dried by coevaporation with pyridine several times) is dissolved or suspended in pyridine (50–100 mL), and treated with chlorotrimethylsilane (2–3 equivalents of silane per hydroxyl group in the substrate). The solution is stirred one hour, or until solution is complete (sonication may be employed with difficultly soluble substrates). An alkyl chloroformate, acid chloride, or anhydride, or other suitable activated carboxylic acid derivative is added (1.05–4.0 equivalents per amino group in the substrate). After stirring for 1–24 hours at room temperature, the reaction is cooled to 0° C., and treated slowly with a 1:1 mixture of pyridine/water (20 mL). After 10 minutes concentrated ammonium hydroxide (20 mL) is added and stirring continued for 15 minutes. The solution is concentrated under vacuum and dissolved in ethyl acetate (or ether or chloroform) and shaken with water. The organic phase is removed and the product allowed to crystallize. If no crystallization occurs, the solvent is removed and the residue chromatographed on silica to yield the N-acylated species. Typical chloroformates which are useful include 9-fluorenylmethoxycarbonyl chloride, 2-(p-nitrophenyl)ethoxycarbonyl chloride (Himmelsbach), and 2-(phenylsulfonyl)ethoxycarbonyl chloride (Balgobin). Typical acid chlorides include benzoyl, isobutyryl, and trichloroacetyl. Typical anhydrides include acetic, isobutyric, and trifluroacetic. Other acid derivatives include acyl hydroxybenzotriazolides (prepared from the acid chloride and dry hydroxybenzotriazole in acetonitrile). The latter are advantageously used to introduce the phenylacetyl group. Alternatively, primary amino groups may be protected as amidines by the procedure of McBride, et al.

B. Procedure for the Differential Protection of Primary Diamines on Base-Pair Recognition Moieties 2,6-Diaminopurineriboside (Pfaltz and Bauer, Inc.) is converted by the general procedure in Example 1A into the N-2,N-6 bis-(phenylacetyl)amide. The acyl group at the N-6 position is selectively cleaved by treatment of the nucleoside with iN LiOH in pyridine/ethanol at 0° C. The reaction mixture is neutralized with aq. HCl and the solvents evaporated. The residue may be recrystallized from ethyl acetate/ethanol or purified by silica gel chromatography. The crude product, or the purified nucleoside, is resubjected to acylation by the general procedure using benzoyl chloride to introduce the N-6 benzoyl group. For this second acylation only a slight excess of the acylating agent (1.05-1.2 equivalents) is employed.

C. Procedure for the Protection of Oxo Groups in the Recognition Moieties

2', 3', 5'-Tri-O-isobutyryl N2-isobutyrl deoxyguanosine is converted by the procedure of Trichtinger, et al, into the 06 2-(p-nitrophenyl)ethyl derivative. Alternatively, guanosine may be converted into the 06 diphenylcarbamoyl derivative by the method of Kamimura, et al. Following treatment with ammonia (1:1 conc. ammonium hydroxide/DMF) or 1N LiOH in pyridine/ethanol at 0° C., the N2-propionyl 06-diphenylcarbamoyl guanosine is produced. These procedures are applicable to the preparation of N-2 acylated O-4 protected 2-amino-4(3H)-quinazolinone derivatives and N-7 acylated )-9 protected 7-amino-9(8H)-imidazo[4,5-f]quinazolinone derivatives.

D. General Procedure for the Introduction of a Dimethoxytrityl Substituent at a Primary Alcohol The alcohol bearing substrate (10 mmol) is dissolved or suspended in pyridine (50-100 mL) and treated with 4,4'-dimethoxytrityl chloride, triethylamine (20 mmol) and 4-dimethylaminopyridine (0.5 mmol). After several hours at room temperature the mixture is treated with water (5 mL) then poured into cold, satd. aq. sodium bicarbonate solution. The mixture is extracted with ethyl acetate (or chloroform) and the combined organic layers are dried (sodium sulfate) and evaporated. The residue is chromatographed on silica to give pure dimethoxytritylated compound.

EXAMPLE 2

Preparation of "2-Subunits plus Spacers" Set.

A. Subunits containing 2'-Deoxyribose moiety (FIG. 5A)

The 5'-O-dimethoxytrityl protected derivatives of the following are available from Sigma (St. Louis, Mo., USA) : N-4 benzoyldeoxycytidine, N-2 isobutyryldeoxyguanosine, thymidine. 2,6-Diaminopurine-2'-deoxyriboside is available from Sigma and is protected at the primary amino groups and the primary hydroxy group by the methods in Example 1.

B. Subunits Containing 2'-O-Methylribose Moiety (FIG. 5B)

The 2'-O-methylribonucleosides of uracil, cytosine, guanine, adenine, and 7-deazaadenine may be obtained by the method of Robins, et al (1974) or Sekine, et al. The guanosine and 2-aminoadenosine 2'-O-methyl ethers are also advantageously prepared by the method of Robins, et al, (1981). They may be converted into their base protected analogues by the general methods in Example 1 (for example, N-2 isobutyryl for the guanosine derivative, N-2 phenylacetyl, N-6 benzoyl for the 2-aminoadenosine derivative, N-4 benzoyl for the cytidine derivative). The primary hydroxy is protected as in Example 1.

Figure 6A:
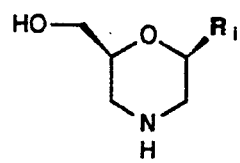
FIGS. 6A–6F show representative morpholino backbone structures suitable for use in forming the polymer of the invention.
Figure 6B:
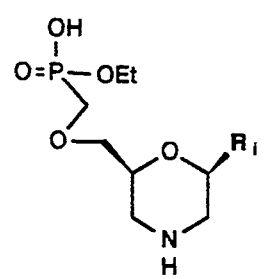

C. Subunits Containing Morpholino Moiety (FIG. 6A)

A ribose-containing subunit, having the base in the protected form, is oxidized with periodate to a 2'-3' dialdehyde. The dialdehyde is closed on ammonia or primary amine and the 2' and 3' hydroxyls (numbered as in the parent ribose) are removed by reduction with cyanoborohydride.

An example of this general synthetic scheme is described below with reference to the synthesis of a base-protected cytosine ($R_i$*) morpholino subunit. To 1.6 L of methanol is added, with stirring, 0.1 mole of N4-benzoylcytidine and 0.105 mole sodium periodate dissolved in 100 ml of water. After 5 minutes, 0.12 mole of ammonium biborate is added, and the mixture is stirred 1 hour at room temperature, chilled and filtered. To the filtrate is added 0.12 mole of sodium cyanoborohydride. After 10 minutes, 0.2 mole of toluenesulfonic acid is added. After another 30 minutes, another 0.2 mole of toluenesulfonic acid is added and the mixture is chilled and filtered. The solid precipitate is dried under vacuum to give the tosylate salt of the free amine. The use of a moderately strong (pKa<3) aromatic acid, such as toluenesulfonic acid or 2-naphthalenesulfonic acid, provides ease of handling, significantly improved yields, and a high level of product purity.

Filtration of the tosylate salt of the 2,6-diaminopurine-containing morpholino subunit also works well. However, the tosylate salts of the guanine-containing and uracil-containing subunits are generally more soluble in methanol. Thus, for G and U subunits the methanol is removed under reduced pressure and the residue partitioned between brine and isopropanol—with the desired product going into the organic phase.

The base-protected morpholino subunit can then be protected at the annular nitrogen of the morpholino ring using trityl chloride.

As an example of the tritylation step, to 2 liters of acetonitrile is added, with stirring, 0.1 mole of the tosylate salt from above, followed by 0.26 mole of triethylamine and 0.15 mole of trityl chloride. The mixture is covered and stirred for 1 hour at room temperature, after which 100 ml of methanol is added, followed by stirring for 15 minutes. The solvent is removed under reduced pressure and then 400 ml of methanol is added. After the solid is thoroughly suspended as a slurry, 5 liters of water is added, the mixture is stirred for 30 minutes, and filtered. The solid is washed with 1 liter of water, filtered and dried under vacuum. The solid is resuspended in 500 ml of dichloromethane, filtered, and rotovaped until precipitation just begins, after which 1 liter of hexane is added and stirred for 15 minutes. The solid is removed by filtering, and dried under vacuum.

The above procedure yields the base-protected morpholino subunit tritylated on the morpholino nitrogen and having a free 5' hydroxyl (numbered as in the parent ribose).

Figure 6C:
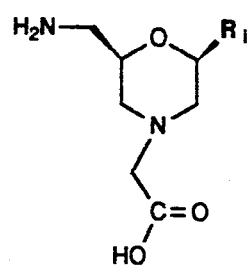
Figure 6D:
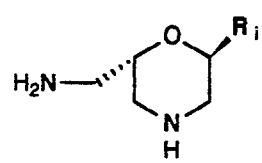
Figure 6E:
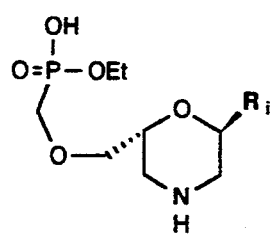

D. Subunits Containing N-Carboxymethylmorpholino-5'-amino Moiety (FIG. 6C)

A ribose-containing subunit, having the base-pair recognition moiety in the protected form, is converted to the 5' amine and that 5' amine tritylated, as per Stirchak, Summerton, and Weller (1987), or by the method described in Example 2E below. Following the general procedures of Example 2C above, the vicinyl 2' and 3' hydroxyls of the ribose are then oxidized with periodate to give a 2'-3' dialdehyde. The dialdehyde is closed on glycine in the presence of triethylamine. The 2' and 3' hydroxyls (numbered as in the parent ribose) are subsequently removed by reduction with cyanoborohydride.

Alternatively, the dialdehyde can be closed on ammonia and reduced as in Example 2C, and then the morpholino nitrogen alkylated with bromoacetic acid buffered with N,N-diethylaniline.

These procedures yield the base-protected morpholino subunit having a tritylated 5' amine and a carboxymethyl group on the morpholino nitrogen.

Figure 6F:
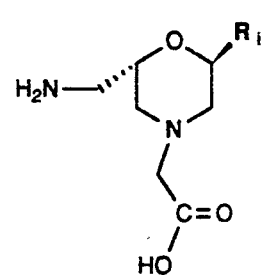
Figure 7A:
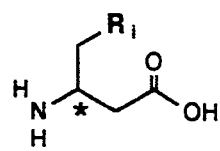
FIGS. 7A–7F show representative acyclic backbone structures suitable for forming the polymer of the invention.
Figure 7B:
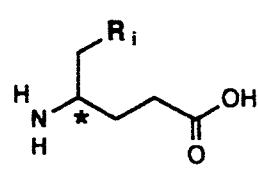
Figure 7C:
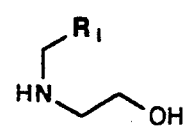
Figure 7D:
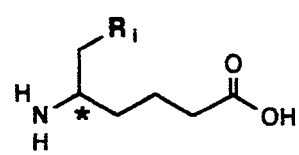
Figure 7E:
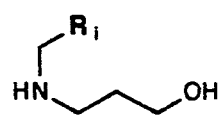
Figure 7F:
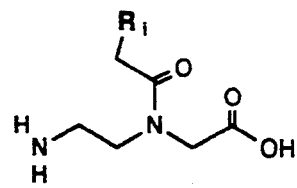

E. Subunits Containing N-Carboxymethylmorpholino-alpha(5'-amino) Moiety (FIG. 6F)

Examples 2C and 2D illustrate the preparation of morpholino-containing subunits wherein the 5' methylene is in the beta orientation—that is, the same orientation as in the parent ribose. Analogous morpholino-containing subunits wherein the 5' methylene is in the alpha orientation can be prepared by the following general approach.

The 5' hydroxyl of a ribose-containing subunit, having the base-pair recognition moiety in the protected form, is converted to a secondary amine by established methods (see Example 2D above). Thereafter, following the general procedures of Example 2C above, the vicinyl 2' and 3' hydroxyls of the ribose are oxidized with periodate to give a 2'-3' dialdehyde. The 2' aldehyde rapidly closes on the secondary amine at the 5' position (numbered as in the parent Ribose). Reduction with cyanoborohydride then generates a structure containing a morpholino ring wherein the annular morpholino nitrogen is tertiary, and containing a 5' aldehyde in the alpha orientation. Subsequent addition of ammonia or a primary amine, in the presence of excess cyanoborohydride, generates a 5' amine (primary or secondary, respectively) in the alpha orientation.

The above general strategy can be applied to prepare subunits containing N-carboxymethylmorpholino-alpha(5'-amino) moiety, as well as a number of other useful variations. One method to introduce the desired secondary amine at the 5' position of the ribose moiety entails: a) conversion of the 2', 3' hydroxyls to an acetal as per the method of Smith, Rammler, Goldberg and Khorana (1961); b) oxidation of the 5'hydroxyl to an aldehyde using DMSO/pyridine/trifluoroacetic acid/-diisoproylycarbodiimide (the Moffat oxidation); c) reacting this 5' aldehyde with glycine (or the tert-Butyl ester of glycine) in the presence of cyanoborohydride; and, regeneration of the 2', 3' hydroxyls by acid cleavage of the acetal.

F. Subunits Containing Ribose with 5'-Carbazate (FIG. 5C)

A ribose-containing subunit can be converted to the 5'carbazate as follows. To 10 mMole of ribose-containing subunit, having exocyclic amines of the base-pair recognition moiety in the protected state, add 100 ml of anisylaldehyde and 0.5 g of tosic acid. Stir at room temperature for 48 hours. Add the reaction mixture to 500 ml hexane and collect the precipitate. Purify the product by silica gel chromatography developed with ether. The resulting product is reacted with 2 equivalents of bis(p-nitrophenyl)carbonate plus 2 equivalents of triethylamine in acetonitrile for 8 hours at 30° C. The product is purified by silica gel chromatography developed with a 5% to 15% acetone/chloroform mixture. The product is reacted with 4 equivalents of t-butylcarbazate in DMF for 4 hrs at 50° C. The reaction mixture is added to water and the precipitate collected and suspended in DMF/Con $NH_4OH$, 1:1 by vol overnight at 30° C. The ammonium solution is added to brine and the insoluble product collected and dried under vacuum. The dry product is dissolved in trifluoroacetic acid and, after 5 minutes, ether is added to precipitate the product, which is triturated twice with ether. The product is dissolved in methanol containing sufficient N-ethylmorpholine to neutralize all residual trifluoroacetic acid and the product again precipitated by addition of ether, and the product dried under vacuum. The desired 5'carbazate product can generally be purified by silica gel chromatography developed with N-ethylmorpholine/methanol/chloroform, 1:4:6 by volume, or preferably, purified by recrystalization from a suitable aqueous/organic mixture.

G. Subunits Containing Ribose with 5'-Sulfonylhydrazide

A ribose-containing subunit can be converted to the 5'-sulfonylhydrazide as follows. Ten mMole of ribose-containing subunit, having exocyclic amines of the base-pair recognition moiety in the protected state, is converted to the anisylacetal derivative as described in Example 2F above.

To 10 mMole of sulfonyl chloride in dichloromethane chilled on dry ice add 15 mMole of N,N-diethylaniline. Next, slowly add, with rapid stirring, a dilute solution of 10 mMole of N-aminophthalimide in dichloromethane.

After 20 minutes, add the anisylacetal subunit derivative to this chlorosulfonylhydrazide solution. Slowly add, with rapid stirring, 30 mMole of diisopropylethylamine in 30 ml of dichloromethane. After stirring 1 hour at room temperature, remove the solvent under reduced pressure and purify the product by silica gel chromatography developed with an acetone/chloroform mixture.

The product is then treated with hydrazine acetate in methanol, the solvent removed under reduced pressure, and DMF/con $NH_4OH$, 1:1 by vol is added and the preparation incubated at 30° C. overnight. Lastly, the product is treated with trifluoroacetic acid and worked up as in Example 2F.

H. Subunits Containing Ribose with 5'-Glycinamide

A primary amine is introduced into the 5' position of a ribose-containing subunit following the oxidation/reductive alkylation procedure described in Example 2E, excepting ammonia, is used instead of Glycine. This 5' primary amine is then acylated with N-tert-butoxycarbonyl glycine, p-nitrophenyl ester. After purification, the protective groups are removed by treatment with DMF/con $NH_4OH$, and then with trifluoroacetic acid, and the final 5'-glycinamide derivative worked up as in Example 2F.

I. Subunits containing Ribose with an Aminomethylethylphosphate Group Linked to the 5'Oxygen Aminomethylphosphonic acid (Aldrich Chem. Co.) is reacted with trityl chloride in the presence of triethylamine. The di-anionic phosphonate product, where the counter ions are triethylammonium, is suspended in ethanol and then a carbodiimide, such as dicyclohexylcarbodiimide (DCC), is added. The resultant monoanionic product is shaken with a mixture of water and chloroform containing pyridinium hydrochloride. This procedure gives a mono-ionic phosphonic acid having a pyridinium counter ion. This product is added to chloroform, followed by addition of the ribose-containing subunit wherein exocyclic amines of the base is in the protected form and the 2' and 3' hydroxyls are protected as the anisylacetal. DCC is added to couple the phosphonate to the 5'oxygen of the subunit. The product is dried and chromatographed on silica using methanol/chloroform mixtures. The pure product is next base-deprotected with DMF/conNH4OH, 1:1 by vol. and then suspended in trifluoroacetic acid to remove the trityl and the anisyl protective group

EXAMPLE 3

Preparation of Subunits With Tautomeric Bas
A. Subunit Containing 2'-Deoxyribose Moiety (FIG. 5A)

1. Subunit containing the base of FIG. 13. 4-Acetylamino-2-methylbenzoic acid (Peltier) is converted into the 5-nitro compound by treatment with cold fuming nitric acid. The reaction mix was poured into crushed ice and the solid product collected by filtration and purified by recrystallization from DMF/water or by silica chromatography. The acetamide is removed by alkaline hydrolysis with 1–10% NaOH solution in 90% ethanol. The reaction mixture was added to excess dilute HCl and the solvent evaporated. The crude acid is esterified with satd. methanolic HCl at room temperature for several days. After removal of solvent the product is partitioned between ethyl acetate and satd. sodium bicarbonate. After washing with water the organic phase is evaporated and the residue purified by silica chromatography. The nitro group is reduced to the amino using hydrogen and palladium on carbon in ethanol or DMF. After filtration through celite and evaporation, the crude diamine is converted to the methyl 2-amino-6-methylbenzimidazole-5-carboxylate using cyanogen bromide in methanol at reflux. The mixture is cooled and poured into satd. aq. sodium bicarbonate and the solid product filtered and purified by recrystallization. The exocyclic amino group is acylated by refluxing with phthaloyl dichloride in pyridine followed by reaction of the diazepine with pyrazole in refluxing acetonitrile according to the method of Katritzky. The compound is reacted with either bromine or N-bromosuccinimide or 1,3-dibromo-5,5-dimethylhydantoin either neat or in carbon tetrachloride or chloroform or 1,1,1-trichloroethane with the aid of a high-intensity sun lamp and/or benzoyl peroxide, to provide the benzylic bromide. It is possible to acylate the diazepine further with isobutryl chloride in pyridine to produce a triply acylated benzimidazole species. This is normally done prior to the bromination.

The crude benzylic bromide is reacted with sodium azide in dry DMF and reduced with hydrogen over platinum or palladium to produce the lactam. This is O-silylated with one equivalent of trimethylsilyl trifluoromethanesulfonate or tert-butyldimethylsilyl trifluoromethanesulfonate to produce the O-silyl lactim ether/benzimidazole trifluoromethanesulfonate salt. This is reacted with 3,5-di-O-toluyl-alpha-D-erythropentofuanosyl chloride (Hoffer) in THF or acetonitrile in the presence of p-nitrophenol by the method of Aoyama to give the protected nucleoside which is purified by silica chromatography. The acyl groups are all removed by a two step procedure involving first, hydrazineolysis with hydrazine/ethanol at room temperature, then evaporation of solvent and heating the crude residue in refluxing ethanol to fully cleave the phthaloyl residue. The aminobenzimidazole is protected by reaction with 4-(dimethoxymethyl)-morpholine (prepared from 4-formyl morpholine by the general procedure of Bredereck et. al.) in methanol to form the amidine. The remaining reactive site of the benzimidazole is protected by reaction with pivaloyl chloride under the conditions of Example 1. Alternatively, the final acylation may be done with—(dimethylamino)benzoyl chloride. An alternative amino protecting group is formed by reaction of the unprotected benzimidazole with 4-(dimethylamino)benzaldehyde in methanol in the presence of piperidine (10 mole %) and methanesulfonic acid (5 mole % ). The resulting imine is acylated as for the amidine. The primary hydroxyl group is protected with the dimethoxytrityl group as per Example 1.

2. Subunit containing the base of FIG. 13C. 3-Acetamidophenol (Aldrich Chemical Co.) is nitrated to give the 2-nitro-5-acetamidophenol. Reduction with hydrogen and palladium/carbon and reaction with trifluoroacetic anhydride or trichloroacetic anhydride give the 2-trihaloacetamido derivative. This is nitrated to give the 4-nitro species and the trihaloacetyl group removed by brief ammonolysis to give 5-acetamido-2-amino-4-nitrophenol.

2,5-Anhydro-3,4,6-tri-O-benzoyl-D-allonothioamide (Pickering, et al.) is treated with methyl iodide and sodium hydride to give the corresponding methyl thioimidate. Alternatively the thioamide is reacted with di-tert-butyl dicarbonate (Aldrich) and 4-dimethylaminopyridine in dichloromethane to produce the imide. Alternatively, the imide is treated with methyl iodide or methyl triflate in the presence of diisopropylethylamine to give the N-tert-butoxycarbonyl methyl thioimidate. Any of these are suitable for reaction with aromatic 1,2-diamines or ortho aminophenols to produce benzimidazole or benzoxazole derivatives of deoxyribosides, respectively.

The aminophenol is reacted with the appropriate activated thioamide from the previous paragraph to produce the 2-(tri-O-benzoyl-beta-deoxyribosyl)benzoxazole. The N-acetyl and O-benzoyl groups are removed by ammonolysis or hydrazinolysis and the nitro group reduced with hydrogen and palladium/carbon. The aromatic diamine is reacted with cyanogen bromide in refluxing methanol, and the product 6-amino-2-(tri-O-benzoyl-betadeoxyribosyl)imidazo[4,5-f]benzoxazole derivative protected as in Example 3A1, and the primary hydroxy protected as per Example 1.

B. Subunit Containing Ribose Moiety (FIG. 5B)

1. Subunit Containing the Base of FIG. 13B. The ribose nucleoside is prepared as for the deoxyribonucleoside in Example 3A1 except that the O-silylated lactam is reacted in the presence of mercuric bromide or silver trifluoromethanesulfonate with the ribosyl bromide prepared from by treatment of 1-O-acetyl-2,3,5-tri-O-benzoyl-D-ribofuranose with HBr in benzene as per the procedure of Maeba et al.

2. Subunit Containing the Base of FIG. 13C. 2,5-Anhydro-3-deoxy-4,6-di-O-toluoyl-D-ribo-hexanothioamide (Pickering, et al.) is converted into the methyl thioimidate, the imide, or the N-tert-butoxycarbonyl methyl thioimidate as in Example 3A2. Any of these are suitable for reaction with aromatic 1,2-diamines or ortho aminophenols to produce benzimidazole or benzoxazole derivatives of ribosides, respectively.

By the same procedures in Example 3A2, the aminophenol is reacted with the activated thioamide from the previous paragraph to produce the benzoxazole which is further converted into the protected nucleoside by the procedures in Example 3A2.

C. Subunit Containing Morpholino Moiety (FIG. 6A)

1. Subunit Containing the Base of FIG. 13B. The morpholine nucleoside is prepared by reaction of the O-silylated lactam from Example 3A1 with tetraacetyl alpha-D-glucopyranosyl bromide (Sigma) (with or without the presence of mercuric bromide or silver trifluoromethanesulfonate). The glycoside is converted into the morpholino nucleoside in the usual way except that twice the normal amount of sodium periodate is employed. Following N-tritylation (Example 2C) and hydrazinolysis of the base protecting groups, the base is reprotected as in Example 3A1.

Alternatively, the morpholine nucleoside is prepared by reaction of the benzylic bromide from Example 3A1 with beta-D-glucopyranosylamine (Tamura, et al.) to give the glycosyl lactam directly. This is converted into the morpholino nucleoside by the usual procedure except that twice the amount of sodium periodate is employed in the oxidation step. Following N-tritylation (Example 2C) and hydrazinolysis of the base, reprotection is accomplished as in Example 3A1.

Alternatively, the methyl 4-acetamido-2-methyl-5-nitrobenzoate from Example 3A1 is brominated as in Example 3A1 and reacted with beta-D-glucopyranosylamine. The N-acetyl is removed with 1–10% NaOH in 90% ethanol, the nitro is reduced with palladium/carbon and hydrogen, and the aminobenzimidazole is formed by reaction with cyanogen bromide in refluxing ethanol. The aminobenzimidazole is protected as in Example 3A1.

Alternatively, the riboside prepared in Example 3B1 is converted into a morpholine-containing subunit following the procedure in Example 2C. This procedure is accomplished prior to deacylation of the phthaloyl group from the aminobenzimidalole. After morpholine formation and protection as the N-trityl species, the phthaloyl group is removed as in Example 3A1.

The morpholine nitrogen is protected as the N-trityl by reaction of the free amine or the tosylate salt with trityl chloride in acetonitrile containing triethyamine. The reaction mix is poured into water and the solid product isolated by filtration and purified by silica gel chromatography.

Subunit Containing the Base of FIG. 13C. By the procedures described in Myers, et al. 2,3,4,6-tetra-O-acetyl-alpha-D-galactopyranosyl bromide is converted into 2,3,4,6-tetra-O-acetyl-alpha-D-galactopyranosyl cyanide and then into the corresponding thioamide by the method of Pickering, et al, and then into its activated thioamide derivatives as in Example 3A2. These are suitable for reacting with 1,2-diamines or ortho aminophenols to produce benzimidazoles or benzoxazole derivatives of galactosides, respectively. A similar procedure may be employed beginning with other hexose nitriles (Myers, et al.).

By the same procedures in Example 3B2, the aminophenol is reacted with the activated thioamide from the paragraph above to produce the benzoxazole which is further converted into the N-protected galactoside by the procedures in Example 3B2. This is converted into the morpholine nucleoside by the usual procedure except that twice the normal amount of periodate is employed in the oxidation step. The N-trityl group is introduced by the method in Example 3C1.

EXAMPLE 4

Preparation of 4-Membered High-Specificity Subunit Set Containing Morpholino Backbone Moieties (FIG. 6A)

A. C:G-specific Subunits

1. Subunit Containing Guanine Base (FIG. 10A). Guanosine is converted into its 2-phenylacetyl derivative by the method in Example 1. This is converted into the morpholine nucleoside tosylate salt by the methods in Example 2C. It may be tritylated by reaction with triphenylmethyl chloride in acetonitrile containing triethylamine. The reaction mixture is poured into water and the product filtered. The product is purified by recrystallization from acetonitrile.

2. Subunit containing the base of FIG. 24C. 3-Bromophenol was nitrated to give 5-bromo-2-nitrophenol, then the nitro group was reduced with Raney-Nickel (or hydrogen sulfide/pyridine) and the amine formylated with formic acetic anhydride. This was again nitrated and then the oxazole is formed by thermolysis. An alternate method of forming the unsubstituted oxazole ring involves removal of the formamide by ammonolysis and treatment of the aminophenol with the formylation reagent derived from phosphorous oxychloride/dimethylformamide. Other amides than formic may be used for the protection of this amino group during the nitraton, and that the oxazole synthesis with these species will produce substituted benxoxazoles. For example, the trifluoracetamide, formed using trifluoroacetic anhydride, will produce the trifluoromethyl benzoxazole. Finally, the nitro group was reduced and the amine protected as a 2-(trimethylsilyl)ethyl carbamate prior to coupling with the sugar. This product is the key intermediate for the introduction of the sugar moiety.

The glycosylation procedure employed follows the general method of Zimmermann and Stille for the coupling of vinyl stannanes with aromatic halides, and the method for the conversion of pyranoid glycals to the glucosyl derivatives by the method of Hanessian, et al. The bromide above (or appropriate aromatic halide in general) was reacted with the persilylated, C-1 stannylated pyranoid glycal (Hanessian, et al.) in the presence of tetrakis(triphenylphosphine)palladium(0). The enol ether was hydroborated with the borane-dimethyl sulfide complex in tetrahydrofuran and the resulting boron species decomposed to the alcohol by the addition of basic hydrogen peroxide. All the silylated alcohols and beta(trimethylsilyl)ethyl carbamates were deprotected with flouride ion.

In this example, the amino group may be reprotected as the trifluoroacetamide as in Example 1. The molecule was nitrated in acetic acid, the labile amide cleaved by ammonolysis, and the aminobenzimidazole prepared by reduction of the nitro group with hydrogen sulfide/- pyridine or stannous chloride with cyanogen bromide. Following protection of the aminobenzimidazole by the methods in Example 3A or Example 4Ciii, the morpholine moiety was then constructed as in Example 2C, except that two equivalents of sodium periodate are employed in the oxidation step.

3. Subunit containing the base of FIG. 24D. 2-Bromo-4-methylphenol was nitrated to produce the 6-nitrospecies. Following reduction with hydrogen sulfide in pyridine, the aminophenol was treated with cyanogen bromide to produce the aminobenzoxazole. Following conversion to the 2-(trimethylsilyl)ethyl carbamate, the bromine may be replaced by the appropriate glycosyl unit by coupling with the pyranoid glycal as in Example 4Aii. After the coupling sequence was completed, and the molecule fully desilylated, the amino group was protected as the trifluoro- or trichloroacetamide, and the molecule nitrated to produce the 4-nitro species. The 5-methyl group was now functionalized by reaction with dimethylformamide dimethylacetal to give the enamine by the general procedure (Mulzer, et al). Reduction of the nitro group with hydrogen sulfide/pyridine or with hydrogen and Pd/carbon, afforded the indole. As the protecting group on the aminobenzoxazole may be wholly or partially removed during the indole formation sequence, following ammonolysis to remove any amidine group, the trifluoro- or trichloroacetamide was reintroduced as in Example 1. Further functionalization of the indole was done by reaction with phosphorous oxychloride/dimethylformamide (Smith (1954)). The resultant formyl indole may be converted into the nitrile by reaction with hydroxylamine to give the oxime followed by treatment with trifluoroacetic anyhdride. The glucose containing subunit may be converted into the morpholino subunit by the procedure in Example 2C except that two equivalents of sodium periodate is used.

B. T:A or U:A-Specific Subunits

1. Subunit containing 2,6-diaminopurine base (FIG. 10B). 2,6-Diaminopurineriboside is converted into its N2-phenylacetyl N6-benzoyl derivative by the method in Example 1. This is converted into the morpholine nucleoside by the methods in Example 2C. It is tritylated by the procedure in Example 5A 2. Subunit containing the base of FIG. 26D. 2-Bromo-4-methylphenol was nitrated to produce the 6-nitrospecies. Following reduction with hydrogen sulfide in pyridine, the aminophenol was treated with cyanogen bromide to produce the aminobenzoxazole. Following conversion to the 2-(trimethylsilyl)ethyl carbamate, the bromine may be replaced by the appropriate glycosyl unit by coupling with the pyranoid glycal as in Example 4Aii. After the coupling sequence was completed, and the molecule fully desilylated, the amino group was protected as the trifluoro- or trichloroacetamide, and the molecule nitrated to produce the 4-nitro species. The 5-methyl group was now functionalized by reaction with dimethylformamide dimethylacetal to give the enamine by the general procedure (Mulzer, et al). Reduction of the nitro group with hydrogen sulfide/pyridine or with hydrogen and Pd/carbon, afforded the indole. As the protecting group on the aminobenzoxazole may be wholly or partially removed during the indole formation sequence, following ammonolysis to remove any amidine group, the trifluoro- or trichloroacetamide was reintroduced as in Example 1. Further functionalization of the indole was done by reaction with phosphorous oxychloride/dimethylformamide (Smith (1954)). The resultant formyl indole may be converted into the nitrile by reaction with hydroxylamine to give the oxime followed by treatment with trifluoroacetic anyhdride. The glucose containing subunit may be converted into the morpholino subunit by the procedure in Example 2C except that two equivalents of sodium periodate is used.

3. Subunit containing the base of FIG. 26E. 2-Bromo-4-chlorophenol was nitrated to yield the 6-nitro species. Following reduction with hydrogen sulfide in pyridine, the aminophenol was treated with cyanogen bromide to produce the aminobenzoxazole. Following conversion to the 2-(trimethylsilyl)ethyl carbamate, the bromine may be replaced by the appropriate glycosyl unit by coupling with the pyranoid glycal as in Example 4Aii. After the coupling sequence was completed, and the molecule completely desilylated, the amino group is protected as the trifluoro- or trichloroacetamide as in Example 1, and the chlorine removed by treatment with triphenyl- or tributyltin hydride and a radical initiator in xylene. The glucose containing subunit may be converted into the morpholino subunit by the procedure in Example 2C except that two equivalents of sodium periodate is used.

C. A:T or A:U-Specific Subunits

1. Subunit containing the base of FIG. 20B. 5-Hydroxy-2(3H)-benzoxazolone (Ozdowska) is acetylated with acetic anhydride and then nitrated with cold fuming nitric acid to the 6-nitro-5-acetoxy species. This is dissolved in ethanol and treated with potassium carbonate, than hydrogenated over palladium to reduce the nitro group to an amino group. The isolated aminophenol is reacted with an active thioamide derivative from Example 3C to give the 6-(2,3,4,6-tetra-O-acetyl-galactosyl)-oxazolo[4,5-f]-2(3H)-benzoxazolone. Reaction with phosphoryl chloride followed by ammonolysis gives the 2-aminobenzoxazole. This is N-protected by the usual procedure to prepare the benzoyl, isobutyryl, acetyl, methoxyacetyl, phenoxyacetyl or trichloroacetyl amides.

The morpholine nucleoside is prepared from the galactosyl species above by the procedures in Example 2C except with double the usual amount of sodium periodate in the oxidation step in order to form the dialdehyde used for reductive amination. The latter step is performed by the usual methods. The morpholine is tritylated as in Example 5A and purified by silica gel chromatography.

2. Subunit containing the base of FIG. 20C. 2-Methyl-4-hydroxybenzoic acid (King) is nitrated with cold fuming nitric acid to give the 5-nitro derivative which is reduced using palladium catalyst in a hydrogen atomosphere to the 5-amino species. This is converted into the methyl ester by the procedure in Example 3A1. This is converted to the 2-aminobenzoxazole using cyanogen bromide and the exocyclic amino group acylated by the methods in Example 1 with acetyl, methoxyacetyl, trichloroacetyl, isbutyryl or benzoyl. The compound is converted into the benzylic bromide by the methods in Example 3A1.

The morpholine nucleoside is prepared first by reaction of the benzylic bromide with beta-D-glucopyranosylamine as in Example 3C. Then, methanolic periodate cleavage using twice the usual amount of sodium periodate and reductive amination give the morpholine nucleoside. This is tritylated by the procedure in Example 5A and purified by silica gel chromatography.

Alternatively, the benzylic bromide is reacted with ammonia to produce the lactam which is O-silylated with trimethylsilyl trifluoromethanesulfonate or tert-butyldimethylsilyl trifluoromethanesulfonate and 2,6-di-tert-butylpyridine. The O-silylated lactam is reacted with tetraacetyl alpha-D-glucopyranosyl bromide (with our without the presence of silver trifluoromethanesulfonate or mercuric bromide), followed by ammonolysis and reprotection of the primary amino group as in Example 5C1. The glycoside is converted into the morpholine nucleoside in the usual way except that twice the normal amount of sodium periodate is employed. The morpholine is tritylated as in Example 5A and purified by silica gel chromatography.

3. Subunit containing the base of FIG. 22B. Alkyl 3-oxobutanoates were prepared by reaction of an alcohol with diketene. These were converted to the corresponding alkyl 2-(hydroxyimino)-3-oxobutanoates according to the general procedure for the ethyl ester (Touster, 1975). This was reduced and acylated with the corresponding alkyl chloroformate (or related acylating species, eg the azidoformate or p-nitrophenylcarbonate) using the general procedure described for the ethyl ester in (Fernandez-Resa, et al, 1989), to provide alkyl 2-(alkyloxycarbonylamino)-3-oxobutanoates. By these procedures, carbamate derivatives of 2-amino-3-oxobutanoates are available wherein the ester and carbamate have identical alkyl substituents. By this design, cleavage of the carbamate and ester groups may be performed simultaneously. Examples of alkyl groups which are available are benzyl (removed by hydrogenolysis), 2-(trimethylsilyl)ethyl (removed by hydrogen fluoride/pyridine), o-nitrobenzyl (removed by photolysis).

To a strirred suspension of sodium hydride (3.0 mmol) in DMF (20 mL) under argon was added benzyl 2-(benzyloxycarbonylamino)-3-oxobutanoate (3.6 mmol) in dimethylformamide (10 mL). The solution of the anion was treated with 6-chloro-9-(2',3', 5'-tri-O-benzoyl-D-ribofuranosyl)purine (3 mmol, prepared as in Satoda, et al) by the general method of Hamamici and Miyasaka. The adduct (1 mmol) was dissolved in ethyl acetate/ethanol (20 (mL) containing acetic acid (1 ml) and 5% Pd/carbon (200 mg). The mixture was shaken in a Paar apparatus under 45 psi hydrogen gas. After filtration through celite, the solution was treated with toluenesulfonic acid (1 mmol) and evaporated to dryness. The product was precipitated by dissolving in ethyl acetate/ethanol and pouring into ether/hexane mixtures. This product is also available from other adducts of 2-amino-3-oxobutanoates with chloropurines wherein the ester/carbamate is protected with different alkyl groups, some of which are listed in the preceeding paragraph. For example, if the 2-(trimethylsilyl)ethyl group is utilized it may be cleaved by reaction in pyridine containing hydrogen fluoride and/or tetrabutylammonium fluoride. The latter reagent may also be satisfactorily employed in tetrahydrofuran.

The amine tosylate (1 mmol) was dissolved in dimethylformamide (15 mL) and treated with diisopropylamine (3 mmol) and cyanogen bromide (1 mmol). The solvent was evaporated, the residue dissolved in dichloromethane and washed with sodium bicarbonate solution, water and brine. After removal of solvent, the residue was redissolved in dimethylformamide and treated with 1,8-diazabicyclo[5.4.0]undec-7-ene. The solvent was evaporated and the residue dissolved in dichloromethane, and washed with pH=7 phosphate buffer, water and then dried over sodium sulfate. Evaporation yields the imidazo[5,1-i]purine which may be purified by chromatography using chloroform/methanol mixtures.

The imidazo[5,1-i]purine (1 mmol) is dissolved in a methanol/dimethylformamide mixture and treated with 1,3-diaminopropane (20 mmol) at room temperature. After several hours at ambient temperatures, the mixture was heated in a sealed vessel to complete the removal of the benzoate esters. Alternatively, the rearrangement to the pyrido[2,3-d:4,5-d']diimidadzole and hydrolysis may be affected with 2M sodium hydroxide in dimethylsulfoxide.

The C-8 oxo group was introduced by the general procedure of Ikehara and Kaneko, which involves bromination of the benzimidazole followed by mild hydrolysis with aqueous acetate. This and other tautomeric aminobenzimidazole moieties may be protected on the reactive amino and benzimidazole type nitrogens as was done in Example 3A. Alternatively, the trifluoroacetamide was prepared by using the transient protection procedure for alcohols from Example 1 (trimethylsilyl chloride and pyridine) and reacting the silylated species with trifluoroacetic anhydride to acylate the exocylic amino group. A similar reaction scheme will produce the trichlroacetamide. The benzimidazole type ring nitrogen may then be protected by a following reaction, again using the transient protection procedure, with p-toluenesulfonyl chloride in pyridine. In this latter reaction, two tautomeric sulfonated products may be obtained, but their separation is not essential.

A nontautomeric aminobenzimidazole may be prepared by methylation of the aminobenzimidazole moiety at an appropriate time. For example, the species produced in the preceeding paragraph was dissolved in DMSO and treated with methyl iodide and potassium hydroxide to give the methylated species. This product may also be obtained by the alkylation of the aminobenzimidazole moiety prior to introduction of the oxo group.

The ribose linked species from QB may be converted into the morpholine nucleoside by the procedure in example 2C.

Subunits containing a deoxyribose moiety may be prepared if the initial chloropurine employred is linked to a deoxyribose. Thus, the tri-O-benzoyl derivative of 6-chloropurinedeoxyriboside (prepared by benzoylation ofthe free hydroxyl species; Robins and Basom (1978)) is employed for reaction with the aminoacetoacetate.

4. Subunit containing the base of FIG. 30C. 3-Bromophenol was nitrated to produce 5-bromo-2-nitrophenol. This was reduced with hydrogen sulfide/pyridine to the aminophenol, and the amino group masked as the trifluoroacetamide. A second nitration produced the 4-nitrophenol species which was treated with ammonia to cleave the trifluoroacetamide. This was reacted with cyanogen bromide to produce the aminobenzoxazole which is protected as the trifluoroacetamide. The nitro group was reduced with pyridine hydrogen sulfide and the amine treated with ethyl chloroformate to generate the carbamate. Nitration, nitro reduction, and heating provided the fused imidazolone. Ammonolysis of the trifluoroacetamide gave the aminobenxoxazole which was protected as the beta(trimethylsilyl)ethylcarbamate. This was coupled with the pyranoid glycal as in Example 4Aii to produce the subunit with the glucose moiety. Following complete desilylation, the amino group was protected as the trifluoro- or trichloroacetamide as per Example 1. The glucosyl subunit may be converted into the morpholine containing subunit by the method of Example 2C except that two equivalents of sodium periodate is employed in the oxidation step.

5. Subunit containing the base of FIG. 30F. 3-Bromophenol was nitrated to produce 5-bromo-2-nitrophenol. This was reduced with hydrogen sulfide/pyridine or stannous chloride to the aminophenol. This was reacted with cyanogen bromide to produce the aminobenzoxazole, which was protected as the 2-(trimethylsilyl)ethylcarbamate. This was coupled with the pyranoid glycal as in Example 4Aii to produce the subunit with the glucose moiety. Following complete desilylation of the molecule, the amino group was protected as the trifluoro- or trichloroacetamide as per Example 1. The glucosyl subunit may be converted into the morpholine containing subunit by the method of Example 2C except that two equivalents of sodium periodate is employed in the oxidation step.

D. G:C-Specific Subunits

1. Subunit containing the base of FIG. 15C. 5-Chloro-2,4-dinitrophenol (Carnelley, et al.) is treated with chloromethyl benzyl ether and diisopropylethyl amine, and the ether is treated with the sodium salt of methyl cyanoacetate (or malononitrile) followed by reduction with iron in acetic acid. Cleavage of the acetal (hydrogen/palladium on carbon) and reaction with an activated thioimide derivative from Example 3C produces the pyrrolobenzoxazole which, after ammonolysis, may be base protected by the procedure in Example 1 to prepare the benzoyl, isobutyryl, acetyl, methoxyacetyl, phenoxyacetyl or trichloroacetyl amides.

The morpholine nucleoside is prepared by reaction of the galactoside with double the usual amount of sodium periodate in order to form the dialdehyde used for reductive amination. The latter step is performed by the usual methods. The molecule is tritylated by the method in Example 5A and purified by silica gel chromatography.

2. Subunit containing the base of FIG. 15B. 4-Chloro-2-methylbenzoic acid (Pfaltz and Bauer Chemical Co.) is converted into its methyl ester (HCl/methanol) and further converted into the benzylic bromide by the procedure in Example 3C. Reaction with two equivalents of ammonia provides the lactam which is nitrated in fuming nitric acid to give the 4-nitro-5-chloro-2-oxoisoindole.

The lactam from above is O-silylated as in Example 5C2. The lactim ether is reacted with tetraacetyl alpha-D-glucopyranosyl bromide (with or without the presence of silver trifluoromethanesulfonate or mercuric bromide). This is reacted the sodium salt of methyl cyanoacetate (or malononitrile) followed by reduction with iron in acetic acid. The acyl groups are all removed by ammonolysis and the base reprotected by the usual procedure as the benzoyl, isobutyryl, acetyl, methoxyacetyl, phenoxyacetyl or trichloroacetyl amides.

Alternatively, 4-chloro-2-methylbenzoic acid is nitrated with fuming nitric acid in concentrated sulfuric acid to give the 5-nitro derivative. Following esterification by the method in Example 3A, this is reacted with the sodium salt of methyl cyanoacetate (or malononitrile) followed by reduction with iron in acetic acid. The amine is protected by reaction with trichloroacetic anhydride, methoxyacetic anhydride, acetic anhydride, isobutyryl chloride or benzoyl chloride. This is converted into the benzylic bromide by the methods in Example 3C. The benzylic bromide is converted into the lactam glucoside by treatment with beta-D-glucopyranosylamine.

The glucoside above is reacted with methanolic periodate using twice the usual amount of sodium periodate followed by reductive amination to give the morpholino nucleoside. This is tritylated by the procedure in Example 5A and purified by silica gel chromatography.

3. Subunit containing the base of FIG. 17C. 5-Formyl-2'-deoxyuridine (Barwolff and Langen) is dissolved in methanol and treated with manganese dioxide in the presence of sodium cyanide and acetic acid according to the general procedure of Corey, et al. to provide the methyl ester. The ester is reacted with tert-butyldimethylsilyl triflate in dichloromethane in the presence of diisopropylethyl amine to protect the alcohols. The heterocycle is activated by the method of Bischofberger (NaH, triisopropylbenzenesulfonyl chloride, THF). The 4-O-sulfonated heterocycle is treated with the tosylate salt of benzhydryl alanine (Aboderin, et al.) in the presence of diisopropylethyl amine in DMF to give the cytosine derivative. The cytosinyl alanine derivative is oxidized to the dehydroamino acid by the general procedure of Poisel and Schmidt (tert-butyl hypochlorite in THF, followed by one equivalent of potassium tert-butoxide in THF). The product is treated with a catalytic amount of potassium tert-butoxide in hot THF to provide the pyrimidopyridine. The benzhydryl ester is removed by hydrogenolysis using hydrogen over palladium/carbon. The acid is treated with diphenylphosphoryl azide in benzyl alcohol (or benzyl alcohol/dioxane) containing triethylamine according to Shioiri, et al. Following hydrogenolysis to cleave the carbamate, and HF-pyridine to remove the silyl groups, the molecule is N-protected as the trichloroacetamide or phenylacetamide by the usual procedure.

In a similar manner, 5'-formyluridine, prepared from 5-methyluridine by the procedures in Barwolff and Langen, is converted into the corresponding pyrimidopyridine riboside. The riboside is converted into the morpholine nucleoside by the usual procedure, and protected as the N-trityl derivative.

5. Subunit containing the base of FIG. 18B. The imidazo[5,1-i]purine (1 mmol) was prepared as in example 4Ciii and dissolved in a methanol/dimethylformamide mixture and treated with 1,3-diaminopropane (20 mmol) at room temperature. After several hours at ambient temperatures, the mixture was heated in a sealed vessel to complete the removal of the benzoate esters. Alternatively, the rearrangement and hydrolysis may be affected with 2M sodium hydroxide in dimethylsulfoxide.

This and other tautomeric aminobenzimidazole moieties in this disclosure may be protected on the reactive amino and benzimidazole nitrogens as was done in Example 3A. Alternatively, the trifluoroacetamide may be prepared by employing the transient protection procedure for alcohols from Example 1 (trimethylsilyl chloride and pyridine) and reacting the silylated species with trifluoroacetic anhydride to acylate the exocylic amino group. A similar reaction scheme will produce the trichlroacetamide. The benzimidazole type nitrogen may then be protected by a following reaction, again using the transient protection procedure, with p-toluenesulfonyl chloride in pyridine. In this latter reaction, two tautomeric sulfonated products may be obtained, but their separation is not essential.

The ribose above may be converted into the morpholine nucleoside by the procedure in example 2C.

The preparation of subunits containing the deoxyribose moiety can be achieved if the initial chloropurine used contains a deoxyribose. Thus, the tri-O-benzoyl derivative of 6-chloropurinedeoxyriboside (prepared by benzoylation of the free hydroxyl soecies obtained from Robins and Basom) is employed in the coupling with the aminoacetoacetate derivative.

An alternative entry into compounds of this structural type, which allows for the placement of substituents at the benzimidazole carbon other than hydrogen, is as follows. 4,6-Dichloro-5-nitropyrimidine was reacted with beta-1-amino-2,3,4,6-tetra-O-pivaloyl-D-galactose (Kunz and Pfrengle). The monoadduct was reduced with Raney-Nickel and hydrogen gas to the 5-amino pyrimidine species. This was converted into the 5-acylamino species by reaction with the corresponding acid anhydride or acid chloride, or other acid derivative in pyridine. Thermolysis of the amide (30–200) provided the 6-chloro-8-substituted-9-galactosylpurine. For example, reaction of the amine with difluorothioacetyl fluoride (Martin) yields an intermediate thioamide which was readily cyclized to the difluoromethyl benzimidazole moiety.

These species may then be treated with an alkyl 2-(alkyloxycarbonylamino)-3-oxobutanoate and carried on as above to prepare the galactosyl substituted series. The pivaloyl groups were removed in the rearrangement step of the imidazo[5,1-i]purine to the pyrido[2,3-d:4,5-d']diimidazole, as were the benzoyl groups in the ribosyl series. Conversion of the final galactosyl substituted subunit into the morpholine subunits was done as per Example 2C except that 2 equivalents of sodium periodate is used.

Other glycosylamines may be employed in the reaction with the dichloronitropyrimidine. Examples include the tetrabenzoates of both beta-D-glucosylamine and beta-D-galactosylamine (Caballero, et al).

5. Subunit Containing the Base of FIG. 31C. 4-Chloro-3-nitrophenol was brominated to produce the 6-bromo species and reacted with dimethoxymethane and tosic acid in dichloromethane by the method of Yardley and Fletcher to produce the methoxymethyl ether. The ether was then treated with the sodium salt of ethyl cyanoacetate in ethanol and the product reduced with iron filings in acetic acid to provide the amino indole ester. Water was added to produce an 80% acetic acid mixture and the suspension heated. After filtration of the iron and removal of the solvent, the amino group was protected as the 2-(trimethylsilyl)ethyl carbamate by the procedures in Example 1 (transient protection). The phenol was nitrated with nitric acid/acetic anhydride, the nitro reduced with hydrogen sulfide/pyridine, and the oxazole formed as in example 4Aii. Examples of substituents which may be incorporated onto the oxazole carbon are hydrogen, methyl, difluoromethyl, and trifluoromethyl. The bromo aromatic was coupled to the pyranoid glycal to produce the subunit with the glucose moiety. After complete desilylation of the molecule, the amino pyrrole was protected as the trifluoro- or trichloroacetamide as per Example 1. The glucosyl subunit may be converted into the morpholine containing subunit by the method of Example 2C except that two equivalents of sodium periodate is employed in the oxidation step.

6. Subunit Containing the Base of FIG. 31D. 3-Fluoro-4-nitrophenol was reacted with dimethoxymethane and tosic acid in dichloromethane by the method of Yardley and Fletcher to produce the methoxymethyl ether. The ether was the treated with the sodium salt of ethyl cyanoacetate in ethanol and the product reduced with iron filings in acetic acid to provide the amino indole ester. Water was added to produce an 80% acetic acid mixture and the suspension is heated. After filtering the iron, and removal of the solvent, the amino group was protected as the 2-(trimethylsilyl)ethyl carbamate by the procedures in Example 1 (transient protection). The phenol was reacted with trifluoromethanesulfonic anhydride and the triflate coupled to the pyranoid glycal by the method in Example 4Aii to produce the subunit with the glucose moiety. Following complete desilylation of the molecule, the amino pyrrole was protected as the trifluoro- or trichloroacetamide as per Example 1. The glucosyl subunit may be converted into the morpholine containing subunit by the method of Example 2C except that two equivalents of sodium periodate is employed in the oxidation step.

EXAMPLE 5

Preparation of 4-Membered High-Specificity Subunit Set Containing N-Carboxymethylmorpholino-5'-amino Backbone (FIG. 6C)

Subunits containing ribose, galactose, or glucose moieties are prepared as in Example 4, and their respective sugar moieties are converted to the N-Carboxymethylmorpholino-5'-tritylated amine form by the method described in Example 2D.

EXAMPLE 6

Polymer Assembly Procedures for 2'-O-Methylribose (FIG. 5B) and 2'-Deoxyribose-containing (FIG. 5A) subunits The protected 2'-Deoxyriboside-containing subunits and the protected 2'-O-Methylriboside-containing subunits are converted into their corresponding 3'-H-phosphonate salts by the methods given in Sakataume, et al. and polymerized on solid support by the method in this source. When the assembly of the polymer chain is complete, the supported molecule is treated with a primary or secondary amine in the presence of either iodine or carbon tetrachloride as per the method of Froehler. The phosphoramidate-linked polymer is removed from the support and deprotected by the usual methods involving ammonolysis (Froehler).

EXAMPLE 7

Representative Activation Procedures for Morpholino-Containing Subunits

A. Activation of 5'-Hydroxyl of Morpholino Subunit

Dimethylaminodichlorophosphate is prepared as follows: a suspension containing 0.1 mole of dimethylamine hydrochloride in 0.2 mole of phosphorous oxychloride is refluxed for 12 hours and then distilled (boiling point is 36° C. at 0.5 mm Hg).

Activation of the 5'Hydroxyl of a morpholino-containing subunit prepared as in Example 2C entails dissolving one mmole of 5'hydroxyl subunit, baseprotected and tritylated on the morpholino nitrogen, in 20 ml of dichloromethane. To this solution 4 mmole of N,N-diethylaniline and 1 mmole of 4-methoxypyridine-N-oxide are added. After dissolution, 2 mmole of dimethylaminodichlorophosphate is added. After two hours the product is isolated by chromatography on silica gel developed with 10% acetone/90% chloroform. The same procedure, except substituting ethyldichlorothiophosphate instead of dimethylaminodichlorophosphate, gives an activated subunit with similar utility.

B. Activation of 5'-Amine of Morpholino-Containing Subunit

The 5'hydroxyl of a morpholino-containing subunit, having exocyclic amino groups of the base-pair recognition moiety in the protected form, prepared as in Example 2C can be converted to the amine as follows. To 500 ml of DMSO is added 1.0 mole of pyridine (Pyr), 0.5 mole of triflouroacetic acid (TFA), and 0.1 mole of the morpholino subunit. The mixture is stirred until dissolved, and then 0.5 mole of diisopropylcarbodiimide (DIC) or dicyclohexylcarbodiimide (DCC) is added. After 2 hours the reaction mixture is added to 8 liters of rapidly stirred brine, which is stirred for 30 minutes and filtered. The solid is dried briefly, washed with 1 liter of ice cold hexanes, filtered, and the solid is added to 0.2 mole of sodium cyanoborohydride in 1 liter of methanol, stirred for 10 minutes, 0.4 mole of benzotriazole or p-nitrophenol is added, followed by 0.2 mole of methylamine (40% in $H_2O$) and the preparation is stirred four hours at room temperature [Note: the benzotriazole or p-nitrophenol buffers the reaction mixture to prevent racemization at the 4' carbon of the subunit at the iminium stage of the reductive alkylation]. Finally, the reaction mixture is poured into 5 liters of water, stirred until a good precipitate forms, and the solid is collected and dried. This dried product is next suspended in DMF and 4 equivalents of $SO_3$/pyridine complex is added. Over a period of several hours, 8 equivalents of triethylamine is added dropwise with stirring. After an additional two hours the preparation is dumped into a large volume of brine and the solid collected by filtration and dried. This sulfamic acid preparation is then purified by silica gel chromatography.

Ten mmole of the triethylamine salt of sulfated subunit protected on the recognition moiety and on the nitrogen of the morpholino ring is dissolved in 10 ml of dichloromethane and then 40 mmole of pyridine is added. This solution is chilled for 15 minutes on a bed of dry ice and then 1.1 mmole of phosgene (20% in Toluene) is slowly added while the solution is rapidly stirred. After addition, the solution is allowed to come to room temperature and then washed with aqueous $NaCHO_3$,- dried, and chromatographed on silica gel eluted with a mixture of chloroform and acetone to give the desired sulfamoyl chloride.

C. Activation of Annular Morpholino Nitrogen

This example describes the preparation of a morpholino subunit protected on its 5' oxygen and sulfated on its morpholino ring nitrogen. Morpholino-containing subunit prepared as in Example 2C, but not carried through the last tritylation step, is silylated on its 5' hydroxyl with t-butyldimethlsilyl chloride. This product is then treated with $SO_3$/pyridine complex (with excess pyridine) in dimethylformamide (DMF) to give a sulfamic acid on the annular morpholino nitrogen.

It should be mentioned that the salts of sulfamic acids can be chromatographed on silica gel using triethylamine/methanol/chloroform mixtures if the silica is first pre-eluted with 2% triethylamine in chloroform.

This sulfamic acid on the morpholino nitrogen is converted to the sulfamoyl chloride and purified as in Example 7B above.

D. Activation of N-Carboxymethyl of Morpholino

Carboxylate-containing subunits, such as prepared in Examples 2D and 2E, are activated as follows. Ten mmole of the subunit is dissolved in DMF containing 20 mmole of p-nitrophenol and 15 mmole of dicyclohexylcarbodiimide. After 1 hour the product is rotovaped and then purified by silica gel chromatography developed with a mixture of acetone and chloroform.

EXAMPLE 8

Representative Solid-Phase Polymer Assembly of Morpholino-containing Subunits (FIG. 33)

This example describes a method which is generally applicable for assembly of activated subunits, prepared as in Examples 7A and 7B, to give phosphorodiamidate-linked, ethylthiophosphoramidate-linked, and sulfamate-linked binding polymers. A similar scheme wherein the coupling step includes the addition of silver trifluoromethanesulfonate, and use of N,N-diisopropyl-2-methoxyethylamine instead of diisopropylethanolamine, is suitable for assembly of subunits prepared as in Example 7C to give sulfamate-linked polymers. A similar scheme, wherein the coupling step is carried out in dimethylformamide instead of dichloromethane, is suitable for assembly of subunits activated as in Example 7D to give amide-linked polymers.

A. Linker

Aminomethyl polystyrene resin (Catalog no. A1160, from Sigma Chemical Co.) 1% divinylbenzene cross-linked, 200 to 400 mesh, 1.1 mMole of N per gram, is suspended in dichloromethane and transferred to a 1 cm diameter column having a frit on the bottom, to give a resin bed volume of 2.5 ml.

One mMole of bis[2-(succinimidooxycarbonyloxy)ethyl]sulfone (Pierce Chemical Co. of Rockford, Ill. USA) is added to a dichloromethane solution containing 1 mMole of N-tritylated piperazine. After 2 hours the reaction mixture is chromatographed on silica gel developed with an acetone/chloroform mixture to give a mono-activated beta-elimination-cleavable linker.

134 MicroMole of the above linker is dissolved in 1 ml of dichloromethane and added to the resin in the synthesis column and the resin suspension agitated for 3 hours at 30° C. Next, 1 mMole of diisopropylaminoethanol and 1 mMole of acetic anhydride is added and agitation continued for 10 minutes, followed by addition of 2 mMole of benzylmethylamine and agitation for 20 minutes. The column is washed with 30 ml dichloromethane. Based on release of trityl, the above procedure typically gives on the order of 100 to 110 micromoles of bound linker.

B. Coupling Cycle (Detritylation/Coupling/Capping)

The coupling cycle described below is used for adding each subunit in an order appropriate to give a polymer having the desired sequence of subunits.

1. Detritylation. Add a solution containing 53 ml of dichloromethane, 6 ml of trifluoroethanol, and 1 gram of cyanoacetic acid. After this solution has passed through, wash the column with 40 ml of dichloromethane, followed by 20 ml of dichloromethane containing 4 mMole of diisopropylaminoethanol. Wash the column with 10 ml of dichloromethane.

2. Coupling. Add 1 ml of dichloromethane containing 120 microliter of diisopropylaminoethanol to 0.25 mMole of activated subunit (prepared as in Example 7A or 7B) and add to the column and agitate at 37° C. for 1 hr. Wash the column with 30 ml dichloromethane. Note: excess unreacted activated subunit can be conveniently recovered simply by adding 4 volumes of hexane to this eluant and filtering.

3. Capping. Add to the column 2 ml of dichloromethane containing 1 mMole of diisopropylaminoethanol and 1 mMole of acetic anhydride and agitate at 37° C. for 10 minutes. Add to the column 10 ml of dichloromethane containing 1 mMole of benzylmethylamine, and agitate the resin bed at 37° C. for 20 min. Wash the column with 30 ml dichloromethane.

C. Cleavage from support and deprotection

After all the subunits have been added by the above coupling procedure, the full length polymer is cleaved from the support by eluting the column with a solution consisting of 2.5 ml of diethylmalonate, 5 ml of 1,8-diazabicyclo[5.4.0]undec-7-ene, and 43 ml dichloromethane. The polymer is then precipitated from this eluant by adding ether.

If it is desirable to add a moiety to enhance aqueous solubility, or to enhance target binding affinity, or to facilitate uptake by specific cell or tissue types, then the secondary aliphatic amine generated upon cleavage from the polystyrene support provides a site for attachment of such moieties at this stage of the polymer preparation.

The polymer product is next dissolved in DMF and an equal volume of conNH$_4$OH added, the preparation capped tightly, and incubated 18 hrs at 37° C. Subsequently, the preparation is dried under reduced pressure to give a polymer preparation wherein the base-pair recognition moieties are deprotected and at one end of the polymer is a trityl moiety, and at the other end is a secondary aliphatic amine which, as noted above, may be derivatized prior to the ammonia treatment.

EXAMPLE 9

Polymer Purification Methods

The full-length polymer having a terminal trityl moiety (typically greater than 50% of the total mass of the preparation for a 24-subunit long polymer) can be separated from the capped failure sequences by low pressure chromatography on a column of chromatographic grade polypropylene (Catalog No. 4342 from Poly-Sciences Inc.) developed with an acetonitrile/water gradient, with the eluant monitored photometrically at 254 nm. Purifications are typically performed using the following conditions: the polymer is suspended in water, the solution adjusted to pH 11 with dimethylamine and the eluting solvents also adjusted to pH 11 with dimethylamine. In this system, the tritylated full-length polymer elutes appreciably later than the non-trityl-containing capped failure sequences.

The fractions containing full-length polymer are collected and dried down under reduced pressure. The polymer preparation is then detritylated by suspending in trifluoroethanol (1 g polymer in 25 ml TFE) and 1.5 ml of mercaptoacetic acid added. After 10 minutes, 100 ml of ether is added and the final pure product collected by centrifugation or filtration.

EXAMPLE 10

Polymer Assembly Via Novel Oxidation/Ring Closure/Reduction Method (FIG. 39)

A. Synthesis Support

The solid support used in this synthesis should be hydrophilic, but should not contain vicinyl hydroxyls. Add an aqueous slurry of "MACRO-PREP 50 CM" (Catalog No. 156-0070 from Bio-Rad Laboratories, Richmond, Calif., USA) to a fritted column to give a 5 ml packed bed volume (containing approximately 1 mMole of carboxylate). Wash this synthesis support with 100 ml of 0.1N HCl and then 50 ml water. Pass 50 ml of DMF (dimethylfoyrmamide) through the column and drain. Add 5 ml of DMF containing 5 mMole of diisopropylcarbodiimide and 5 mMole of p-nitrophenol and incubate with agitation at 30° C. for 3 hours. Wash the column with 100 ml of DMF and then add 20 mMole of piperazine in 10 ml of DMF and agitate for 15 minutes. Wash the column with 50 ml of DMF and drain.

B. Addition of Linker and First Subunit

To 1 mMole of a ribose-containing subunit having a carbazate moiety at the 5' of the ribose (prepared as in Example 2F) in 5 ml of DMF, add 3 mMole of Bis[2-(succinimidooxycarbonyloxy)-ethyl]sulfone (Pierce Chemical Co. of Rockford, Ill., USA) and incubate at 30° C. for 3 hours. To the reaction mixture add ether and collect the precipitate. Wash the precipitated linker-subunit with ether, resuspend in 5 ml of DMF, add to the synthesis support, and incubate with agitation for 3 hrs at 30° C. Wash the support with 50 ml of DMF, and then with 100 ml of water.

C. Coupling Cycle

1. Oxidation of Vicinyl Hydroxyls. Dissolve 5 mMole of sodium periodate in 10 ml of water, add to column, and agitate for 10 minutes. Wash column with 50 ml of water and drain.

2. Morpholino Ring Closure/Reduction. Dissolve 2 mMole of sodium cyanoborohydride in 5 ml of water, adjust pH to between 7 and 8 with trimethylacetic acid, add 1.5 mMole of the next ribose-containing 5'-carbazate subunit, and add to the column containing the synthesis support. Incubate with agitation for 30 min at 30° C. Add formic acid to reduce pH to between 3 and 4, and incubate at 30° C. for 10 minutes. Wash column with 100 ml of water.

Repeat this coupling cycle until all subunits have been added to give the desired full-length polymer.

3. Addition of Terminal Moieties. If it is desirable to add to the binding polymer a moiety to enhance aqueous solubility, or to enhance target binding affinity, or to facilitate uptake by specific cell or tissue types, this can be conveniently achieved at this stage by oxidizing the vicinyl hydroxyls of the terminal subunit of the polymer and, by the morpholino ring closure/reduction procedure described above, adding said moieties containing a primary aliphatic amine.

4. Cleavage from the Support. After all the subunits of the polymer, and any desired additional groups, have been added by the above coupling procedure, the polymer is cleaved from the support by washing the column with 50 ml of DMF, and then eluting the column with a solution consisting of 2.5 ml of diethylmalonate, 5 ml of 1,8-diazabicyclo[5.4.0]undec-7-ene, and 43 ml of DMF. The polymer is then precipitated from this eluant by adding ether.

The full-length polymer can be purified by low pressure chromatography on a column of chromatographic grade polypropylene (Catalog No. 4342 from Poly-Sciences Inc.) developed with an acetonitrile/water gradient, with the eluant monitored photometrically at 254 nm. Purifications generally go better when the polymer is suspended in water and then the solution adjusted to pH 11 with dimethylamine and the eluting solvents also adjusted to pH 11 with dimethyl amine.

Although the invention has been described with respect to particular polymer subunits, methods of preparing the subunits, and polymer assembly, it will be appreciated that various modifications and changes may be made without departing from the invention.

It is claimed:

1. A polymer composition effective to bind in a sequence-specific manner to a target sequence of a duplex polynucleotide containing at least two different-oriented Watson/Crick base-pairs at selected positions in the target sequence, comprising a specific sequence of subunits having the form:

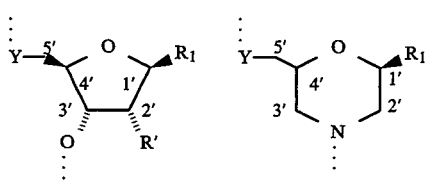

where Y is a 2- or 3-atom length, uncharged intersubunit linkage group; R' is H, OH, or O-alkyl; the 5'-methylene has a $\beta$ stereochemical orientation in the 5-membered ring and a uniform stereochemical orientation in the 6-membered ring; $R_i$ has a $\beta$ stereochemical orientation; and at least about 70% of $R_i$ groups in the polymer are selected from two or more of the following base-pair-specificity groups:

(a) for a T:A or U:A oriented base-pair, $R_i$ is selected from the group consisting of planar bases having the following skeletal ring structures and hydrogen bonding arrays, where B indicates the polymer backbone:

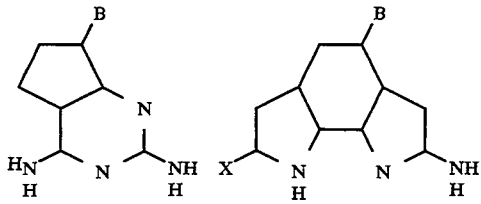

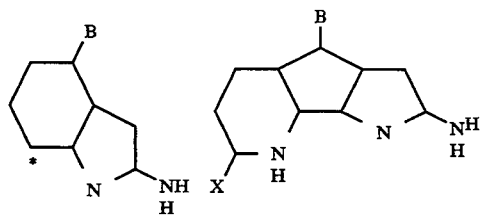

where the * ring position may carry a hydrogen-bond donor group, such as an amine; and X may be a moiety effective to afford discriminative binding on the basis of the moiety at the 5 position of the pyrimidine of the target base-pair;

(b) for a C:G oriented base-pair, $R_i$ is selected from the group consisting of planar bases having the following skeletal ring structures and hydrogen bonding arrays, where B indicates the polymer backbone:

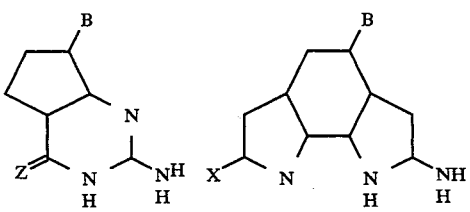

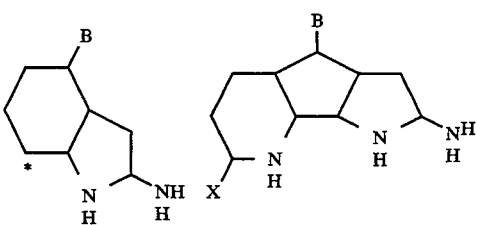

where the * ring position may carry a hydrogen-bond acceptor group, such as a carbonyl oxygen; X may be a moiety effective to afford discriminative binding on the basis of the moiety at the 5 position of the pyrimidine of the target base-pair; and Z is oxygen or sulfur;

(c) for a G:C oriented base-pair, $R_i$ is selected from the group consisting of planar bases having the following skeletal ring structures and hydrogen bonding arrays, where B indicates the polymer backbone:

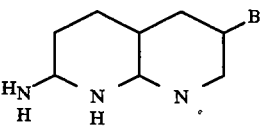

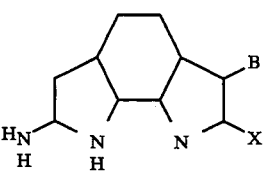

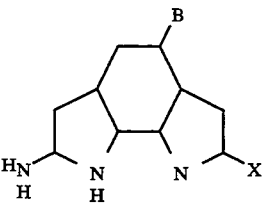

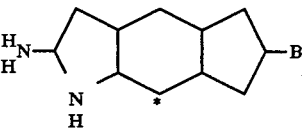

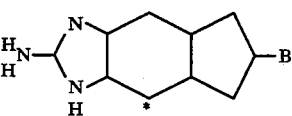

-continued

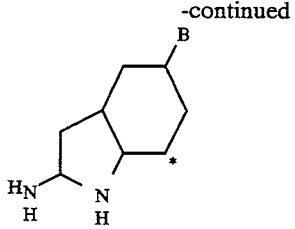

where the * ring position may carry a hydrogen-bond acceptor group, such as a carbonyl oxygen; and X may be a moiety effective to afford discriminative binding on the basis of the moiety at the 5 position of the pyrimidine of the target base-pair; and, (d) for an A:T or A:U oriented base-pair, $R_i$ is selected from the group consisting of planar bases having the following skeletal ring structures and hydrogen bonding arrays, where B indicates the polymer backbone:

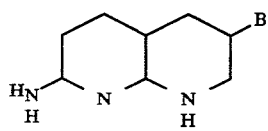

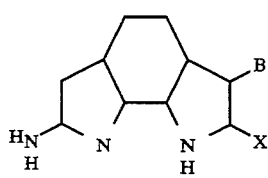

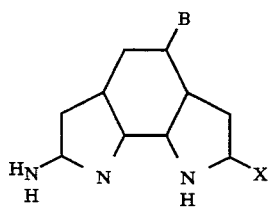

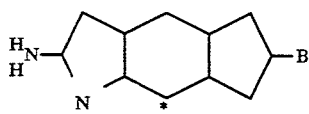

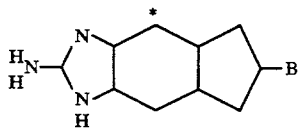

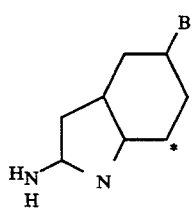

where the * ring position may carry a hydrogen-bond donating group, such as $NH_2$; and X may be a moiety effective to afford discriminative binding on the basis of the moiety at the 5 position of the pyrimidine of the target base-pair.

2. The polymer composition of claim 1, containing one or more subunits of the form:

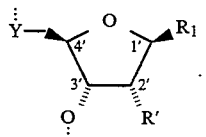

3. The polymer composition of claim 1, containing one or more subunits of the form:

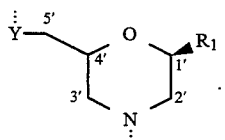

4. The polymer composition of claim 3, containing one or more subunits of the form:

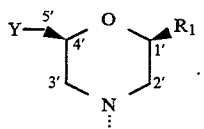

5. The polymer composition of claim 1, for use in sequence-specific binding to a B-form DNA-DNA duplex nucleic acid, wherein the Y linkage groups is three atoms in length.

6. The polymer composition of claim 5, wherein one or more subunits of the polymer are selected from the group consisting of:

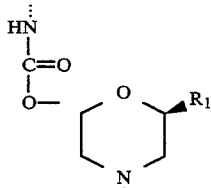

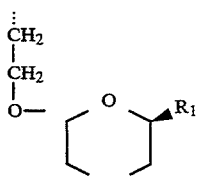

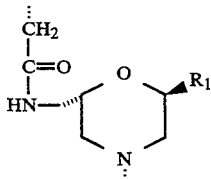

-continued

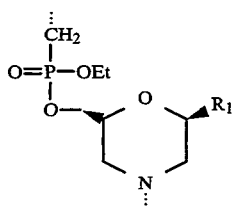

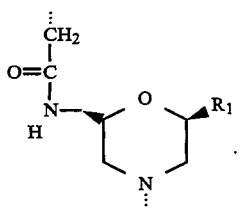

7. The polymer composition of claim 6, wherein one or more subunits of the polymer are selected from the group consisting of:

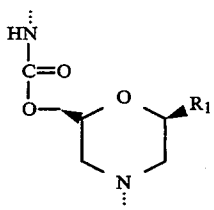

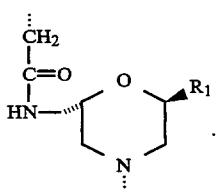

8. The polymer composition of claim 1, for use in sequence-specific binding to an A-form duplex nucleic acid, wherein the Y linkage group is two atoms in length.

9. The polymer composition of claim 8, wherein one or more subunits of the polymer are selected from the group consisting of:

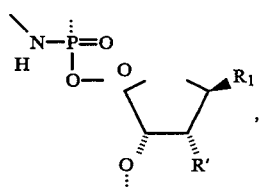

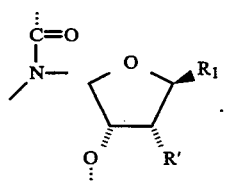

10. The polymer composition of claim 8, wherein one or more subunits of the polymer are selected from the group consisting of:

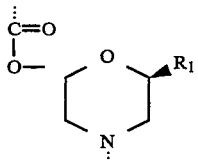

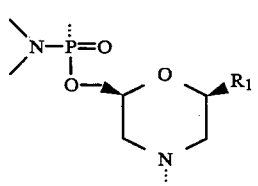

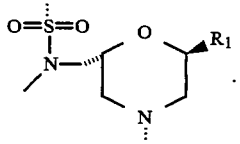

11. The polymer composition of claim 1, which contains at least one $R_i$ structure selected from the group consisting of:

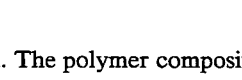

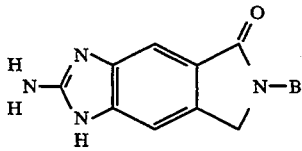

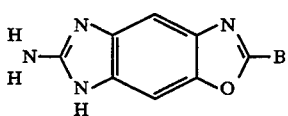

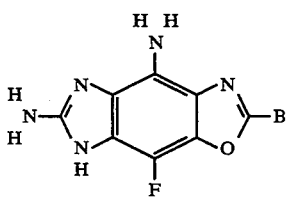

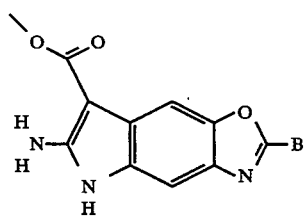

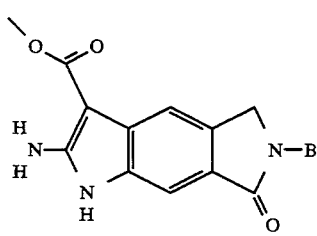
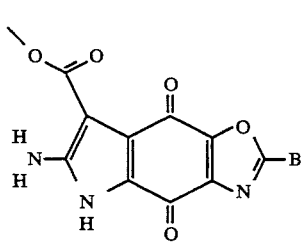
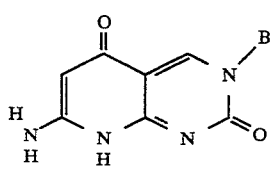
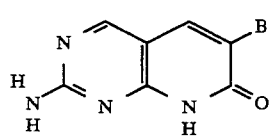
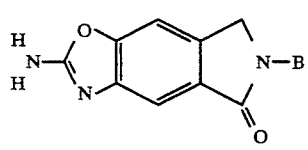
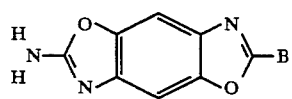
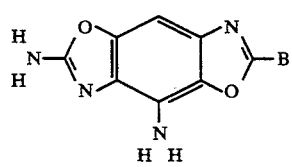
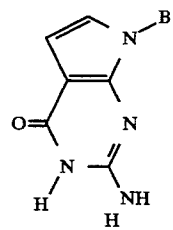
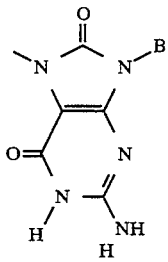
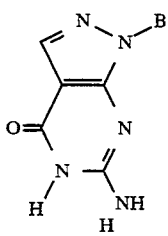
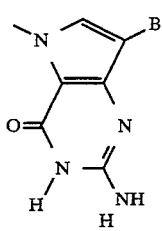
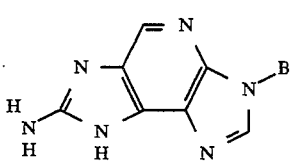
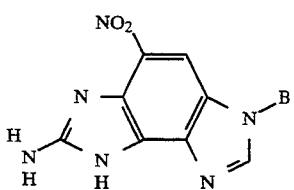
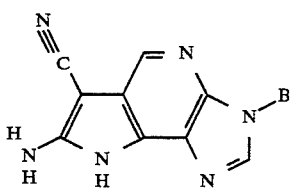
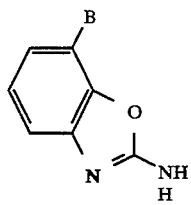
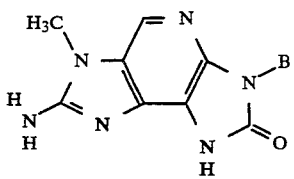

-continued
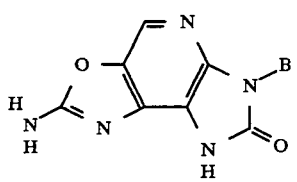
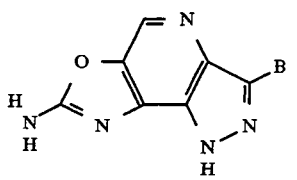
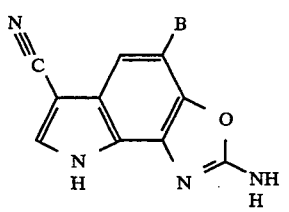
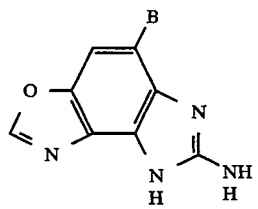
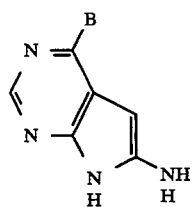
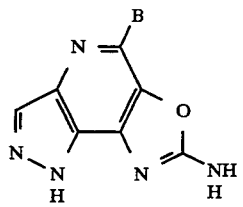
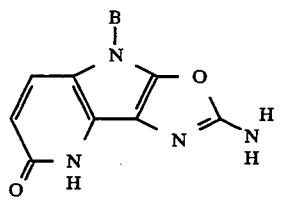
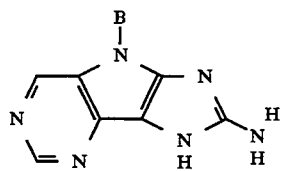
-continued
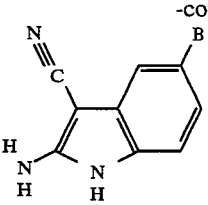
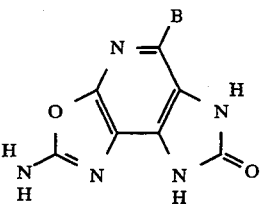
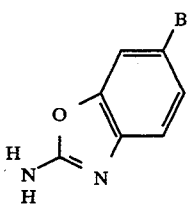
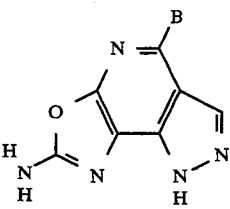
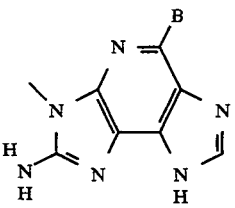
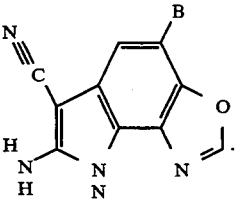
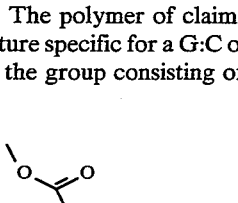
12. The polymer of claim 1, wherein at least one $R_i$ structure specific for a G:C oriented base pair is selected from the group consisting of the following bases:
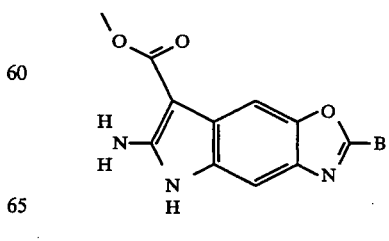

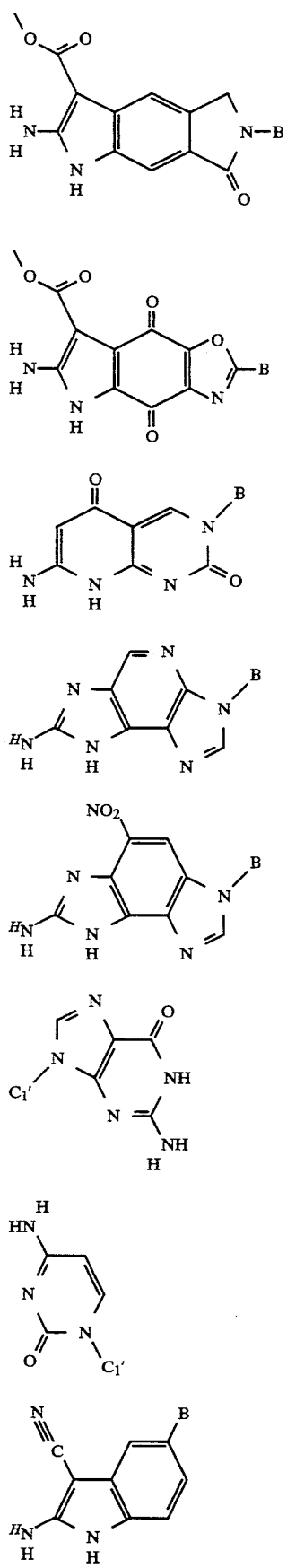
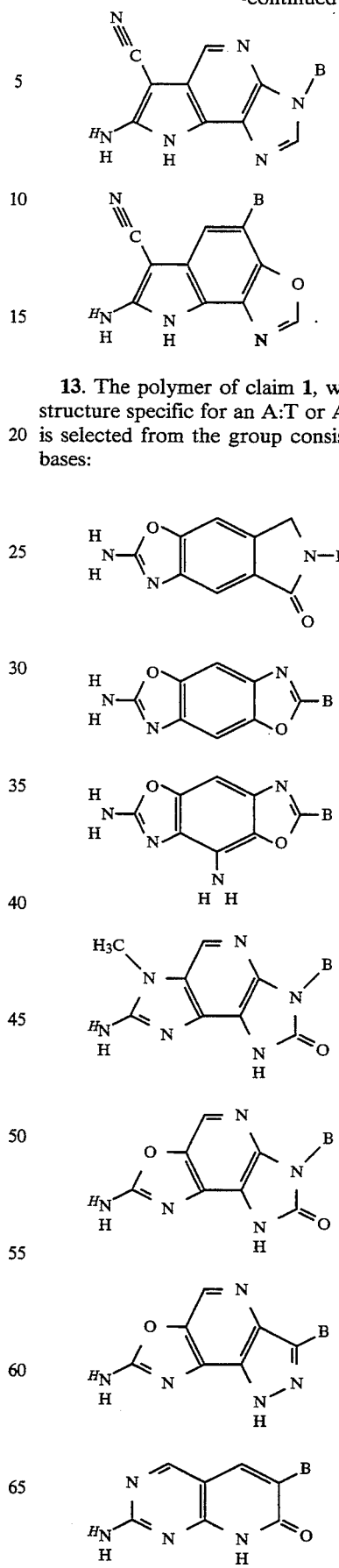
13. The polymer of claim 1, wherein at least one $R_i$ structure specific for an A:T or A:U oriented base-pair is selected from the group consisting of the following bases:

-continued
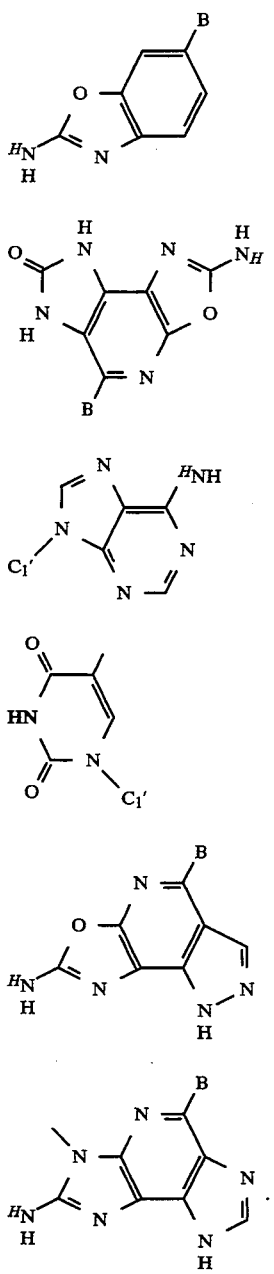
14. The polymer of claim 1, wherein at least one $R_i$ structure specific for a C:G oriented base-pair is selected from the group consisting of the following bases:
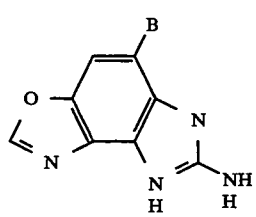
-continued
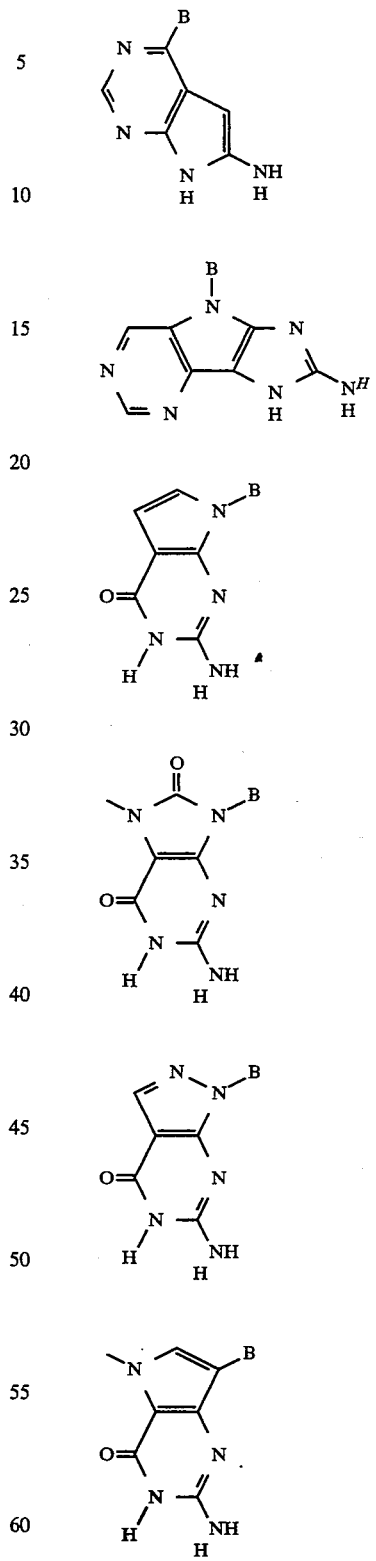
15. The polymer of claim 1, wherein at least one $R_i$ structure specific for an T:A or U:A oriented base-pair is selected from the group consisting of the following bases:

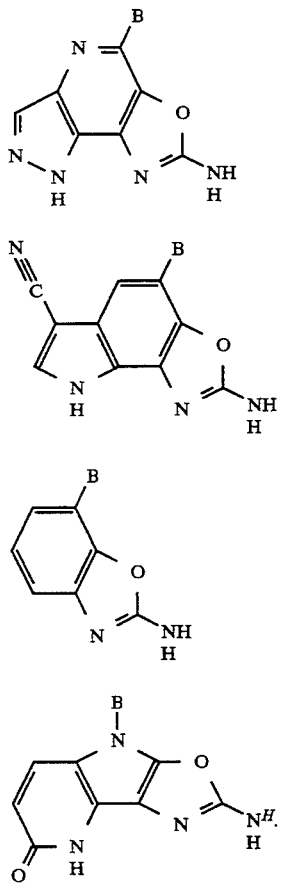

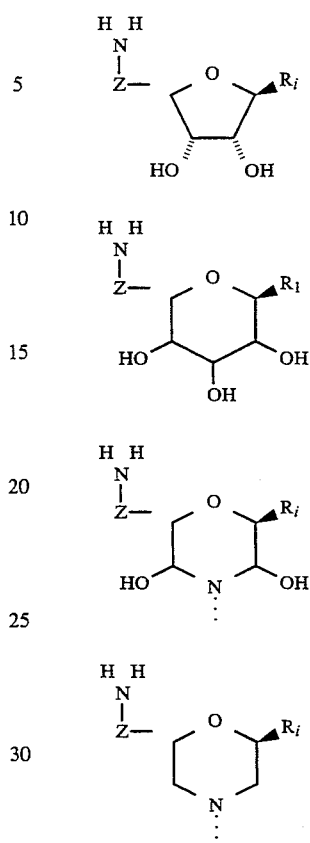

16. The polymer composition of claim 1, wherein up to about 30% of the $R_i$ groups in the polymer are cytosine, at polymer subunits corresponding to a G:C oriented base-pair in the target sequence, and thymine or uracil, at polymer subunits corresponding to A:T or A:U oriented base-pair in the target sequence.

17. The composition of claim 1, wherein the polymer contains one or more attached moieties effective to enhance the solubility of the polymer in aqueous medium.

18. A method for coupling a first free or polymer-terminal subunit having one of the following subunit forms:

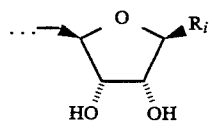

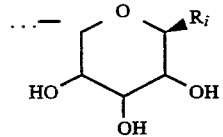

where $R_i$ is a planar ring structure having two or more hydrogen-bonding sites, with a second free or polymer-terminal subunit having one of the following subunit forms:

where Z is a 2-atom or 3-atom long moiety, said method comprising:

i) oxidizing the first subunit to generate a dialdehyde intermediate;

ii) contacting the dialdehyde intermediate with the second subunit under conditions effective to couple a primary amine to a dialdehyde; and (iii) adding a reducing agent effective to give a coupled structure selected from the following forms:

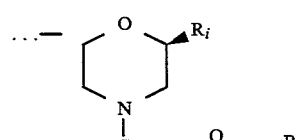

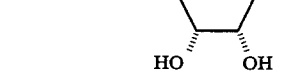

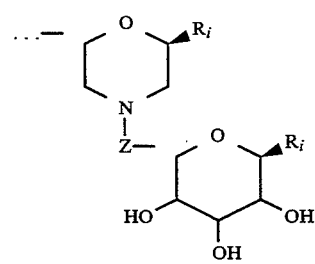

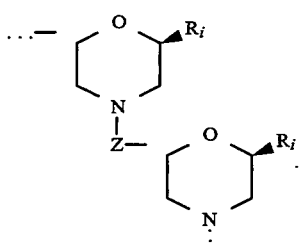

19. A method for isolating, from a liquid sample, a duplex nucleic acid having a selected target sequence of base-pairs, comprising:
  i) contacting the sample with a polymer reagent containing a structure which allows isolation of the reagent from solution, and attached to this structure, the polymer composition of claim 1 having a subunit sequence effective to bind in a sequence-specific manner with the selected target sequence of base-pairs, under conditions effective for sequence-specific binding of the polymer composition to the selected target sequence of base-pairs; and
  ii) separating the polymer reagent from the fluid sample.

20. The method of claim 19, for use in detecting the presence of such target fragment in a liquid sample, which further includes testing the separated polymer reagent for the presence of bound duplex nucleic acid.

21. The method of claim 20, wherein said polymer reagent includes a solid support with bound polymer composition, and said testing includes adding to the duplex nucleic acid, a fluorescent compound effective to intercalate into duplex DNA.

22. A subunit composition for use in forming a polymer composition effective to bind in a sequence specific manner to a target sequence in a duplex polynucleotide, comprising one of the following subunit structures:

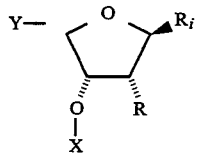
(a)

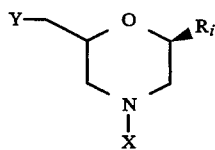
(b)

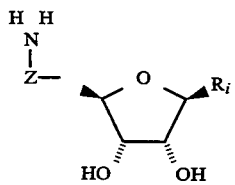
(c)

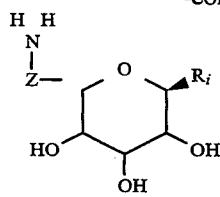
(d)

where R' is H, OH, or O-alkyl; the 5'-methylene has a $\beta$ stereochemical orientation in subunit forms (a), (c), and (d) and a uniform stereochemical orientation in subunit form (b); X is hydrogen or a protective group or a linking group suitable for joining the subunits in any selected order into a linear polymer; Y is a nucleophilic or electrophilic linking group suitable for joining the subunits in any selected order into a linear polymer; and X and Y together are such that when two subunits of the subunit set are linked the resulting intersubunit linkage is 2 or 3 atoms in length and uncharged; Z is a 2-atom or 3-atom long moiety; and, $R_i$, which may be in the protected state and has a $\beta$ stereochemical orientation, is selected from the group consisting of planar bases having the following skeletal ring structures and hydrogen bonding arrays, where B indicates the aliphatic backbone moiety:

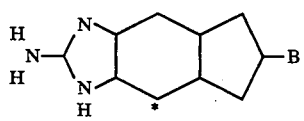

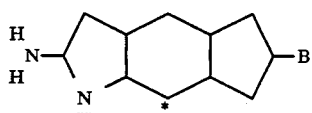

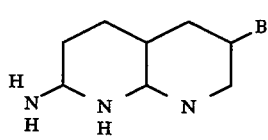

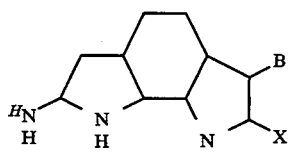

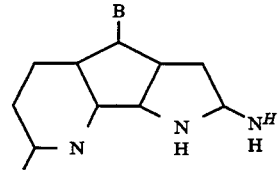

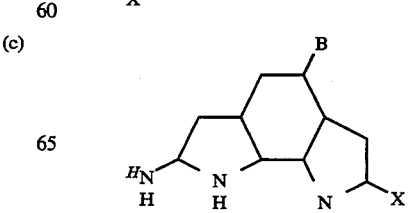

-continued

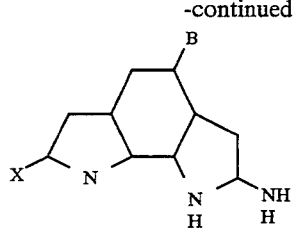
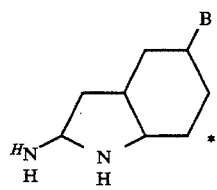
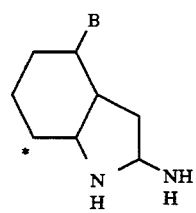

where the * ring position may carry a hydrogen-bond acceptor group; and X may be a moiety effective to afford discriminative binding on the basis of the moiety at the 5 position of the pyrimidine of the target base-pair; or, where $R_i$ is selected from the group consisting of planar bases having the following skeletal ring structures and hydrogen bonding arrays, where B indicates the aliphatic backbone moiety:

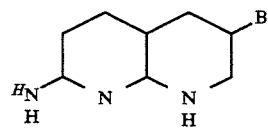
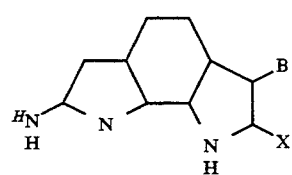
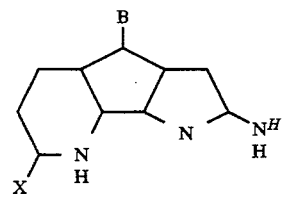
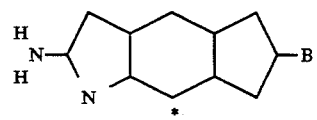

-continued

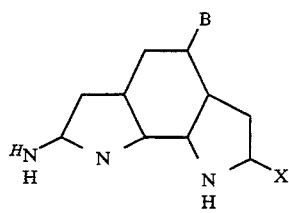
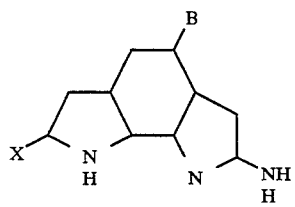
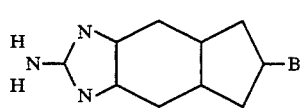
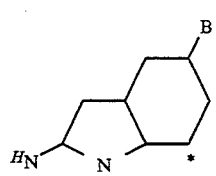
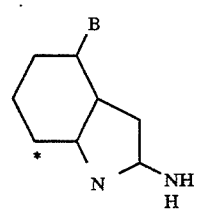

where the * ring position may carry a hydrogen-bond donating group; and X may be a moiety effective to afford discriminative binding on the basis of the moiety at the 5 position of the pyrimidine of the target base-pair.

23. A subunit composition for use in forming a polymer composition effective to bind in a sequence specific manner to a target sequence in a duplex polynucleotide, comprising one of the following subunit structures:

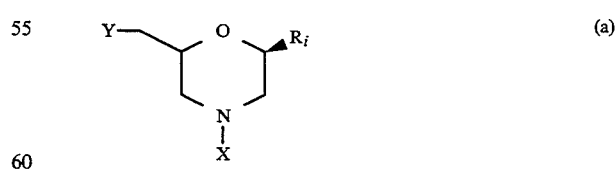 (a)

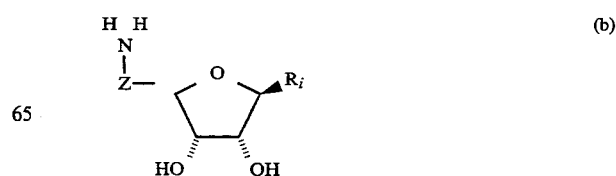 (b)

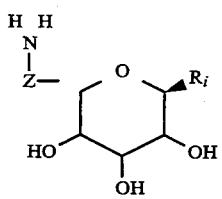

where the 5'-methylene has a β stereochemical orientation in subunit forms (b), and (c) and a uniform stereochemical orientation in subunit form (a); X is hydrogen or a protective group or a linking group suitable for joining the subunits in any selected order into a linear polymer; Y is a nucleophilic or electrophilic linking group suitable for joining the subunits in any selected order into a linear polymer; and X and Y together are such that when two subunits of the subunit set are linked the resulting intersubunit linkage is 2 or 3 atoms in length and uncharged; Z is a 2-atom or 3-atom long moiety; and, $R_i$, which may be in the protected state and has a β stereochemical orientation, is selected from the group consisting of planar bases having the following skeletal ring structures and hydrogen bonding arrays, where B indicates the aliphatic backbone moiety, the starred atom is not a hydrogen bond acceptor, and W is oxygen or sulfur:

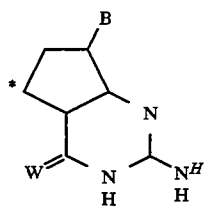

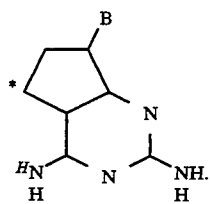

24. A polymer composition capable of discriminating, on the basis of binding affinity, between (a) a selected target sequence in a duplex polynucleotide containing at least one pyrimidine-purine base-pair at a selected position in the target sequence, wherein the pyrimidine base has a hydrogen on the 5 ring position, and (b) the same sequence but in which the primidine of the base pair at the selected position contains a methyl group on the 5 ring position of the pyrimidine, said composition comprising a polymer having the repeating unit $R_i$
—[B]— where B is a backbone moiety and where at least one $R_i$ is selected from the group consisting of

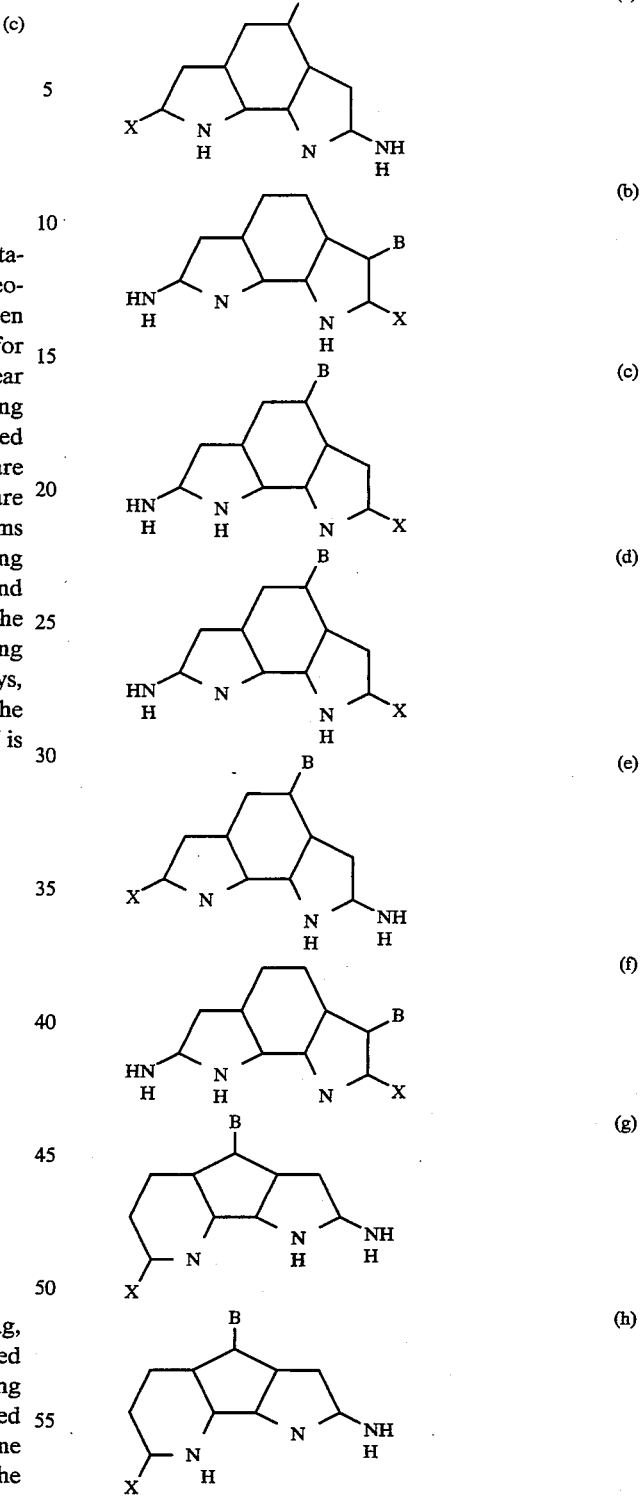

where X has a size and shape effective to selectively reduce binding of $R_i$ to a base-pair having a methyl on the 5 ring position of the pyrimidine.

25. The polymer of claim 24, wherein at least one $R_i$ is selected from the group consisting of (a), (b), (c), (d), (e) and (f), and where X is selected from the group consisting of sulfur, chlorine, bromine, cyano, azido, difluoromethyl and trifluoromethyl.

26. The polymer of claim 24, wherein at least one $R_i$ is selected from the group consisting of (g) and (h), and where X is selected from the group consisting of oxygen, fluorine, and methyl.

* * * * *